US011446155B2

(12) United States Patent
Engstrom

(10) Patent No.: US 11,446,155 B2
(45) Date of Patent: *Sep. 20, 2022

(54) EXPANDABLE CAGE

(71) Applicant: Medos International Sarl, Le Locle (CH)

(72) Inventor: Connor Engstrom, Hopkinton, MA (US)

(73) Assignee: MEDOS INTERNATIONAL SARL

( * ) Notice: Subject to any disclaimer, the term of this patent is extended or adjusted under 35 U.S.C. 154(b) by 0 days.

This patent is subject to a terminal disclaimer.

(21) Appl. No.: 16/512,043

(22) Filed: Jul. 15, 2019

(65) Prior Publication Data
US 2019/0336301 A1 Nov. 7, 2019

Related U.S. Application Data

(63) Continuation of application No. 15/589,209, filed on May 8, 2017, now Pat. No. 10,398,563.

(51) Int. Cl.
A61F 2/44 (2006.01)
A61F 2/46 (2006.01)
A61F 2/30 (2006.01)

(52) U.S. Cl.
CPC .............. *A61F 2/442* (2013.01); *A61F 2/447* (2013.01); *A61F 2/4425* (2013.01);
(Continued)

(58) Field of Classification Search
CPC .............. A61F 2/44–447; A61F 2/4637; A61F 2002/30556
See application file for complete search history.

(56) References Cited

U.S. PATENT DOCUMENTS

| 1,802,560 A | 4/1931 | Kerwin |
| 1,924,695 A | 8/1933 | Olson |

(Continued)

FOREIGN PATENT DOCUMENTS

| AU | 2006279558 A1 | 2/2007 |
| AU | 2005314079 B2 | 7/2012 |

(Continued)

OTHER PUBLICATIONS

Alfen et al., "Developments in the area of Endoscopic Spine Surgery", European Musculoskeletal Review 2006, pp. 23-24, ThessysTM, Transforaminal Endoscopic Spine Systems, joi max Medical Solutions.

(Continued)

*Primary Examiner* — Nicholas J Plionis
(74) *Attorney, Agent, or Firm* — BakerHostetler

(57) ABSTRACT

An intervertebral implant that iterates between collapsed and expanded configurations includes first and second plates spaced from one another along a first direction and defining bone-contacting surfaces facing away from each other along the first direction. An expansion assembly is positioned between the plates with respect to the first direction and includes a first support wedge that supports the first plate and defines a first ramp and a second support wedge that supports the second plate and defines second and third ramps. The expansion assembly includes an expansion wedge defining a fourth ramp. The first, second, third, and fourth ramps are each inclined with respect to a second direction that is substantially perpendicular to the first direction. At least one of the first and second support wedges is slidable along the respective supported first or second plate. The implant includes an actuator configured to apply a drive force to the expansion wedge so as to cause 1) the fourth ramp to ride along the third ramp so as to increase a (Continued)

distance between the bone-contacting surfaces along the first direction, and 2) the second ramp to ride along the first ramp, thereby further increasing the distance, thereby iterating the implant from the collapsed to the expanded configuration.

20 Claims, 24 Drawing Sheets

(52) U.S. Cl.
CPC .......... *A61F 2/4637* (2013.01); *A61F 2/4455* (2013.01); *A61F 2002/30387* (2013.01); *A61F 2002/30411* (2013.01); *A61F 2002/30507* (2013.01); *A61F 2002/30538* (2013.01); *A61F 2002/30556* (2013.01); *A61F 2002/443* (2013.01); *A61F 2002/4638* (2013.01)

(56) References Cited

U.S. PATENT DOCUMENTS

| | | |
|---|---|---|
| 1,965,653 A | 7/1934 | Kennedy |
| 2,077,804 A | 4/1937 | Morrison |
| 2,115,250 A | 4/1938 | Bruson |
| 2,121,193 A | 6/1938 | Hanicke |
| 2,170,111 A | 8/1939 | Bruson |
| 2,173,655 A | 9/1939 | Neracher et al. |
| 2,229,024 A | 1/1941 | Bruson |
| 2,243,717 A | 5/1941 | Moreira |
| 2,381,050 A | 8/1945 | Hardinge |
| 2,388,056 A | 10/1945 | Hendricks |
| 2,485,531 A | 10/1949 | William et al. |
| 2,489,870 A | 11/1949 | Dzus |
| 2,570,465 A | 10/1951 | Lundholm |
| 2,677,369 A | 5/1954 | Knowles |
| 2,706,701 A | 4/1955 | Hans et al. |
| 2,710,277 A | 6/1955 | Shelanski et al. |
| 2,826,532 A | 3/1958 | Hosmer |
| 2,900,305 A | 8/1959 | Siggia |
| 2,977,315 A | 3/1961 | Scheib et al. |
| 3,091,237 A | 5/1963 | Skinner |
| 3,112,743 A | 12/1963 | Cochran et al. |
| 3,115,804 A | 12/1963 | Johnson |
| 3,228,828 A | 1/1966 | Romano |
| 3,312,139 A | 4/1967 | Di Cristina |
| 3,486,505 A | 12/1969 | Morrison |
| 3,489,143 A | 1/1970 | Halloran |
| 3,648,294 A | 3/1972 | Shahrestani |
| 3,698,391 A | 10/1972 | Mahony |
| 3,717,655 A | 2/1973 | Godefroi et al. |
| 3,760,802 A | 9/1973 | Fischer et al. |
| 3,800,788 A | 4/1974 | White |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,855,638 A | 12/1974 | Pilliar |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,175,555 A | 11/1979 | Herbert |
| 4,205,399 A | 6/1980 | Jamiolkowski et al. |
| 4,236,512 A | 12/1980 | Aginsky |
| 4,249,435 A | 2/1981 | Smith et al. |
| 4,262,665 A | 4/1981 | Roalstad et al. |
| 4,262,676 A | 4/1981 | Jamshidi |
| 4,274,163 A | 6/1981 | Malcom et al. |
| 4,275,717 A | 6/1981 | Bolesky |
| 4,312,337 A | 1/1982 | Donohue |
| 4,312,353 A | 1/1982 | Shahbabian |
| 4,313,434 A | 2/1982 | Segal |
| 4,341,206 A | 7/1982 | Perrett et al. |
| 4,349,921 A | 9/1982 | Kuntz |
| 4,350,151 A | 9/1982 | Scott |
| 4,351,069 A | 9/1982 | Ballintyn et al. |
| 4,352,883 A | 10/1982 | Lim |
| 4,369,790 A | 1/1983 | Mccarthy |
| 4,399,814 A | 8/1983 | Pratt et al. |
| 4,401,112 A | 8/1983 | Rezaian |
| 4,401,433 A | 8/1983 | Luther |
| 4,409,974 A | 10/1983 | Freedland |
| 4,440,921 A | 4/1984 | Allcock et al. |
| 4,449,532 A | 5/1984 | Storz |
| 4,451,256 A | 5/1984 | Weikl et al. |
| 4,456,005 A | 6/1984 | Lichty |
| 4,462,394 A | 7/1984 | Jacobs |
| 4,463,753 A | 8/1984 | Gustilo |
| 4,466,435 A | 8/1984 | Murray |
| 4,467,479 A | 8/1984 | Brody |
| 4,488,543 A | 12/1984 | Tornier |
| 4,488,549 A | 12/1984 | Lee et al. |
| 4,494,535 A | 1/1985 | Haig |
| 4,495,174 A | 1/1985 | Allcock et al. |
| 4,532,660 A | 8/1985 | Field |
| 4,537,185 A | 8/1985 | Stednitz |
| 4,538,612 A | 9/1985 | Patrick, Jr. |
| 4,542,539 A | 9/1985 | Rowe et al. |
| 4,545,374 A | 10/1985 | Jacobson |
| 4,562,598 A | 1/1986 | Kranz |
| 4,573,448 A | 3/1986 | Kambin |
| 4,595,006 A | 6/1986 | Burke et al. |
| 4,601,710 A | 7/1986 | Moll |
| 4,625,722 A | 12/1986 | Murray |
| 4,625,725 A | 12/1986 | Davison et al. |
| 4,627,434 A | 12/1986 | Murray |
| 4,628,945 A | 12/1986 | Johnson, Jr. |
| 4,629,450 A | 12/1986 | Suzuki et al. |
| 4,630,616 A | 12/1986 | Tretinyak |
| 4,632,101 A | 12/1986 | Freedland |
| 4,640,271 A | 2/1987 | Lower |
| 4,641,640 A | 2/1987 | Griggs |
| 4,645,503 A | 2/1987 | Lin et al. |
| 4,646,741 A | 3/1987 | Smith |
| 4,651,717 A | 3/1987 | Jakubczak |
| 4,653,489 A | 3/1987 | Tronzo |
| 4,665,906 A | 5/1987 | Jervis |
| 4,667,663 A | 5/1987 | Miyata |
| 4,686,973 A | 8/1987 | Frisch |
| 4,686,984 A | 8/1987 | Bonnet |
| 4,688,561 A | 8/1987 | Reese |
| 4,697,584 A | 10/1987 | Haynes |
| 4,706,670 A | 11/1987 | Andersen et al. |
| 4,714,469 A | 12/1987 | Kenna |
| 4,714,478 A | 12/1987 | Fischer |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,772,287 A | 9/1988 | Ray et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,834,069 A | 5/1989 | Umeda |
| 4,834,757 A | 5/1989 | Brantigan |
| 4,838,282 A | 6/1989 | Strasser et al. |
| 4,858,601 A | 8/1989 | Glisson |
| 4,862,891 A | 9/1989 | Smith |
| 4,863,476 A | 9/1989 | Shepperd |
| 4,870,153 A | 9/1989 | Matzner et al. |
| 4,871,366 A | 10/1989 | Von et al. |

(56) References Cited

U.S. PATENT DOCUMENTS

| | | |
|---|---|---|
| 4,873,976 A | 10/1989 | Schreiber |
| 4,878,915 A | 11/1989 | Brantigan |
| 4,880,622 A | 11/1989 | Allcock et al. |
| 4,888,022 A | 12/1989 | Huebsch |
| 4,888,024 A | 12/1989 | Powlan |
| 4,889,119 A | 12/1989 | Jamiolkowski et al. |
| 4,892,550 A | 1/1990 | Huebsch |
| 4,896,662 A | 1/1990 | Noble |
| 4,898,186 A | 2/1990 | Ikada et al. |
| 4,898,577 A | 2/1990 | Badger et al. |
| 4,903,692 A | 2/1990 | Reese |
| 4,904,261 A | 2/1990 | Dove et al. |
| 4,911,718 A | 3/1990 | Lee et al. |
| 4,917,554 A | 4/1990 | Bronn |
| 4,932,969 A | 6/1990 | Frey et al. |
| 4,940,467 A | 7/1990 | Tronzo |
| 4,941,466 A | 7/1990 | Romano |
| 4,946,378 A | 8/1990 | Hirayama et al. |
| 4,959,064 A | 9/1990 | Engelhardt |
| 4,961,740 A | 10/1990 | Ray et al. |
| 4,963,144 A | 10/1990 | Huene |
| 4,966,587 A | 10/1990 | Rainer |
| 4,968,317 A | 11/1990 | Toermaelae et al. |
| 4,969,888 A | 11/1990 | Scholten et al. |
| 4,978,334 A | 12/1990 | Toye et al. |
| 4,978,349 A | 12/1990 | Robert |
| 4,981,482 A | 1/1991 | Ichikawa |
| 4,988,351 A | 1/1991 | Paulos et al. |
| 4,994,027 A | 2/1991 | Farrell |
| 4,995,200 A | 2/1991 | Eberhart |
| 5,002,557 A | 3/1991 | Hasson |
| 5,006,121 A | 4/1991 | Hafeli |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,019,082 A | 5/1991 | Frey et al. |
| 5,030,233 A | 7/1991 | Ducheyne |
| 5,051,189 A | 9/1991 | Farrah |
| 5,053,035 A | 10/1991 | Mclaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Lasner |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,719 A | 7/1992 | Winston |
| 5,133,755 A | 7/1992 | Brekke |
| 5,134,477 A | 7/1992 | Knauer et al. |
| 5,139,486 A | 8/1992 | Moss |
| 5,147,366 A | 9/1992 | Arroyo et al. |
| 5,158,543 A | 10/1992 | Lazarus |
| 5,163,939 A | 11/1992 | Winston |
| 5,163,989 A | 11/1992 | Campbell et al. |
| 5,167,663 A | 12/1992 | Brumfield |
| 5,167,664 A | 12/1992 | Hodorek |
| 5,169,400 A | 12/1992 | Muehling et al. |
| 5,169,402 A | 12/1992 | Elloy |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul et al. |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,217,462 A | 6/1993 | Asnis et al. |
| 5,217,475 A | 6/1993 | Kuber |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,250,061 A | 10/1993 | Michelson |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,320,644 A | 6/1994 | Baumgartner |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,397,364 A | 3/1995 | Kozak et al. |
| 5,401,269 A | 3/1995 | Buettner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |

(56) References Cited

U.S. PATENT DOCUMENTS

| | | |
|---|---|---|
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,365 A | 10/1995 | Bonutti |
| 5,454,790 A | 10/1995 | Dubrul |
| 5,454,815 A | 10/1995 | Geisser et al. |
| 5,454,827 A | 10/1995 | Aust et al. |
| 5,456,686 A | 10/1995 | Klapper et al. |
| 5,458,641 A | 10/1995 | Ramirez Jimenez |
| 5,458,643 A | 10/1995 | Oka et al. |
| 5,462,563 A | 10/1995 | Shearer et al. |
| 5,464,427 A | 11/1995 | Curtis et al. |
| 5,464,929 A | 11/1995 | Bezwada et al. |
| 5,468,245 A | 11/1995 | Vargas, III |
| 5,470,333 A | 11/1995 | Ray |
| 5,472,426 A | 12/1995 | Bonati et al. |
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | De et al. |
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buettner-Janz |
| 5,558,674 A | 9/1996 | Heggeness et al. |
| D374,287 S | 10/1996 | Goble et al. |
| 5,562,736 A | 10/1996 | Ray et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | Mcafee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,591,168 A | 1/1997 | Judet et al. |
| 5,593,409 A | 1/1997 | Michelson |
| 5,595,751 A | 1/1997 | Bezwada et al. |
| 5,597,579 A | 1/1997 | Bezwada et al. |
| 5,601,556 A | 2/1997 | Pisharodi |
| 5,601,561 A | 2/1997 | Terry et al. |
| 5,601,572 A | 2/1997 | Middleman et al. |
| 5,607,687 A | 3/1997 | Bezwada et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,618,552 A | 4/1997 | Bezwada et al. |
| 5,620,698 A | 4/1997 | Bezwada et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Lower et al. |
| 5,645,589 A | 7/1997 | Li |
| 5,645,596 A | 7/1997 | Kim et al. |
| 5,645,597 A | 7/1997 | Krapiva |
| 5,645,599 A | 7/1997 | Samani |
| 5,645,850 A | 7/1997 | Bezwada et al. |
| 5,647,857 A | 7/1997 | Anderson et al. |
| 5,648,088 A | 7/1997 | Bezwada et al. |
| 5,649,931 A | 7/1997 | Bryant et al. |
| 5,653,763 A | 8/1997 | Errico et al. |
| 5,658,335 A | 8/1997 | Allen |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,698,213 A | 12/1997 | Jamiolkowski et al. |
| 5,700,239 A | 12/1997 | Yoon |
| 5,700,583 A | 12/1997 | Jamiolkowski et al. |
| 5,702,391 A | 12/1997 | Lin |
| 5,702,449 A | 12/1997 | Mckay |
| 5,702,450 A | 12/1997 | Bisserie |
| 5,702,453 A | 12/1997 | Rabbe et al. |
| 5,702,454 A | 12/1997 | Baumgartner |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,531 A | 3/1998 | Shapiro |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |

(56) References Cited

U.S. PATENT DOCUMENTS

| | | |
|---|---|---|
| 5,762,629 A | 6/1998 | Kambin |
| 5,766,252 A | 6/1998 | Henry et al. |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,788,703 A | 8/1998 | Mittelmeier et al. |
| 5,792,044 A | 8/1998 | Foley et al. |
| 5,797,909 A | 8/1998 | Michelson |
| 5,800,549 A | 9/1998 | Bao et al. |
| 5,807,275 A | 9/1998 | Jamshidi |
| 5,807,327 A | 9/1998 | Green et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |
| 5,849,004 A | 12/1998 | Bramlet |
| 5,851,212 A | 12/1998 | Zirps et al. |
| 5,851,216 A | 12/1998 | Allen |
| 5,857,995 A | 1/1999 | Thomas et al. |
| 5,859,150 A | 1/1999 | Jamiolkowski et al. |
| 5,860,973 A | 1/1999 | Michelson |
| 5,860,977 A | 1/1999 | Zucherman et al. |
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,690 A | 5/1999 | Middleman et al. |
| 5,904,696 A | 5/1999 | Rosenman |
| 5,908,422 A | 6/1999 | Bresina |
| 5,916,228 A | 6/1999 | Ripich et al. |
| 5,916,267 A | 6/1999 | Prakit |
| 5,919,235 A | 7/1999 | Husson et al. |
| 5,925,056 A | 7/1999 | Thomas et al. |
| 5,925,074 A | 7/1999 | Gingras et al. |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | Mcdevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao et al. |
| 5,976,187 A | 11/1999 | Richelsoph |
| 5,980,522 A | 11/1999 | Koros et al. |
| 5,984,927 A | 11/1999 | Wenstrom et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lehto et al. |
| 6,010,508 A | 1/2000 | Bradley |
| 6,010,513 A | 1/2000 | Toermaelae et al. |
| 6,012,494 A | 1/2000 | Balazs |
| 6,015,410 A | 1/2000 | Toermaelae et al. |
| 6,015,436 A | 1/2000 | Schonhoffer |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Losken et al. |
| 6,036,701 A | 3/2000 | Rosenman |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochschuler et al. |
| 6,048,309 A | 4/2000 | Flom et al. |
| 6,048,342 A | 4/2000 | Zuckerman et al. |
| 6,048,346 A | 4/2000 | Reiley et al. |
| 6,048,360 A | 4/2000 | Khosravi et al. |
| 6,053,922 A | 4/2000 | Krause et al. |
| 6,053,935 A | 4/2000 | Brenneman et al. |
| 6,056,763 A | 5/2000 | Parsons |
| 6,063,121 A | 5/2000 | Xavier et al. |
| 6,066,142 A | 5/2000 | Serbousek et al. |
| 6,066,154 A | 5/2000 | Reiley et al. |
| 6,066,175 A | 5/2000 | Henderson et al. |
| 6,068,630 A | 5/2000 | Zuckerman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zuckerman et al. |
| 6,080,155 A | 6/2000 | Michelson |
| 6,080,158 A | 6/2000 | Lin |
| 6,080,193 A | 6/2000 | Hochschuler et al. |
| 6,083,225 A | 7/2000 | Winslow et al. |
| 6,083,244 A | 7/2000 | Lubbers et al. |
| 6,090,112 A | 7/2000 | Zuckerman et al. |
| 6,090,143 A | 7/2000 | Meriwether et al. |
| 6,096,038 A | 8/2000 | Michelson |
| 6,096,080 A | 8/2000 | Nicholson et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,637 A | 9/2000 | Gill et al. |

(56) References Cited

U.S. PATENT DOCUMENTS

| | | |
|---|---|---|
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,120,508 A | 9/2000 | Gruenig et al. |
| 6,123,705 A | 9/2000 | Michelson |
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A | 10/2000 | Young |
| 6,136,031 A | 10/2000 | Middleton |
| 6,139,558 A | 10/2000 | Wagner |
| 6,139,579 A | 10/2000 | Steffee et al. |
| 6,146,384 A | 11/2000 | Lee et al. |
| 6,146,387 A | 11/2000 | Trott et al. |
| 6,146,420 A | 11/2000 | Mckay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Espinosa |
| 6,162,234 A | 12/2000 | Freedland et al. |
| 6,162,236 A | 12/2000 | Osada |
| 6,162,252 A | 12/2000 | Kuras et al. |
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | Macphee et al. |
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,235,030 B1 | 5/2001 | Zuckerman et al. |
| 6,235,043 B1 | 5/2001 | Reiley et al. |
| 6,238,397 B1 | 5/2001 | Zuckerman et al. |
| 6,238,491 B1 | 5/2001 | Davidson et al. |
| 6,241,733 B1 | 6/2001 | Nicholson et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Toermaelae et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,258,093 B1 | 7/2001 | Edwards et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,277,149 B1 | 8/2001 | Boyle et al. |
| 6,280,444 B1 | 8/2001 | Zuckerman et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,287,313 B1 | 9/2001 | Sasso |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,644 B1 | 10/2001 | Saurat et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,177 B1 | 10/2001 | Felt et al. |
| D450,676 S | 11/2001 | Huttner |
| 6,312,443 B1 | 11/2001 | Stone |
| 6,319,254 B1 | 11/2001 | Giet et al. |
| 6,319,272 B1 | 11/2001 | Brenneman et al. |
| 6,331,312 B1 | 12/2001 | Lee et al. |
| 6,332,882 B1 | 12/2001 | Zuckerman et al. |
| 6,332,883 B1 | 12/2001 | Zuckerman et al. |
| 6,332,894 B1 | 12/2001 | Stalcup et al. |
| 6,332,895 B1 | 12/2001 | Suddaby |
| 6,342,074 B1 | 1/2002 | Simpson |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,897 B1 | 4/2002 | Bonutti |
| 6,368,325 B1 | 4/2002 | Mckinley et al. |
| 6,368,350 B1 | 4/2002 | Erickson et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,681 B1 | 4/2002 | Truscott |
| 6,375,682 B1 | 4/2002 | Fleischmann et al. |
| 6,375,683 B1 | 4/2002 | Crozet et al. |
| 6,379,355 B1 | 4/2002 | Zuckerman et al. |
| 6,379,363 B1 | 4/2002 | Herrington et al. |
| 6,387,130 B1 | 5/2002 | Stone et al. |
| 6,398,793 B1 | 6/2002 | McGuire |
| 6,402,750 B1 | 6/2002 | Atkinson et al. |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Bret |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | Mcguckin et al. |

(56) References Cited

U.S. PATENT DOCUMENTS

| | | |
|---|---|---|
| 6,425,919 B1 | 7/2002 | Lambrecht |
| 6,425,920 B1 | 7/2002 | Hamada |
| 6,428,541 B1 | 8/2002 | Boyd et al. |
| 6,428,556 B1 | 8/2002 | Chin |
| 6,436,101 B1 | 8/2002 | Hamada |
| 6,436,140 B1 | 8/2002 | Liu et al. |
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,518 B1 | 9/2002 | Krause et al. |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,461,359 B1 | 10/2002 | Tribus et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |
| 6,485,491 B1 | 11/2002 | Farris et al. |
| 6,485,518 B1 | 11/2002 | Cornwall et al. |
| D467,657 S | 12/2002 | Scribner |
| 6,488,693 B2 | 12/2002 | Gannoe et al. |
| 6,488,710 B2 | 12/2002 | Besselink |
| 6,489,309 B1 | 12/2002 | Singh et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul et al. |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,839 B1 | 1/2003 | Lambrecht et al. |
| 6,511,471 B2 | 1/2003 | Rosenman et al. |
| 6,511,481 B2 | 1/2003 | Von et al. |
| 6,512,958 B1 | 1/2003 | Swoyer et al. |
| D469,871 S | 2/2003 | Sand |
| 6,514,256 B2 | 2/2003 | Zuckerman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,774 B2 | 3/2003 | Lieberman |
| 6,527,803 B1 | 3/2003 | Crozet et al. |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | Mcguire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,389 B2 | 5/2003 | Clark et al. |
| 6,558,390 B2 | 5/2003 | Cragg |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,293 B1 | 6/2003 | Chandran |
| 6,579,320 B1 | 6/2003 | Gauchet et al. |
| 6,579,321 B1 | 6/2003 | Gordon et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,066 B2 | 8/2003 | Dinger et al. |
| 6,610,091 B1 | 8/2003 | Reiley |
| 6,610,094 B2 | 8/2003 | Husson |
| 6,613,050 B1 | 9/2003 | Wagner et al. |
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Taylor |
| 6,629,998 B1 | 10/2003 | Lin |
| 6,632,224 B2 | 10/2003 | Cachia et al. |
| 6,632,235 B2 | 10/2003 | Weikel et al. |
| 6,635,059 B2 | 10/2003 | Randall et al. |
| 6,635,060 B2 | 10/2003 | Hanson et al. |
| 6,635,362 B2 | 10/2003 | Zheng |
| RE38,335 E | 11/2003 | Aust et al. |
| D482,787 S | 11/2003 | Reiss |
| 6,641,564 B1 | 11/2003 | Kraus |
| 6,641,582 B1 | 11/2003 | Hanson et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,004 B2 | 12/2003 | Barker et al. |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm et al. |
| 6,669,698 B1 | 12/2003 | Tromanhauser et al. |
| 6,669,729 B2 | 12/2003 | Chin |

(56) References Cited

U.S. PATENT DOCUMENTS

| | | |
|---|---|---|
| 6,669,732 B2 | 12/2003 | Serhan et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |
| 6,679,915 B1 | 1/2004 | Cauthen |
| 6,682,535 B2 | 1/2004 | Hoogland |
| 6,682,561 B2 | 1/2004 | Songer et al. |
| 6,682,562 B2 | 1/2004 | Viart et al. |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Toermaelae et al. |
| 6,692,563 B2 | 2/2004 | Zimmermann |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,126 B2 | 5/2004 | Boehm et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,746,451 B2 | 6/2004 | Middleton et al. |
| 6,749,560 B1 | 6/2004 | Konstorum et al. |
| 6,752,831 B2 | 6/2004 | Sybert et al. |
| 6,755,837 B2 | 6/2004 | Ebner |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,847 B2 | 7/2004 | Maguire |
| 6,758,861 B2 | 7/2004 | Ralph et al. |
| 6,758,862 B2 | 7/2004 | Berry et al. |
| 6,761,720 B1 | 7/2004 | Senegas |
| 6,764,491 B2 | 7/2004 | Frey et al. |
| 6,764,514 B1 | 7/2004 | Li et al. |
| D495,417 S | 8/2004 | Doelling et al. |
| 6,770,075 B2 | 8/2004 | Howland |
| 6,773,460 B2 | 8/2004 | Jackson |
| 6,780,151 B2 | 8/2004 | Grabover et al. |
| 6,783,530 B1 | 8/2004 | Levy |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,941 B2 | 1/2005 | Rogers et al. |
| 6,840,944 B2 | 1/2005 | Suddaby |
| 6,852,126 B2 | 2/2005 | Ahlgren |
| 6,852,127 B2 | 2/2005 | Varga et al. |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,878,167 B2 | 4/2005 | Ferree |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | Mckinley et al. |
| 6,890,333 B2 | 5/2005 | Von et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zucherman et al. |
| 6,905,512 B2 | 6/2005 | Paes et al. |
| 6,908,465 B2 | 6/2005 | Von et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B2 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,949,108 B2 | 9/2005 | Holmes |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,966,912 B2 | 11/2005 | Michelson |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,004,971 B2 | 2/2006 | Serhan et al. |
| 7,008,431 B2 | 3/2006 | Simonson |
| 7,008,453 B1 | 3/2006 | Michelson |

(56) References Cited

U.S. PATENT DOCUMENTS

| | | |
|---|---|---|
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | Mckay |
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,037,339 B2 | 5/2006 | Houfburg |
| 7,041,107 B2 | 5/2006 | Pohjonen et al. |
| 7,044,954 B2 | 5/2006 | Reiley et al. |
| 7,048,694 B2 | 5/2006 | Mark et al. |
| 7,048,736 B2 | 5/2006 | Robinson et al. |
| 7,060,068 B2 | 6/2006 | Tromanhauser et al. |
| 7,060,073 B2 | 6/2006 | Frey et al. |
| 7,063,701 B2 | 6/2006 | Michelson |
| 7,063,702 B2 | 6/2006 | Michelson |
| 7,063,703 B2 | 6/2006 | Reo |
| 7,063,725 B2 | 6/2006 | Foley |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,074,226 B2 | 7/2006 | Roehm et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,053 B2 | 8/2006 | Vanney |
| 7,087,055 B2 | 8/2006 | Lim et al. |
| 7,087,083 B2 | 8/2006 | Pasquet et al. |
| 7,089,063 B2 | 8/2006 | Lesh et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,125,424 B2 | 10/2006 | Banick et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,156,877 B2 | 1/2007 | Lotz et al. |
| 7,163,558 B2 | 1/2007 | Senegas et al. |
| 7,166,107 B2 | 1/2007 | Anderson |
| 7,172,612 B2 | 2/2007 | Ishikawa |
| 7,179,293 B2 | 2/2007 | Mckay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,482 B2 | 6/2007 | Messerli et al. |
| 7,226,483 B2 | 6/2007 | Gerber et al. |
| 7,235,101 B2 | 6/2007 | Berry et al. |
| 7,238,204 B2 | 7/2007 | Le et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,683 B2 | 9/2007 | Sharkey et al. |
| 7,267,687 B2 | 9/2007 | Mcguckin, Jr. |
| 7,270,679 B2 | 9/2007 | Istephanous et al. |
| 7,276,062 B2 | 10/2007 | Mcdaniel et al. |
| 7,282,061 B2 | 10/2007 | Sharkey et al. |
| 7,291,173 B2 | 11/2007 | Richelsoph et al. |
| 7,300,440 B2 | 11/2007 | Zdeblick et al. |
| 7,306,628 B2 | 12/2007 | Zucherman et al. |
| 7,309,357 B2 | 12/2007 | Kim |
| 7,311,713 B2 | 12/2007 | Johnson et al. |
| 7,316,714 B2 | 1/2008 | Gordon et al. |
| 7,318,840 B2 | 1/2008 | Mckay |
| 7,320,689 B2 | 1/2008 | Keller |
| 7,320,708 B1 | 1/2008 | Bernstein |
| 7,322,962 B2 | 1/2008 | Forrest |
| 7,326,211 B2 | 2/2008 | Padget et al. |
| 7,326,248 B2 | 2/2008 | Michelson |
| 7,335,203 B2 | 2/2008 | Winslow et al. |
| 7,351,262 B2 | 4/2008 | Bindseil et al. |
| 7,361,140 B2 | 4/2008 | Ries et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,406,775 B2 | 8/2008 | Funk et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,442,211 B2 | 10/2008 | De et al. |
| 7,445,636 B2 | 11/2008 | Michelson |
| 7,445,637 B2 | 11/2008 | Taylor |
| 7,470,273 B2 | 12/2008 | Dougherty-Shah |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,485,134 B2 | 2/2009 | Simonson |
| 7,488,326 B2 | 2/2009 | Elliott |
| 7,491,237 B2 | 2/2009 | Randall et al. |
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,054 B2 | 8/2009 | Michelson |
| 7,569,074 B2 | 8/2009 | Eisermann et al. |
| 7,572,279 B2 | 8/2009 | Jackson |
| 7,575,580 B2 | 8/2009 | Lim et al. |
| 7,575,599 B2 | 8/2009 | Villiers et al. |
| 7,578,820 B2 | 8/2009 | Moore et al. |
| 7,588,574 B2 | 9/2009 | Assell et al. |
| 7,601,173 B2 | 10/2009 | Messerli et al. |
| 7,608,083 B2 | 10/2009 | Lee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,377 B2 | 12/2009 | Veldhuizen et al. |
| 7,625,378 B2 | 12/2009 | Foley |
| 7,625,394 B2 | 12/2009 | Molz et al. |
| 7,637,905 B2 | 12/2009 | Saadat et al. |
| 7,641,657 B2 | 1/2010 | Cragg |
| 7,641,670 B2 | 1/2010 | Davison et al. |
| 7,641,692 B2 | 1/2010 | Bryan et al. |

(56) References Cited

U.S. PATENT DOCUMENTS

| | | |
|---|---|---|
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,666,186 B2 | 2/2010 | Harp |
| 7,666,266 B2 | 2/2010 | Izawa et al. |
| 7,670,354 B2 | 3/2010 | Davison et al. |
| 7,670,374 B2 | 3/2010 | Schaller |
| 7,674,265 B2 | 3/2010 | Smith et al. |
| 7,674,273 B2 | 3/2010 | Davison et al. |
| 7,682,370 B2 | 3/2010 | Pagliuca et al. |
| 7,682,400 B2 | 3/2010 | Zwirkoski |
| 7,691,120 B2 | 4/2010 | Shluzas et al. |
| 7,691,147 B2 | 4/2010 | Guetlin et al. |
| 7,699,878 B2 | 4/2010 | Pavlov et al. |
| 7,703,727 B2 | 4/2010 | Selness |
| 7,704,280 B2 | 4/2010 | Lechmann et al. |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,731,751 B2 | 6/2010 | Butler et al. |
| 7,740,633 B2 | 6/2010 | Assell et al. |
| 7,744,599 B2 | 6/2010 | Cragg |
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Ainsworth |
| 7,763,028 B2 | 7/2010 | Lim et al. |
| 7,763,038 B2 | 7/2010 | O'Brien |
| 7,763,055 B2 | 7/2010 | Foley |
| 7,766,930 B2 | 8/2010 | Dipoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,080 B2 | 9/2010 | Doty |
| 7,799,081 B2 | 9/2010 | Mckinley |
| 7,799,083 B2 | 9/2010 | Smith et al. |
| 7,803,161 B2 | 9/2010 | Foley et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | Lehuec et al. |
| 7,837,734 B2 | 11/2010 | Zuckerman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons, Jr. |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,909,874 B2 | 3/2011 | Zielinski |
| 7,918,874 B2 | 4/2011 | Siegal |
| 7,922,719 B2 | 4/2011 | Ralph et al. |
| 7,922,729 B2 | 4/2011 | Michelson |
| 7,931,674 B2 | 4/2011 | Zucherman et al. |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,967 B1 | 6/2011 | Woods |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,403 B2 | 8/2011 | Foley et al. |
| 7,998,176 B2 | 8/2011 | Culbert |
| 8,007,535 B2 | 8/2011 | Hudgins et al. |
| 8,012,212 B2 | 9/2011 | Link et al. |
| 8,021,424 B2 | 9/2011 | Beger et al. |
| 8,021,426 B2 | 9/2011 | Segal et al. |
| 8,025,697 B2 | 9/2011 | Mcclellan et al. |
| 8,034,109 B2 | 10/2011 | Zwirkoski |
| 8,034,110 B2 | 10/2011 | Garner et al. |
| 8,038,703 B2 | 10/2011 | Dobak et al. |
| 8,043,293 B2 | 10/2011 | Warnick |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,100,978 B2 | 1/2012 | Bass |
| 8,105,382 B2 | 1/2012 | Olmos et al. |
| 8,109,972 B2 | 2/2012 | Zucherman et al. |
| 8,109,977 B2 | 2/2012 | Culbert et al. |
| 8,114,088 B2 | 2/2012 | Miller |
| 8,118,871 B2 | 2/2012 | Gordon |
| 8,128,700 B2 | 3/2012 | Delurio et al. |
| 8,128,702 B2 | 3/2012 | Zucherman et al. |
| 8,133,232 B2 | 3/2012 | Levy et al. |
| 8,147,549 B2 | 4/2012 | Metcalf et al. |
| 8,177,812 B2 | 5/2012 | Sankaran |
| 8,187,327 B2 | 5/2012 | Edidin et al. |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,216,317 B2 | 7/2012 | Thibodeau |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,675 B2 | 7/2012 | Rhoda |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,241,364 B2 | 8/2012 | Hansell et al. |
| 8,246,622 B2 | 8/2012 | Siegal et al. |
| 8,257,440 B2 | 9/2012 | Gordon et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,287,599 B2 | 10/2012 | Mcguckin, Jr. |
| 8,292,959 B2 | 10/2012 | Webb et al. |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,343,193 B2 | 1/2013 | Johnson et al. |

(56) References Cited

U.S. PATENT DOCUMENTS

| | | |
|---|---|---|
| 8,343,222 B2 | 1/2013 | Cope |
| 8,353,961 B2 | 1/2013 | Mcclintock et al. |
| 8,361,154 B2 | 1/2013 | Reo |
| 8,366,777 B2 | 2/2013 | Matthis et al. |
| 8,377,098 B2 | 2/2013 | Landry et al. |
| 8,377,133 B2 | 2/2013 | Yuan et al. |
| 8,382,842 B2 | 2/2013 | Greenhalgh et al. |
| 8,394,129 B2 | 3/2013 | Morgenstern et al. |
| 8,398,712 B2 | 3/2013 | De et al. |
| 8,398,713 B2 | 3/2013 | Weiman |
| 8,403,990 B2 | 3/2013 | Dryer et al. |
| 8,409,282 B2 | 4/2013 | Kim |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,425,559 B2 | 4/2013 | Tebbe et al. |
| 8,435,298 B2 | 5/2013 | Weiman |
| 8,454,617 B2 | 6/2013 | Schaller et al. |
| 8,454,698 B2 | 6/2013 | De et al. |
| 8,465,524 B2 | 6/2013 | Siegal |
| 8,480,715 B2 | 7/2013 | Gray |
| 8,480,742 B2 | 7/2013 | Pisharodi |
| 8,480,748 B2 | 7/2013 | Poulos |
| 8,486,109 B2 | 7/2013 | Siegal |
| 8,486,148 B2 | 7/2013 | Butler et al. |
| 8,491,591 B2 | 7/2013 | Fuerderer |
| 8,491,653 B2 | 7/2013 | Zucherman et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,523,909 B2 | 9/2013 | Hess |
| 8,523,944 B2 | 9/2013 | Jimenez et al. |
| 8,535,380 B2 | 9/2013 | Greenhalgh et al. |
| 8,545,567 B1 | 10/2013 | Krueger |
| 8,551,092 B2 | 10/2013 | Morgan et al. |
| 8,551,173 B2 | 10/2013 | Lechmann et al. |
| 8,556,978 B2 | 10/2013 | Schaller |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,583 B2 | 11/2013 | Schaller et al. |
| 8,591,585 B2 | 11/2013 | Mclaughlin et al. |
| 8,597,330 B2 | 12/2013 | Siegal |
| 8,597,333 B2 | 12/2013 | Morgenstern et al. |
| 8,597,360 B2 | 12/2013 | Mcluen et al. |
| 8,603,168 B2 | 12/2013 | Gordon et al. |
| 8,603,170 B2 | 12/2013 | Cipoletti et al. |
| 8,603,177 B2 | 12/2013 | Gray |
| 8,623,091 B2 | 1/2014 | Suedkamp et al. |
| 8,628,576 B2 | 1/2014 | Triplett et al. |
| 8,628,577 B1 | 1/2014 | Jimenez |
| 8,628,578 B2 | 1/2014 | Miller et al. |
| 8,632,595 B2 | 1/2014 | Weiman |
| 8,636,746 B2 | 1/2014 | Jimenez et al. |
| 8,641,764 B2 | 2/2014 | Gately |
| 8,663,329 B2 | 3/2014 | Ernst |
| 8,663,331 B2 | 3/2014 | McClellan et al. |
| 8,668,740 B2 | 3/2014 | Rhoda et al. |
| 8,672,977 B2 | 3/2014 | Siegal et al. |
| 8,679,161 B2 | 3/2014 | Malandain et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,702,757 B2 | 4/2014 | Thommen et al. |
| 8,702,798 B2 | 4/2014 | Matthis et al. |
| 8,709,086 B2 | 4/2014 | Glerum |
| 8,709,088 B2 | 4/2014 | Kleiner et al. |
| 8,715,351 B1 | 5/2014 | Pinto |
| 8,721,723 B2 | 5/2014 | Hansell et al. |
| 8,728,160 B2 | 5/2014 | Globerman et al. |
| 8,728,166 B2 | 5/2014 | Schwab |
| 8,740,954 B2 | 6/2014 | Ghobrial et al. |
| 8,753,398 B2 | 6/2014 | Gordon et al. |
| 8,758,349 B2 | 6/2014 | Germain et al. |
| 8,758,441 B2 | 6/2014 | Hovda et al. |
| 8,764,806 B2 | 7/2014 | Abdou |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | De et al. |
| 8,808,376 B2 | 8/2014 | Schaller |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,733 B2 | 9/2014 | O'Neil et al. |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,235 B2 | 12/2014 | Siegal |
| 8,900,307 B2 | 12/2014 | Hawkins et al. |
| 8,906,098 B2 | 12/2014 | Siegal |
| 8,920,506 B2 | 12/2014 | McGuckin, Jr. |
| 8,926,704 B2 | 1/2015 | Glerum et al. |
| 8,936,641 B2 | 1/2015 | Cain |
| 8,940,049 B1 * | 1/2015 | Jimenez .......... A61F 2/447 |
| | | 623/17.15 |
| 8,940,050 B2 | 1/2015 | Laurence et al. |
| 8,940,052 B2 | 1/2015 | Lechmann et al. |
| 8,961,609 B2 | 2/2015 | Schaller |
| 8,968,408 B2 | 3/2015 | Schaller et al. |
| 8,979,860 B2 | 3/2015 | Voellmicke et al. |
| 8,979,929 B2 | 3/2015 | Schaller |
| 8,986,387 B1 | 3/2015 | To et al. |
| 8,986,388 B2 | 3/2015 | Siegal et al. |
| 8,986,389 B2 | 3/2015 | Lim et al. |
| 9,005,291 B2 | 4/2015 | Loebl et al. |
| 9,017,408 B2 | 4/2015 | Siegal et al. |
| 9,017,413 B2 | 4/2015 | Siegal et al. |
| 9,039,767 B2 | 5/2015 | Raymond et al. |
| 9,039,771 B2 | 5/2015 | Glerum et al. |
| 9,044,334 B2 | 6/2015 | Siegal et al. |
| 9,044,338 B2 | 6/2015 | Schaller |
| 9,060,876 B1 | 6/2015 | To et al. |
| 9,066,808 B2 | 6/2015 | Schaller |
| 9,078,767 B1 | 7/2015 | Mclean |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,101,491 B2 | 8/2015 | Rodgers et al. |
| 9,101,492 B2 | 8/2015 | Mangione et al. |
| 9,107,766 B1 | 8/2015 | Mclean et al. |
| 9,119,730 B2 * | 9/2015 | Glerum .......... A61F 2/4611 |
| 9,237,956 B1 | 1/2016 | Jensen |
| 9,254,138 B2 | 2/2016 | Siegal et al. |
| 9,259,326 B2 | 2/2016 | Schaller |
| 9,271,846 B2 | 3/2016 | Lim et al. |
| 9,277,928 B2 | 3/2016 | Morgenstern Lopez |
| 9,282,979 B2 | 3/2016 | O'Neil et al. |
| 9,283,092 B2 | 3/2016 | Siegal et al. |
| 9,295,562 B2 | 3/2016 | Lechmann et al. |
| 9,314,348 B2 | 4/2016 | Emstad |
| 9,326,866 B2 | 5/2016 | Schaller et al. |
| 9,333,091 B2 | 5/2016 | Dimauro |
| 9,387,087 B2 | 7/2016 | Tyber |
| 9,402,732 B2 | 8/2016 | Gabelberger |
| 9,402,739 B2 | 8/2016 | Weiman et al. |
| 9,408,712 B2 | 8/2016 | Siegal et al. |
| 9,414,923 B2 | 8/2016 | Studer et al. |
| 9,414,934 B2 | 8/2016 | Cain |

(56) References Cited

U.S. PATENT DOCUMENTS

| | | |
|---|---|---|
| 9,414,936 B2 | 8/2016 | Miller et al. |
| 9,433,510 B2 | 9/2016 | Lechmann et al. |
| 9,439,776 B2 | 9/2016 | Dimauro et al. |
| 9,439,777 B2 | 9/2016 | Dimauro |
| 9,445,825 B2 | 9/2016 | Belaney et al. |
| 9,445,918 B1 | 9/2016 | Lin et al. |
| 9,463,099 B2 | 10/2016 | Levy et al. |
| 9,474,623 B2 | 10/2016 | Cain |
| 9,510,954 B2 | 12/2016 | Glerum et al. |
| 9,532,884 B2 | 1/2017 | Siegal et al. |
| 9,566,167 B2 | 2/2017 | Barrus et al. |
| 9,579,215 B2 | 2/2017 | Suedkamp et al. |
| 9,592,129 B2 | 3/2017 | Slivka et al. |
| 9,597,197 B2 | 3/2017 | Lechmann et al. |
| 9,662,223 B2 | 5/2017 | Matthis et al. |
| 9,662,224 B2 | 5/2017 | Weiman et al. |
| 9,675,470 B2 | 6/2017 | Packer et al. |
| 9,724,207 B2 | 8/2017 | Dimauro et al. |
| 9,730,803 B2 | 8/2017 | Dimauro et al. |
| 9,750,552 B2 | 9/2017 | Stephan et al. |
| 9,750,618 B1 * | 9/2017 | Daffinson ............... A61F 2/447 |
| 9,788,962 B2 | 10/2017 | Gabelberger |
| 9,788,963 B2 | 10/2017 | Aquino et al. |
| 9,788,971 B1 | 10/2017 | Stein |
| 9,801,639 B2 | 10/2017 | O'Neil et al. |
| 9,801,640 B2 | 10/2017 | O'Neil et al. |
| 9,801,729 B2 | 10/2017 | Dimauro et al. |
| 9,801,734 B1 | 10/2017 | Stein et al. |
| 9,808,351 B2 | 11/2017 | Kelly et al. |
| 9,808,353 B2 | 11/2017 | Suddaby et al. |
| 9,814,589 B2 | 11/2017 | Dimauro |
| 9,814,590 B2 | 11/2017 | Serhan et al. |
| 9,839,528 B2 | 12/2017 | Weiman et al. |
| 9,839,530 B2 | 12/2017 | Hawkins et al. |
| 9,848,991 B2 | 12/2017 | Boehm et al. |
| 9,872,779 B2 | 1/2018 | Miller et al. |
| 9,907,670 B2 | 3/2018 | Deridder et al. |
| 9,924,978 B2 | 3/2018 | Thommen et al. |
| 9,925,060 B2 | 3/2018 | Dimauro et al. |
| 9,931,223 B2 | 4/2018 | Cain |
| 9,931,226 B2 | 4/2018 | Kurtaliaj et al. |
| 9,937,053 B2 | 4/2018 | Melkent et al. |
| 9,949,769 B2 | 4/2018 | Serhan et al. |
| 9,974,664 B2 | 5/2018 | Emerick et al. |
| 9,980,823 B2 | 5/2018 | Matthis et al. |
| 9,993,350 B2 | 6/2018 | Cain |
| 10,004,607 B2 | 6/2018 | Weiman et al. |
| 10,058,433 B2 | 8/2018 | Lechmann et al. |
| 10,085,843 B2 | 10/2018 | Dimauro |
| 10,092,417 B2 | 10/2018 | Weiman et al. |
| 10,137,009 B2 | 11/2018 | Weiman et al. |
| 10,143,569 B2 | 12/2018 | Weiman et al. |
| 10,219,915 B1 | 3/2019 | Stein |
| 10,238,500 B2 | 3/2019 | Rogers et al. |
| 10,265,191 B2 | 4/2019 | Lim et al. |
| 10,307,254 B2 | 6/2019 | Levy et al. |
| 10,363,142 B2 | 7/2019 | McClintock et al. |
| 10,376,372 B2 | 8/2019 | Serhan et al. |
| 10,398,563 B2 * | 9/2019 | Engstrom ............. A61F 2/4425 |
| 10,398,566 B2 | 9/2019 | Olmos et al. |
| 10,405,986 B2 | 9/2019 | Kelly et al. |
| 10,405,989 B2 | 9/2019 | O'Neil et al. |
| 10,420,651 B2 | 9/2019 | Serhan et al. |
| 10,426,632 B2 | 10/2019 | Butler et al. |
| 10,433,971 B2 | 10/2019 | Dimauro et al. |
| 10,433,974 B2 | 10/2019 | O'Neil |
| 10,433,977 B2 | 10/2019 | Lechmann et al. |
| 10,449,056 B2 | 10/2019 | Cain |
| 10,449,058 B2 | 10/2019 | Lechmann et al. |
| 10,470,894 B2 | 11/2019 | Foley et al. |
| 10,492,918 B2 | 12/2019 | Dimauro |
| 10,492,924 B2 | 12/2019 | Stein et al. |
| 10,512,489 B2 | 12/2019 | Serhan et al. |
| 10,537,436 B2 | 1/2020 | Maguire et al. |
| 10,548,741 B2 | 2/2020 | Suedkamp et al. |
| 10,555,817 B2 | 2/2020 | Dimauro et al. |
| 10,575,959 B2 | 3/2020 | Dimauro et al. |
| 10,583,013 B2 | 3/2020 | Dimauro et al. |
| 10,583,015 B2 | 3/2020 | Olmos et al. |
| 10,639,164 B2 | 5/2020 | Dimauro et al. |
| 10,639,166 B2 | 5/2020 | Weiman et al. |
| 10,682,241 B2 | 6/2020 | Glerum et al. |
| 10,743,914 B2 | 8/2020 | Lopez et al. |
| 10,758,371 B2 | 9/2020 | Hessler et al. |
| 10,842,644 B2 * | 11/2020 | Weiman ................ A61F 2/442 |
| 10,966,840 B2 | 4/2021 | Voellmicke et al. |
| 10,973,652 B2 | 4/2021 | Hawkins et al. |
| 11,051,954 B2 | 7/2021 | Greenhalgh et al. |
| 11,103,362 B2 | 8/2021 | Butler et al. |
| 2001/0011174 A1 | 8/2001 | Reiley et al. |
| 2001/0012950 A1 | 8/2001 | Nishtala et al. |
| 2001/0016741 A1 | 8/2001 | Burkus et al. |
| 2001/0016775 A1 | 8/2001 | Scarborough et al. |
| 2001/0027320 A1 | 10/2001 | Sasso |
| 2001/0037126 A1 | 11/2001 | Stack et al. |
| 2001/0039452 A1 | 11/2001 | Zuckerman et al. |
| 2001/0039453 A1 | 11/2001 | Gresser et al. |
| 2001/0049529 A1 | 12/2001 | Cachia et al. |
| 2001/0049530 A1 | 12/2001 | Culbert et al. |
| 2001/0049531 A1 | 12/2001 | Reiley et al. |
| 2001/0056302 A1 | 12/2001 | Boyer et al. |
| 2002/0001476 A1 | 1/2002 | Nagamine et al. |
| 2002/0010070 A1 | 1/2002 | Cales et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045904 A1 | 4/2002 | Fuss et al. |
| 2002/0045942 A1 | 4/2002 | Ham |
| 2002/0055740 A1 | 5/2002 | Lieberman |
| 2002/0055781 A1 | 5/2002 | Sazy |
| 2002/0058947 A1 | 5/2002 | Hochschuler et al. |
| 2002/0068974 A1 | 6/2002 | Kuslich et al. |
| 2002/0068976 A1 | 6/2002 | Jackson |
| 2002/0068977 A1 | 6/2002 | Jackson |
| 2002/0072801 A1 | 6/2002 | Michelson |
| 2002/0077700 A1 | 6/2002 | Varga et al. |
| 2002/0077701 A1 | 6/2002 | Kuslich |
| 2002/0082584 A1 | 6/2002 | Rosenman et al. |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0091387 A1 | 7/2002 | Hoogland |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0128713 A1 | 9/2002 | Ferree |
| 2002/0128715 A1 | 9/2002 | Bryan et al. |
| 2002/0128716 A1 | 9/2002 | Cohen et al. |
| 2002/0138078 A1 | 9/2002 | Chappuis |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |
| 2002/0151976 A1 | 10/2002 | Foley et al. |
| 2002/0156482 A1 | 10/2002 | Scribner et al. |
| 2002/0161444 A1 | 10/2002 | Choi |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | Mckay |
| 2002/0183761 A1 | 12/2002 | Johnson et al. |
| 2002/0183778 A1 | 12/2002 | Reiley et al. |
| 2002/0183848 A1 | 12/2002 | Ray et al. |
| 2002/0191487 A1 | 12/2002 | Sand |

(56) References Cited

U.S. PATENT DOCUMENTS

| | | |
|---|---|---|
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014113 A1 | 1/2003 | Ralph et al. |
| 2003/0014116 A1 | 1/2003 | Ralph et al. |
| 2003/0018390 A1 | 1/2003 | Husson |
| 2003/0023305 A1 | 1/2003 | Mckay |
| 2003/0028250 A1 | 2/2003 | Reiley et al. |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0045939 A1 | 3/2003 | Casutt |
| 2003/0050644 A1 | 3/2003 | Boucher et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0069582 A1 | 4/2003 | Culbert |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074075 A1 | 4/2003 | Thomas et al. |
| 2003/0078667 A1 | 4/2003 | Manasas et al. |
| 2003/0083642 A1 | 5/2003 | Boyd et al. |
| 2003/0083688 A1 | 5/2003 | Simonson |
| 2003/0108588 A1 | 6/2003 | Chen et al. |
| 2003/0130664 A1 | 7/2003 | Boucher et al. |
| 2003/0130739 A1 | 7/2003 | Gerbec et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0153874 A1 | 8/2003 | Tal |
| 2003/0171812 A1 | 9/2003 | Grunberg et al. |
| 2003/0187431 A1 | 10/2003 | Simonson |
| 2003/0187445 A1 | 10/2003 | Keith et al. |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0191531 A1 | 10/2003 | Berry et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin |
| 2003/0204261 A1 | 10/2003 | Eisermann et al. |
| 2003/0208122 A1 | 11/2003 | Melkent et al. |
| 2003/0208136 A1 | 11/2003 | Mark et al. |
| 2003/0208220 A1 | 11/2003 | Worley et al. |
| 2003/0208270 A9 | 11/2003 | Michelson |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0002761 A1 | 1/2004 | Rogers et al. |
| 2004/0006391 A1 | 1/2004 | Reiley |
| 2004/0008949 A1 | 1/2004 | Liu et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0019359 A1 | 1/2004 | Worley et al. |
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034343 A1 | 2/2004 | Gillespie et al. |
| 2004/0034429 A1 | 2/2004 | Lambrecht et al. |
| 2004/0049190 A1 | 3/2004 | Biedermann et al. |
| 2004/0049203 A1 | 3/2004 | Scribner et al. |
| 2004/0049223 A1 | 3/2004 | Nishtala et al. |
| 2004/0049270 A1 | 3/2004 | Gewirtz |
| 2004/0054412 A1 | 3/2004 | Gerbec et al. |
| 2004/0059333 A1 | 3/2004 | Carl et al. |
| 2004/0059337 A1 | 3/2004 | Hanson et al. |
| 2004/0059339 A1 | 3/2004 | Roehm et al. |
| 2004/0059350 A1 | 3/2004 | Gordon et al. |
| 2004/0059418 A1 | 3/2004 | McKay et al. |
| 2004/0064144 A1 | 4/2004 | Johnson et al. |
| 2004/0068269 A1 | 4/2004 | Bonati et al. |
| 2004/0068318 A1 | 4/2004 | Coates et al. |
| 2004/0073308 A1 | 4/2004 | Kuslich et al. |
| 2004/0073310 A1 | 4/2004 | Moumene et al. |
| 2004/0082953 A1 | 4/2004 | Petit |
| 2004/0083000 A1 | 4/2004 | Keller et al. |
| 2004/0087947 A1 | 5/2004 | Lim et al. |
| 2004/0088055 A1 | 5/2004 | Hanson et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0093083 A1 | 5/2004 | Branch et al. |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Loshakove et al. |
| 2004/0098131 A1 | 5/2004 | Bryan et al. |
| 2004/0102774 A1 | 5/2004 | Trieu |
| 2004/0102784 A1 | 5/2004 | Pasquet et al. |
| 2004/0102846 A1 | 5/2004 | Keller et al. |
| 2004/0106925 A1 | 6/2004 | Culbert |
| 2004/0106940 A1 | 6/2004 | Shaolian et al. |
| 2004/0111161 A1 | 6/2004 | Trieu |
| 2004/0116997 A1 | 6/2004 | Taylor et al. |
| 2004/0117019 A1 | 6/2004 | Trieu et al. |
| 2004/0117022 A1 | 6/2004 | Marnay et al. |
| 2004/0127906 A1 | 7/2004 | Culbert et al. |
| 2004/0127990 A1 | 7/2004 | Bartish et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147129 A1 | 7/2004 | Rolfson |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153065 A1 | 8/2004 | Lim |
| 2004/0153115 A1 | 8/2004 | Reiley et al. |
| 2004/0153156 A1 | 8/2004 | Cohen et al. |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0172134 A1 | 9/2004 | Berry |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |

(56) References Cited

U.S. PATENT DOCUMENTS

| | | |
|---|---|---|
| 2004/0193271 A1 | 9/2004 | Fraser et al. |
| 2004/0193277 A1 | 9/2004 | Long et al. |
| 2004/0199162 A1 | 10/2004 | Von et al. |
| 2004/0210231 A1 | 10/2004 | Boucher et al. |
| 2004/0210310 A1 | 10/2004 | Trieu |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0220668 A1 | 11/2004 | Eisermann et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | Dimauro et al. |
| 2004/0243229 A1 | 12/2004 | Vidlund et al. |
| 2004/0243239 A1 | 12/2004 | Taylor |
| 2004/0243241 A1 | 12/2004 | Istephanous et al. |
| 2004/0249377 A1 | 12/2004 | Kaes et al. |
| 2004/0249461 A1 | 12/2004 | Ferree |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254643 A1 | 12/2004 | Jackson |
| 2004/0254644 A1 | 12/2004 | Taylor |
| 2004/0260297 A1 | 12/2004 | Padget et al. |
| 2004/0260300 A1 | 12/2004 | Gorensek et al. |
| 2004/0260397 A1 | 12/2004 | Lambrecht et al. |
| 2004/0266257 A1 | 12/2004 | Ries et al. |
| 2004/0267271 A9 | 12/2004 | Scribner et al. |
| 2004/0267367 A1 | 12/2004 | O'Neil |
| 2005/0004578 A1 | 1/2005 | Lambrecht et al. |
| 2005/0010292 A1 | 1/2005 | Carrasco |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0021041 A1 | 1/2005 | Michelson |
| 2005/0033289 A1 | 2/2005 | Warren et al. |
| 2005/0033295 A1 | 2/2005 | Wisnewski |
| 2005/0033434 A1 | 2/2005 | Berry |
| 2005/0033440 A1 | 2/2005 | Lambrecht et al. |
| 2005/0038431 A1 | 2/2005 | Bartish et al. |
| 2005/0038515 A1 | 2/2005 | Kunzler |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080443 A1 | 4/2005 | Fallin et al. |
| 2005/0080488 A1 | 4/2005 | Schultz |
| 2005/0085912 A1 | 4/2005 | Arnin et al. |
| 2005/0090443 A1 | 4/2005 | Michael John |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0096745 A1 | 5/2005 | Andre et al. |
| 2005/0102202 A1 | 5/2005 | Linden et al. |
| 2005/0107880 A1 | 5/2005 | Shimp et al. |
| 2005/0113916 A1 | 5/2005 | Branch, Jr. |
| 2005/0113917 A1 | 5/2005 | Chae et al. |
| 2005/0113918 A1 | 5/2005 | Messerli et al. |
| 2005/0113919 A1 | 5/2005 | Cragg et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Turri |
| 2005/0119657 A1 | 6/2005 | Goldsmith |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125062 A1 | 6/2005 | Biedermann et al. |
| 2005/0125066 A1 | 6/2005 | McAfee |
| 2005/0130929 A1 | 6/2005 | Boyd |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131406 A1 | 6/2005 | Reiley et al. |
| 2005/0131409 A1 | 6/2005 | Chervitz et al. |
| 2005/0131411 A1 | 6/2005 | Culbert |
| 2005/0131536 A1 | 6/2005 | Eisermann et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | Hoffmann et al. |
| 2005/0137602 A1 | 6/2005 | Assell et al. |
| 2005/0142211 A1 | 6/2005 | Wenz |
| 2005/0143734 A1 | 6/2005 | Cachia et al. |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149030 A1 | 7/2005 | Serhan et al. |
| 2005/0149034 A1 | 7/2005 | Assell et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0165398 A1 | 7/2005 | Reiley |
| 2005/0165406 A1 | 7/2005 | Assell et al. |
| 2005/0165420 A1 | 7/2005 | Cha |
| 2005/0165484 A1 | 7/2005 | Ferree |
| 2005/0165485 A1 | 7/2005 | Trieu |
| 2005/0171539 A1 | 8/2005 | Braun et al. |
| 2005/0171541 A1 | 8/2005 | Boehm et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177173 A1 | 8/2005 | Aebi et al. |
| 2005/0177235 A1 | 8/2005 | Baynham et al. |
| 2005/0177240 A1 | 8/2005 | Blain |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182418 A1 | 8/2005 | Boyd et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0216018 A1 | 9/2005 | Sennett |
| 2005/0216026 A1 | 9/2005 | Culbert |
| 2005/0216081 A1 | 9/2005 | Taylor |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |

(56) References Cited

U.S. PATENT DOCUMENTS

| | | |
|---|---|---|
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251142 A1 | 11/2005 | Hoffmann et al. |
| 2005/0251149 A1 | 11/2005 | Wenz |
| 2005/0251260 A1 | 11/2005 | Gerber et al. |
| 2005/0256525 A1 | 11/2005 | Culbert et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261769 A1 | 11/2005 | Moskowitz et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0273173 A1 | 12/2005 | Gordon et al. |
| 2005/0277938 A1 | 12/2005 | Parsons |
| 2005/0278023 A1 | 12/2005 | Zwirkoski |
| 2005/0278026 A1 | 12/2005 | Gordon et al. |
| 2005/0278027 A1 | 12/2005 | Hyde, Jr. |
| 2005/0278029 A1 | 12/2005 | Trieu |
| 2005/0283238 A1 | 12/2005 | Reiley |
| 2005/0283244 A1 | 12/2005 | Gordon et al. |
| 2005/0287071 A1 | 12/2005 | Wenz |
| 2006/0004326 A1 | 1/2006 | Collins et al. |
| 2006/0004456 A1 | 1/2006 | McKay |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0020284 A1 | 1/2006 | Foley et al. |
| 2006/0022180 A1 | 2/2006 | Selness |
| 2006/0030850 A1 | 2/2006 | Keegan et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0032621 A1 | 2/2006 | Martin et al. |
| 2006/0036241 A1 | 2/2006 | Siegal |
| 2006/0036244 A1 | 2/2006 | Spitler et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036273 A1 | 2/2006 | Siegal |
| 2006/0036323 A1 | 2/2006 | Carl et al. |
| 2006/0036324 A1 | 2/2006 | Sachs et al. |
| 2006/0041258 A1 | 2/2006 | Galea |
| 2006/0041314 A1 | 2/2006 | Millard |
| 2006/0045904 A1 | 3/2006 | Aronson |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0064101 A1 | 3/2006 | Arramon |
| 2006/0064102 A1 | 3/2006 | Ebner |
| 2006/0064171 A1 | 3/2006 | Trieu |
| 2006/0064172 A1 | 3/2006 | Trieu |
| 2006/0069436 A1 | 3/2006 | Sutton et al. |
| 2006/0069439 A1 | 3/2006 | Zucherman et al. |
| 2006/0069440 A1 | 3/2006 | Zucherman et al. |
| 2006/0074429 A1 | 4/2006 | Ralph et al. |
| 2006/0079908 A1 | 4/2006 | Lieberman |
| 2006/0084867 A1 | 4/2006 | Tremblay et al. |
| 2006/0084977 A1 | 4/2006 | Lieberman |
| 2006/0084988 A1 | 4/2006 | Kim |
| 2006/0085002 A1 | 4/2006 | Trieu et al. |
| 2006/0085009 A1 | 4/2006 | Truckai et al. |
| 2006/0085010 A1 | 4/2006 | Lieberman |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100622 A1 | 5/2006 | Jackson |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111715 A1 | 5/2006 | Jackson |
| 2006/0111728 A1 | 5/2006 | Abdou |
| 2006/0111785 A1 | 5/2006 | O'Neil |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0136062 A1 | 6/2006 | Dinello et al. |
| 2006/0136064 A1 | 6/2006 | Sherman |
| 2006/0142759 A1 | 6/2006 | Arnin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149229 A1 | 7/2006 | Kwak et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0149385 A1 | 7/2006 | McKay |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167547 A1 | 7/2006 | Suddaby |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178745 A1 | 8/2006 | Bartish et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0212118 A1 | 9/2006 | Abernathie |
| 2006/0217711 A1 | 9/2006 | Stevens et al. |
| 2006/0229627 A1 | 10/2006 | Hunt et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235423 A1 | 10/2006 | Cantu |
| 2006/0235521 A1 | 10/2006 | Zucherman et al. |
| 2006/0235531 A1 | 10/2006 | Buettner-Janz |
| 2006/0241643 A1 | 10/2006 | Lim et al. |
| 2006/0241663 A1 | 10/2006 | Rice et al. |
| 2006/0241770 A1 | 10/2006 | Rhoda et al. |
| 2006/0247634 A1 | 11/2006 | Warner et al. |
| 2006/0247770 A1 | 11/2006 | Peterman |
| 2006/0247771 A1 | 11/2006 | Peterman et al. |
| 2006/0247781 A1 | 11/2006 | Francis |

(56) References Cited

U.S. PATENT DOCUMENTS

| | | |
|---|---|---|
| 2006/0253120 A1 | 11/2006 | Anderson et al. |
| 2006/0253201 A1 | 11/2006 | McLuen |
| 2006/0254784 A1 | 11/2006 | Hartmann et al. |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010826 A1 | 1/2007 | Rhoda et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0016191 A1 | 1/2007 | Culbert et al. |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055264 A1 | 3/2007 | Parmigiani |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073399 A1 | 3/2007 | Zipnick et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093897 A1 | 4/2007 | Gerbec et al. |
| 2007/0093899 A1 | 4/2007 | Dutoit et al. |
| 2007/0093901 A1 | 4/2007 | Grotz et al. |
| 2007/0093906 A1 | 4/2007 | Hudgins et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0123986 A1 | 5/2007 | Schaller |
| 2007/0129730 A1 | 6/2007 | Woods et al. |
| 2007/0135922 A1 | 6/2007 | Trieu |
| 2007/0142843 A1 | 6/2007 | Dye |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0161992 A1 | 7/2007 | Kwak et al. |
| 2007/0162005 A1 | 7/2007 | Peterson et al. |
| 2007/0162127 A1 | 7/2007 | Peterman et al. |
| 2007/0162132 A1 | 7/2007 | Messerli |
| 2007/0162138 A1 | 7/2007 | Heinz |
| 2007/0167945 A1 | 7/2007 | Lange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0213737 A1 | 9/2007 | Schermerhorn et al. |
| 2007/0213826 A1 | 9/2007 | Smith et al. |
| 2007/0219634 A1 | 9/2007 | Greenhalgh et al. |
| 2007/0225706 A1 | 9/2007 | Clark et al. |
| 2007/0225726 A1 | 9/2007 | Dye et al. |
| 2007/0225807 A1 | 9/2007 | Phan et al. |
| 2007/0225815 A1 | 9/2007 | Keith et al. |
| 2007/0233074 A1 | 10/2007 | Anderson et al. |
| 2007/0233076 A1 | 10/2007 | Trieu |
| 2007/0233083 A1 | 10/2007 | Abdou |
| 2007/0233089 A1 | 10/2007 | Dipoto et al. |
| 2007/0233130 A1 | 10/2007 | Suddaby |
| 2007/0233244 A1 | 10/2007 | Lopez et al. |
| 2007/0233254 A1 | 10/2007 | Grotz et al. |
| 2007/0250167 A1 | 10/2007 | Bray et al. |
| 2007/0260245 A1 | 11/2007 | Malandain et al. |
| 2007/0260255 A1 | 11/2007 | Haddock et al. |
| 2007/0260314 A1 | 11/2007 | Biyani |
| 2007/0270823 A1 | 11/2007 | Trieu et al. |
| 2007/0270954 A1 | 11/2007 | Wu |
| 2007/0270957 A1 | 11/2007 | Heinz |
| 2007/0270968 A1 | 11/2007 | Baynham et al. |
| 2007/0276373 A1 | 11/2007 | Malandain |
| 2007/0276375 A1 | 11/2007 | Rapp |
| 2007/0276497 A1 | 11/2007 | Anderson |
| 2007/0282443 A1 | 12/2007 | Globerman et al. |
| 2007/0282449 A1 | 12/2007 | De et al. |
| 2007/0288091 A1 | 12/2007 | Braddock et al. |
| 2007/0299521 A1 | 12/2007 | Glenn et al. |
| 2008/0009877 A1 | 1/2008 | Sankaran et al. |
| 2008/0015694 A1 | 1/2008 | Tribus |

(56) References Cited

U.S. PATENT DOCUMENTS

| | | |
|---|---|---|
| 2008/0015701 A1 | 1/2008 | Garcia et al. |
| 2008/0021556 A1 | 1/2008 | Edie |
| 2008/0021557 A1 | 1/2008 | Trieu |
| 2008/0021558 A1 | 1/2008 | Thramann |
| 2008/0021559 A1 | 1/2008 | Thramann |
| 2008/0027437 A1 | 1/2008 | Johnson et al. |
| 2008/0027438 A1 | 1/2008 | Abdou |
| 2008/0027453 A1 | 1/2008 | Johnson et al. |
| 2008/0027454 A1 | 1/2008 | Johnson et al. |
| 2008/0027544 A1 | 1/2008 | Melkent |
| 2008/0027550 A1 | 1/2008 | Link et al. |
| 2008/0033440 A1 | 2/2008 | Moskowitz et al. |
| 2008/0045966 A1 | 2/2008 | Buttermann et al. |
| 2008/0051890 A1 | 2/2008 | Waugh et al. |
| 2008/0051897 A1 | 2/2008 | Lopez et al. |
| 2008/0051902 A1 | 2/2008 | Dwyer |
| 2008/0058598 A1 | 3/2008 | Ries et al. |
| 2008/0058937 A1 | 3/2008 | Malandain et al. |
| 2008/0058944 A1 | 3/2008 | Duplessis et al. |
| 2008/0065082 A1 | 3/2008 | Chang et al. |
| 2008/0065219 A1 | 3/2008 | Dye |
| 2008/0071356 A1 | 3/2008 | Greenhalgh et al. |
| 2008/0071380 A1 | 3/2008 | Sweeney |
| 2008/0077148 A1 | 3/2008 | Ries et al. |
| 2008/0077150 A1 | 3/2008 | Nguyen |
| 2008/0077241 A1 | 3/2008 | Nguyen |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0097454 A1 | 4/2008 | Deridder et al. |
| 2008/0097611 A1 | 4/2008 | Mastrorio et al. |
| 2008/0103601 A1 | 5/2008 | Biro et al. |
| 2008/0108990 A1 | 5/2008 | Mitchell et al. |
| 2008/0108996 A1 | 5/2008 | Padget et al. |
| 2008/0119935 A1 | 5/2008 | Alvarez |
| 2008/0125865 A1 | 5/2008 | Abdelgany |
| 2008/0132934 A1 | 6/2008 | Reiley et al. |
| 2008/0133012 A1 | 6/2008 | McGuckin |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147129 A1 | 6/2008 | Biedermann et al. |
| 2008/0147193 A1 | 6/2008 | Matthis et al. |
| 2008/0154377 A1 | 6/2008 | Voellmicke |
| 2008/0154379 A1 | 6/2008 | Steiner et al. |
| 2008/0161927 A1 | 7/2008 | Savage et al. |
| 2008/0167657 A1 | 7/2008 | Greenhalgh |
| 2008/0172128 A1 | 7/2008 | Perez-Cruet et al. |
| 2008/0177306 A1 | 7/2008 | Lamborne et al. |
| 2008/0177312 A1 | 7/2008 | Perez-Cruet et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195209 A1 | 8/2008 | Garcia et al. |
| 2008/0195210 A1 | 8/2008 | Milijasevic et al. |
| 2008/0208255 A1 | 8/2008 | Siegal |
| 2008/0208344 A1 | 8/2008 | Kilpela et al. |
| 2008/0221586 A1 | 9/2008 | Garcia-Bengochea et al. |
| 2008/0221687 A1 | 9/2008 | Viker |
| 2008/0228225 A1 | 9/2008 | Trautwein et al. |
| 2008/0229597 A1 | 9/2008 | Malandain |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243251 A1 | 10/2008 | Stad et al. |
| 2008/0243254 A1 | 10/2008 | Butler |
| 2008/0249622 A1 | 10/2008 | Gray |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2008/0312743 A1 | 12/2008 | Vila et al. |
| 2008/0319477 A1 | 12/2008 | Justis et al. |
| 2009/0005870 A1 | 1/2009 | Hawkins et al. |
| 2009/0005873 A1 | 1/2009 | Slivka et al. |
| 2009/0018524 A1 | 1/2009 | Greenhalgh et al. |
| 2009/0030423 A1 | 1/2009 | Puno |
| 2009/0048631 A1 | 2/2009 | Bhatnagar et al. |
| 2009/0048678 A1 | 2/2009 | Saal et al. |
| 2009/0054898 A1 | 2/2009 | Gleason |
| 2009/0054911 A1 | 2/2009 | Mueller et al. |
| 2009/0054988 A1 | 2/2009 | Hess |
| 2009/0054991 A1 | 2/2009 | Biyani et al. |
| 2009/0062807 A1 | 3/2009 | Song |
| 2009/0069813 A1 | 3/2009 | Von et al. |
| 2009/0069895 A1 | 3/2009 | Gittings et al. |
| 2009/0076607 A1 | 3/2009 | Aalsma et al. |
| 2009/0076610 A1 | 3/2009 | Afzal |
| 2009/0088789 A1 | 4/2009 | O'Neil et al. |
| 2009/0099568 A1 | 4/2009 | Lowry et al. |
| 2009/0105712 A1 | 4/2009 | Dauster et al. |
| 2009/0105745 A1 | 4/2009 | Culbert |
| 2009/0112217 A1 | 4/2009 | Hester |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0143859 A1 | 6/2009 | McClellan et al. |
| 2009/0149857 A1 | 6/2009 | Culbert et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0182429 A1 | 7/2009 | Humphreys et al. |
| 2009/0192613 A1 | 7/2009 | Wing et al. |
| 2009/0192614 A1 | 7/2009 | Beger et al. |
| 2009/0216234 A1 | 8/2009 | Farr et al. |
| 2009/0221967 A1 | 9/2009 | Thommen et al. |
| 2009/0222043 A1 | 9/2009 | Altarac et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234364 A1 | 9/2009 | Crook |
| 2009/0234389 A1 | 9/2009 | Chuang et al. |
| 2009/0234398 A1 | 9/2009 | Chirico et al. |
| 2009/0240333 A1 | 9/2009 | Trudeau et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0275890 A1 | 11/2009 | Leibowitz et al. |
| 2009/0276049 A1 | 11/2009 | Weiland |
| 2009/0276051 A1 | 11/2009 | Arramon et al. |
| 2009/0292361 A1 | 11/2009 | Lopez |
| 2009/0299479 A1 | 12/2009 | Jones et al. |
| 2010/0016905 A1 | 1/2010 | Greenhalgh et al. |
| 2010/0016968 A1 | 1/2010 | Moore |
| 2010/0030217 A1 | 2/2010 | Mitusina |
| 2010/0040332 A1 | 2/2010 | Van et al. |
| 2010/0042218 A1 | 2/2010 | Nebosky et al. |
| 2010/0049324 A1 | 2/2010 | Valdevit et al. |
| 2010/0070036 A1 | 3/2010 | Implicito |
| 2010/0076492 A1 | 3/2010 | Warner et al. |
| 2010/0076502 A1 | 3/2010 | Guyer et al. |
| 2010/0076559 A1 | 3/2010 | Bagga et al. |
| 2010/0082109 A1 | 4/2010 | Greenhalgh et al. |
| 2010/0094422 A1 | 4/2010 | Hansell et al. |
| 2010/0094424 A1 | 4/2010 | Woodburn et al. |
| 2010/0094426 A1 | 4/2010 | Grohowski et al. |
| 2010/0100098 A1 | 4/2010 | Norton et al. |
| 2010/0100183 A1 | 4/2010 | Prewett et al. |
| 2010/0106191 A1 | 4/2010 | Yue et al. |
| 2010/0114105 A1 | 5/2010 | Butters et al. |
| 2010/0114147 A1 | 5/2010 | Biyani |
| 2010/0125334 A1 | 5/2010 | Krueger |
| 2010/0161060 A1 | 6/2010 | Schaller et al. |

(56) References Cited

U.S. PATENT DOCUMENTS

| | | |
|---|---|---|
| 2010/0174314 A1 | 7/2010 | Mirkovic et al. |
| 2010/0179594 A1 | 7/2010 | Theofilos et al. |
| 2010/0185290 A1 | 7/2010 | Compton et al. |
| 2010/0185292 A1 | 7/2010 | Hochschuler et al. |
| 2010/0191241 A1 | 7/2010 | McCormack et al. |
| 2010/0191334 A1 | 7/2010 | Keller |
| 2010/0191336 A1 | 7/2010 | Greenhalgh |
| 2010/0204795 A1 | 8/2010 | Greenhalgh |
| 2010/0204796 A1 | 8/2010 | Bae et al. |
| 2010/0211107 A1 | 8/2010 | Muhanna |
| 2010/0211176 A1 | 8/2010 | Greenhalgh |
| 2010/0211182 A1 | 8/2010 | Zimmermann |
| 2010/0217269 A1 | 8/2010 | Landes |
| 2010/0222884 A1 | 9/2010 | Greenhalgh |
| 2010/0234849 A1 | 9/2010 | Bouadi |
| 2010/0234956 A1 | 9/2010 | Attia et al. |
| 2010/0241231 A1 | 9/2010 | Marino et al. |
| 2010/0249935 A1 | 9/2010 | Slivka et al. |
| 2010/0256768 A1 | 10/2010 | Lim et al. |
| 2010/0262240 A1 | 10/2010 | Chavatte et al. |
| 2010/0268231 A1 | 10/2010 | Kuslich et al. |
| 2010/0268338 A1 | 10/2010 | Melkent et al. |
| 2010/0274358 A1 | 10/2010 | Mueller et al. |
| 2010/0286777 A1 | 11/2010 | Errico et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0305700 A1 | 12/2010 | Ben-Arye et al. |
| 2010/0305704 A1 | 12/2010 | Messerli et al. |
| 2010/0324607 A1 | 12/2010 | Davis |
| 2010/0324683 A1 | 12/2010 | Reichen et al. |
| 2010/0331845 A1 | 12/2010 | Foley et al. |
| 2010/0331891 A1 | 12/2010 | Culbert et al. |
| 2011/0004216 A1 | 1/2011 | Amendola et al. |
| 2011/0004308 A1 | 1/2011 | Marino et al. |
| 2011/0004310 A1 | 1/2011 | Michelson |
| 2011/0009970 A1 | 1/2011 | Puno |
| 2011/0015747 A1 | 1/2011 | Mcmanus et al. |
| 2011/0029082 A1 | 2/2011 | Hall |
| 2011/0029083 A1 | 2/2011 | Hynes et al. |
| 2011/0029085 A1 | 2/2011 | Hynes et al. |
| 2011/0029086 A1 | 2/2011 | Glazer et al. |
| 2011/0035011 A1 | 2/2011 | Cain |
| 2011/0040332 A1 | 2/2011 | Culbert et al. |
| 2011/0046674 A1 | 2/2011 | Calvosa et al. |
| 2011/0054538 A1 | 3/2011 | Zehavi et al. |
| 2011/0066186 A1 | 3/2011 | Boyer et al. |
| 2011/0071527 A1 | 3/2011 | Nelson et al. |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0098531 A1 | 4/2011 | To |
| 2011/0098628 A1 | 4/2011 | Yeung et al. |
| 2011/0098818 A1 | 4/2011 | Brodke et al. |
| 2011/0112586 A1 | 5/2011 | Guyer et al. |
| 2011/0130835 A1 | 6/2011 | Ashley et al. |
| 2011/0130838 A1 | 6/2011 | Morgenstern Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160773 A1 | 6/2011 | Aschmann et al. |
| 2011/0160866 A1 | 6/2011 | Laurence et al. |
| 2011/0172716 A1 | 7/2011 | Glerum |
| 2011/0172774 A1 | 7/2011 | Varela |
| 2011/0190816 A1 | 8/2011 | Sheffer et al. |
| 2011/0190891 A1 | 8/2011 | Suh et al. |
| 2011/0230971 A1 | 9/2011 | Donner et al. |
| 2011/0238072 A1 | 9/2011 | Tyndall |
| 2011/0251690 A1 | 10/2011 | Berger et al. |
| 2011/0270261 A1 | 11/2011 | Mast et al. |
| 2011/0270401 A1 | 11/2011 | Mckay |
| 2011/0276142 A1 | 11/2011 | Niemiec et al. |
| 2011/0282453 A1 | 11/2011 | Greenhalgh et al. |
| 2011/0282459 A1 | 11/2011 | McClellan et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2011/0319899 A1 | 12/2011 | O'Neil et al. |
| 2011/0319998 A1 | 12/2011 | O'Neil et al. |
| 2011/0320000 A1 | 12/2011 | O'Neil |
| 2012/0004726 A1 | 1/2012 | Greenhalgh et al. |
| 2012/0004732 A1 | 1/2012 | Goel et al. |
| 2012/0006361 A1 | 1/2012 | Miyagi et al. |
| 2012/0010715 A1 | 1/2012 | Spann |
| 2012/0022654 A1 | 1/2012 | Farris et al. |
| 2012/0029636 A1 | 2/2012 | Ragab et al. |
| 2012/0029639 A1 | 2/2012 | Blackwell et al. |
| 2012/0035730 A1 | 2/2012 | Spann |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083887 A1 | 4/2012 | Purcell et al. |
| 2012/0083889 A1 | 4/2012 | Purcell et al. |
| 2012/0109319 A1 | 5/2012 | Perisic |
| 2012/0123546 A1 | 5/2012 | Medina |
| 2012/0136443 A1 | 5/2012 | Wenzel |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0191204 A1 | 7/2012 | Bae et al. |
| 2012/0197299 A1 | 8/2012 | Fabian, Jr. |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0209383 A1 | 8/2012 | Tsuang et al. |
| 2012/0215262 A1 | 8/2012 | Culbert et al. |
| 2012/0215315 A1 | 8/2012 | Hochschuler et al. |
| 2012/0215316 A1 | 8/2012 | Mohr et al. |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0253395 A1 | 10/2012 | Linares |
| 2012/0253406 A1 | 10/2012 | Bae et al. |
| 2012/0265309 A1 | 10/2012 | Glerum et al. |
| 2012/0277795 A1 | 11/2012 | Von et al. |
| 2012/0277869 A1 | 11/2012 | Siccardi et al. |
| 2012/0277877 A1 | 11/2012 | Smith et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | Dimauro et al. |
| 2012/0323327 A1 | 12/2012 | Mcafee |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0006362 A1 | 1/2013 | Biedermann et al. |
| 2013/0023937 A1 | 1/2013 | Biedermann et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0030544 A1 | 1/2013 | Studer |
| 2013/0053966 A1 | 2/2013 | Jimenez et al. |
| 2013/0060337 A1 | 3/2013 | Peiersheim et al. |
| 2013/0073044 A1 | 3/2013 | Gamache |
| 2013/0079790 A1 | 3/2013 | Stein et al. |
| 2013/0085572 A1 | 4/2013 | Glerum et al. |
| 2013/0085574 A1 | 4/2013 | Sledge |
| 2013/0109925 A1 | 5/2013 | Horton et al. |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0144391 A1 | 6/2013 | Siegal et al. |

(56) References Cited

U.S. PATENT DOCUMENTS

| | | |
|---|---|---|
| 2013/0150906 A1 | 6/2013 | Kerboul et al. |
| 2013/0158663 A1 | 6/2013 | Miller et al. |
| 2013/0158664 A1* | 6/2013 | Palmatier ............... A61F 2/447 623/17.16 |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0197647 A1 | 8/2013 | Wolters et al. |
| 2013/0204371 A1 | 8/2013 | Mcluen et al. |
| 2013/0211525 A1 | 8/2013 | Mcluen et al. |
| 2013/0211526 A1 | 8/2013 | Alheidt et al. |
| 2013/0218276 A1 | 8/2013 | Fiechter et al. |
| 2013/0231747 A1 | 9/2013 | Olmos et al. |
| 2013/0238006 A1 | 9/2013 | O'Neil et al. |
| 2013/0253585 A1 | 9/2013 | Garcia et al. |
| 2013/0261746 A1 | 10/2013 | Linares et al. |
| 2013/0261747 A1 | 10/2013 | Geisert |
| 2013/0268077 A1 | 10/2013 | You et al. |
| 2013/0274883 A1 | 10/2013 | McLuen et al. |
| 2013/0310937 A1 | 11/2013 | Luiz |
| 2013/0310939 A1 | 11/2013 | Fabian et al. |
| 2013/0325128 A1 | 12/2013 | Perloff et al. |
| 2014/0018816 A1 | 1/2014 | Fenn et al. |
| 2014/0025169 A1 | 1/2014 | Lechmann et al. |
| 2014/0039622 A1 | 2/2014 | Glerum et al. |
| 2014/0039626 A1 | 2/2014 | Mitchell |
| 2014/0046333 A1 | 2/2014 | Johnson et al. |
| 2014/0046446 A1 | 2/2014 | Robinson |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0067073 A1 | 3/2014 | Hauck |
| 2014/0081267 A1 | 3/2014 | Orsak et al. |
| 2014/0086962 A1 | 3/2014 | Jin et al. |
| 2014/0094916 A1 | 4/2014 | Glerum et al. |
| 2014/0094917 A1 | 4/2014 | Salerni |
| 2014/0100662 A1 | 4/2014 | Patterson |
| 2014/0107790 A1 | 4/2014 | Combrowski |
| 2014/0114414 A1 | 4/2014 | Abdou et al. |
| 2014/0114423 A1 | 4/2014 | Suedkamp et al. |
| 2014/0121774 A1 | 5/2014 | Glerum et al. |
| 2014/0128977 A1 | 5/2014 | Glerum et al. |
| 2014/0128980 A1 | 5/2014 | Louis |
| 2014/0135934 A1 | 5/2014 | Hansell et al. |
| 2014/0142706 A1 | 5/2014 | Hansell et al. |
| 2014/0148904 A1 | 5/2014 | Robinson |
| 2014/0163682 A1 | 6/2014 | Lott |
| 2014/0163683 A1 | 6/2014 | Seifert et al. |
| 2014/0172103 A1 | 6/2014 | O'Neil et al. |
| 2014/0172105 A1 | 6/2014 | Frasier et al. |
| 2014/0172106 A1 | 6/2014 | To et al. |
| 2014/0180421 A1 | 6/2014 | Glerum et al. |
| 2014/0188225 A1 | 7/2014 | Klaus |
| 2014/0228959 A1 | 8/2014 | Niemiec et al. |
| 2014/0236296 A1 | 8/2014 | Wagner et al. |
| 2014/0243892 A1 | 8/2014 | Choinski |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277139 A1 | 9/2014 | Vrionis et al. |
| 2014/0277204 A1 | 9/2014 | Sandhu |
| 2014/0277464 A1 | 9/2014 | Richter et al. |
| 2014/0277473 A1 | 9/2014 | Perrow |
| 2014/0277474 A1 | 9/2014 | Robinson et al. |
| 2014/0277476 A1 | 9/2014 | Mclean et al. |
| 2014/0277481 A1 | 9/2014 | Lee et al. |
| 2014/0277507 A1 | 9/2014 | Baynham |
| 2014/0296983 A1 | 10/2014 | Fauth et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2014/0336764 A1 | 11/2014 | Masson et al. |
| 2014/0343678 A1 | 11/2014 | Suddaby et al. |
| 2015/0012097 A1 | 1/2015 | Ibarra et al. |
| 2015/0012098 A1 | 1/2015 | Eastlack et al. |
| 2015/0045894 A1 | 2/2015 | Hawkins et al. |
| 2015/0057755 A1 | 2/2015 | Suddaby et al. |
| 2015/0066145 A1 | 3/2015 | Rogers et al. |
| 2015/0088256 A1 | 3/2015 | Ballard |
| 2015/0094610 A1 | 4/2015 | Morgenstern et al. |
| 2015/0094812 A1 | 4/2015 | Cain |
| 2015/0094813 A1 | 4/2015 | Lechmann et al. |
| 2015/0094814 A1 | 4/2015 | Emerick et al. |
| 2015/0100128 A1 | 4/2015 | Glerum et al. |
| 2015/0112398 A1 | 4/2015 | Morgenstern et al. |
| 2015/0112437 A1 | 4/2015 | Davis et al. |
| 2015/0112438 A1 | 4/2015 | Mclean |
| 2015/0157470 A1 | 6/2015 | Voellmicke et al. |
| 2015/0164655 A1 | 6/2015 | Dimauro |
| 2015/0173914 A1 | 6/2015 | Dimauro et al. |
| 2015/0173916 A1 | 6/2015 | Cain |
| 2015/0182347 A1 | 7/2015 | Robinson |
| 2015/0190242 A1 | 7/2015 | Blain et al. |
| 2015/0196400 A1 | 7/2015 | Dace |
| 2015/0196401 A1 | 7/2015 | Dimauro et al. |
| 2015/0202052 A1 | 7/2015 | Dimauro |
| 2015/0216671 A1 | 8/2015 | Cain |
| 2015/0216672 A1 | 8/2015 | Cain |
| 2015/0216673 A1 | 8/2015 | Dimauro |
| 2015/0230929 A1 | 8/2015 | Lorio |
| 2015/0230932 A1 | 8/2015 | Schaller |
| 2015/0238324 A1 | 8/2015 | Nebosky et al. |
| 2015/0250606 A1 | 9/2015 | Mclean |
| 2015/0272743 A1 | 10/2015 | Jimenez et al. |
| 2015/0305881 A1 | 10/2015 | Bal et al. |
| 2015/0320571 A1 | 11/2015 | Lechmann et al. |
| 2016/0000577 A1 | 1/2016 | Dimauro |
| 2016/0016309 A1 | 1/2016 | Swift et al. |
| 2016/0022437 A1 | 1/2016 | Kelly et al. |
| 2016/0022438 A1 | 1/2016 | Lamborne et al. |
| 2016/0038301 A1 | 2/2016 | Wickham |
| 2016/0038304 A1 | 2/2016 | Aquino et al. |
| 2016/0045333 A1 | 2/2016 | Baynham |
| 2016/0051373 A1 | 2/2016 | Faulhaber |
| 2016/0051374 A1 | 2/2016 | Faulhaber |
| 2016/0051376 A1 | 2/2016 | Serhan et al. |
| 2016/0058573 A1 | 3/2016 | Dimauro et al. |
| 2016/0067055 A1 | 3/2016 | Hawkins et al. |
| 2016/0074170 A1 | 3/2016 | Rogers et al. |
| 2016/0074175 A1 | 3/2016 | O'Neil |
| 2016/0081814 A1 | 3/2016 | Baynham |
| 2016/0089247 A1 | 3/2016 | Nichols et al. |
| 2016/0100954 A1 | 4/2016 | Rumi et al. |
| 2016/0106551 A1 | 4/2016 | Grimberg et al. |
| 2016/0113776 A1 | 4/2016 | Capote |
| 2016/0120662 A1 | 5/2016 | Schaller |
| 2016/0128843 A1 | 5/2016 | Tsau et al. |
| 2016/0199195 A1 | 7/2016 | Hauck et al. |
| 2016/0199196 A1 | 7/2016 | Serhan et al. |
| 2016/0228258 A1 | 8/2016 | Schaller et al. |
| 2016/0235455 A1 | 8/2016 | Wahl |
| 2016/0242929 A1 | 8/2016 | Voellmicke et al. |
| 2016/0256291 A1 | 9/2016 | Miller |
| 2016/0296342 A1 | 10/2016 | Woods |
| 2016/0310296 A1 | 10/2016 | Dimauro et al. |
| 2016/0317313 A1 | 11/2016 | Dimauro |
| 2016/0317317 A1 | 11/2016 | Marchek et al. |
| 2016/0317714 A1 | 11/2016 | Dimauro et al. |
| 2016/0331541 A1 | 11/2016 | Dimauro et al. |
| 2016/0331546 A1 | 11/2016 | Lechmann et al. |
| 2016/0331548 A1 | 11/2016 | Dimauro et al. |
| 2016/0338854 A1 | 11/2016 | Serhan et al. |
| 2016/0367265 A1 | 12/2016 | Morgenstern Lopez |
| 2016/0367380 A1 | 12/2016 | Dimauro |
| 2016/0374821 A1 | 12/2016 | Dimauro et al. |
| 2017/0000622 A1 | 1/2017 | Thommen et al. |

(56) References Cited

U.S. PATENT DOCUMENTS

| | | |
|---|---|---|
| 2017/0035578 A1 | 2/2017 | Dimauro et al. |
| 2017/0056179 A1 | 3/2017 | Lorio |
| 2017/0065427 A1 | 3/2017 | Songer |
| 2017/0071756 A1 | 3/2017 | Slivka et al. |
| 2017/0100177 A1 | 4/2017 | Kim |
| 2017/0100255 A1 | 4/2017 | Hleihil et al. |
| 2017/0100260 A1 | 4/2017 | Duffield et al. |
| 2017/0119542 A1 | 5/2017 | Logan et al. |
| 2017/0128226 A1 | 5/2017 | Faulhaber |
| 2017/0209284 A1 | 7/2017 | Overes et al. |
| 2017/0216045 A1 | 8/2017 | Dewey et al. |
| 2017/0266015 A1 | 9/2017 | Overes et al. |
| 2017/0290674 A1 | 10/2017 | Olmos et al. |
| 2017/0290675 A1 | 10/2017 | Olmos et al. |
| 2017/0290677 A1 | 10/2017 | Olmos et al. |
| 2017/0296352 A1 | 10/2017 | Richerme et al. |
| 2017/0304074 A1 | 10/2017 | Dimauro et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0028200 A1 | 2/2018 | O'Neil et al. |
| 2018/0036141 A1 | 2/2018 | Oneil et al. |
| 2018/0055649 A1 | 3/2018 | Kelly et al. |
| 2018/0071111 A1 | 3/2018 | Sharifi-Mehr et al. |
| 2018/0078379 A1 | 3/2018 | Serhan et al. |
| 2018/0116811 A1 | 5/2018 | Bernard et al. |
| 2018/0161171 A1 | 6/2018 | Frasier et al. |
| 2018/0161175 A1 | 6/2018 | Frasier et al. |
| 2018/0193164 A1 | 7/2018 | Shoshtaev |
| 2018/0256360 A1 | 9/2018 | Cain |
| 2018/0256362 A1 | 9/2018 | Slivka et al. |
| 2019/0008654 A1 | 1/2019 | Thommen |
| 2019/0083276 A1 | 3/2019 | Dimauro |
| 2019/0105171 A1 | 4/2019 | Rogers et al. |
| 2019/0117409 A1 | 4/2019 | Shoshtaev |
| 2019/0133785 A1 | 5/2019 | Georges |
| 2019/0142602 A1 | 5/2019 | Olmos et al. |
| 2019/0269522 A1 | 9/2019 | Pavento et al. |
| 2019/0388238 A1 | 12/2019 | Lechmann et al. |
| 2020/0008950 A1 | 1/2020 | Serhan et al. |
| 2020/0015982 A1 | 1/2020 | O'Neil |
| 2020/0030114 A1 | 1/2020 | Cain |
| 2020/0060843 A1 | 2/2020 | Evans et al. |
| 2020/0078192 A1 | 3/2020 | Marchek et al. |
| 2020/0121473 A1 | 4/2020 | Gamache et al. |
| 2020/0129308 A1 | 4/2020 | Suedkamp et al. |
| 2020/0297506 A1 | 9/2020 | Olmos et al. |
| 2020/0375754 A1 | 12/2020 | Cain |
| 2020/0375755 A1 | 12/2020 | Cain |
| 2020/0383799 A1 | 12/2020 | Cain |
| 2020/0405497 A1 | 12/2020 | Olmos et al. |
| 2020/0405500 A1 | 12/2020 | Cain |
| 2021/0000160 A1 | 1/2021 | Olmos et al. |
| 2021/0177619 A1 | 6/2021 | Voellmicke et al. |
| 2021/0353427 A1 | 11/2021 | Butler et al. |

FOREIGN PATENT DOCUMENTS

| | | |
|---|---|---|
| CA | 2617872 A1 | 2/2007 |
| CN | 1177918 A | 4/1998 |
| CN | 1383790 A | 12/2002 |
| CN | 1819805 A | 8/2006 |
| CN | 101031260 A | 9/2007 |
| CN | 101087566 A | 12/2007 |
| CN | 101185594 A | 5/2008 |
| CN | 101631516 A | 1/2010 |
| CN | 101909548 A | 12/2010 |
| CN | 101951847 A | 1/2011 |
| CN | 102164552 A | 8/2011 |
| CN | 103620249 A | 3/2014 |
| CN | 104023674 A | 9/2014 |
| CN | 104023675 A | 9/2014 |
| CN | 104042366 A | 9/2014 |
| CN | 104822332 A | 8/2015 |
| CN | 104921848 A | 9/2015 |
| CN | 104939876 A | 9/2015 |
| CN | 105025846 A | 11/2015 |
| CN | 105188582 A | 12/2015 |
| CN | 204971722 U | 1/2016 |
| CN | 105769391 A | 7/2016 |
| CN | 105769392 A | 7/2016 |
| CN | 107205829 A | 9/2017 |
| DE | 2804936 A1 | 8/1979 |
| DE | 3023353 A1 | 4/1981 |
| DE | 3801459 A1 | 8/1989 |
| DE | 3911610 A1 | 10/1990 |
| DE | 4012622 C1 | 7/1991 |
| DE | 9407806 U1 | 7/1994 |
| DE | 19710392 C1 | 7/1999 |
| DE | 19832798 C1 | 11/1999 |
| DE | 20101793 U1 | 5/2001 |
| DE | 202006005868 U1 | 6/2006 |
| DE | 202008001079 U1 | 3/2008 |
| DE | 10357960 B4 | 9/2015 |
| EP | 0077159 A1 | 4/1983 |
| EP | 0260044 A1 | 3/1988 |
| EP | 0270704 A1 | 6/1988 |
| EP | 0282161 A1 | 9/1988 |
| EP | 0433717 A1 | 6/1991 |
| EP | 0509084 A1 | 10/1992 |
| EP | 0525352 A1 | 2/1993 |
| EP | 0529275 A2 | 3/1993 |
| EP | 0609084 A2 | 8/1994 |
| EP | 0611557 A2 | 8/1994 |
| EP | 0621020 A1 | 10/1994 |
| EP | 0625336 A2 | 11/1994 |
| EP | 0678489 A1 | 10/1995 |
| EP | 0743045 A2 | 11/1996 |
| EP | 0853929 A2 | 7/1998 |
| EP | 1046376 A1 | 10/2000 |
| EP | 1157676 A1 | 11/2001 |
| EP | 1283026 A2 | 2/2003 |
| EP | 1290985 A2 | 3/2003 |
| EP | 1308132 A2 | 5/2003 |
| EP | 1374784 A1 | 1/2004 |
| EP | 1378205 A1 | 1/2004 |
| EP | 1405602 A1 | 4/2004 |
| EP | 1532949 A1 | 5/2005 |
| EP | 1541096 A1 | 6/2005 |
| EP | 1605836 A1 | 12/2005 |
| EP | 1385449 B1 | 7/2006 |
| EP | 1683593 A2 | 7/2006 |
| EP | 1698305 A1 | 9/2006 |
| EP | 1829486 A1 | 9/2007 |
| EP | 1843723 A1 | 10/2007 |
| EP | 1845874 A1 | 10/2007 |
| EP | 1924227 A2 | 5/2008 |
| EP | 1925272 | 5/2008 |
| EP | 2331023 A2 | 6/2011 |
| EP | 2368529 A1 | 9/2011 |
| EP | 2237748 B1 | 9/2012 |
| EP | 2641571 A1 | 9/2013 |
| EP | 2705809 A1 | 3/2014 |
| EP | 2764851 A1 | 8/2014 |
| EP | 2777633 | 9/2014 |
| EP | 2645965 B1 | 8/2016 |
| EP | 3263072 A1 | 1/2018 |
| EP | 3366263 A1 | 8/2018 |
| FR | 2649311 A1 | 1/1991 |
| FR | 2699065 A1 | 6/1994 |
| FR | 2712486 A1 | 5/1995 |
| FR | 2718635 A1 | 10/1995 |
| FR | 2728778 A1 | 7/1996 |
| FR | 2730159 A1 | 8/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 A1 | 3/2006 |
| FR | 2913331 A1 | 9/2008 |
| FR | 2948277 | 1/2011 |
| FR | 3026294 | 4/2016 |
| GB | 2157788 A | 10/1985 |
| GB | 2173565 A | 10/1986 |

(56) References Cited

FOREIGN PATENT DOCUMENTS

| | | |
|---|---|---|
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 07-213533 A | 8/1995 |
| JP | 10-085232 A | 4/1998 |
| JP | 11-089854 A | 4/1999 |
| JP | 2003-010197 A | 1/2003 |
| JP | 2003-126266 A | 5/2003 |
| JP | 2003-526457 A | 9/2003 |
| JP | 2006-501901 A | 1/2006 |
| JP | 2006-516456 | 7/2006 |
| JP | 2007-054666 A | 3/2007 |
| JP | 2007-530243 A | 11/2007 |
| JP | 2008-507363 A | 3/2008 |
| JP | 2008-126085 A | 6/2008 |
| JP | 2011-509766 A | 3/2011 |
| JP | 2011-520580 A | 7/2011 |
| JP | 2012-020153 A | 2/2012 |
| JP | 2012-508048 A | 4/2012 |
| JP | 4988203 B2 | 8/2012 |
| JP | 2013-508031 | 3/2013 |
| JP | 5164571 B2 | 3/2013 |
| JP | 2013-516206 A | 5/2013 |
| JP | 2014-502867 A | 2/2014 |
| JP | 2015-500707 A | 1/2015 |
| JP | 2015-525652 A | 9/2015 |
| JP | 2017-505196 A | 2/2017 |
| WO | 91/09572 A1 | 7/1991 |
| WO | 92/04423 A2 | 3/1992 |
| WO | 92/07594 A1 | 5/1992 |
| WO | 92/14423 A1 | 9/1992 |
| WO | 93/04634 A1 | 3/1993 |
| WO | 93/04652 A1 | 3/1993 |
| WO | 93/17669 A1 | 9/1993 |
| WO | 94/04100 A1 | 3/1994 |
| WO | 95/31158 | 11/1995 |
| WO | 96/28100 A1 | 9/1996 |
| WO | 97/00054 A1 | 1/1997 |
| WO | 97/26847 A1 | 7/1997 |
| WO | 98/34552 A1 | 8/1998 |
| WO | 98/34568 A1 | 8/1998 |
| WO | 99/02214 A1 | 1/1999 |
| WO | 99/26562 A1 | 6/1999 |
| WO | 99/42062 A1 | 8/1999 |
| WO | 99/52478 A1 | 10/1999 |
| WO | 99/53871 A1 | 10/1999 |
| WO | 99/60956 A1 | 12/1999 |
| WO | 99/62417 A1 | 12/1999 |
| WO | 99/63914 A1 | 12/1999 |
| WO | 00/12033 | 3/2000 |
| WO | 00/13620 A1 | 3/2000 |
| WO | 00/24343 A1 | 5/2000 |
| WO | 00/67652 | 5/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 00/76409 A1 | 12/2000 |
| WO | 01/01893 A1 | 1/2001 |
| WO | 01/01895 A1 | 1/2001 |
| WO | 01/10316 A1 | 2/2001 |
| WO | 01/12054 A2 | 2/2001 |
| WO | 01/17464 A1 | 3/2001 |
| WO | 01/68004 A2 | 9/2001 |
| WO | 01/80751 A1 | 11/2001 |
| WO | 01/95838 A1 | 12/2001 |
| WO | 02/03870 A1 | 1/2002 |
| WO | 02/17824 A2 | 3/2002 |
| WO | 02/17825 A2 | 3/2002 |
| WO | 02/30338 A1 | 4/2002 |
| WO | 02/43601 A2 | 6/2002 |
| WO | 02/43628 A1 | 6/2002 |
| WO | 02/45627 A1 | 6/2002 |
| WO | 02/47563 A1 | 6/2002 |
| WO | 02/71921 A2 | 9/2002 |
| WO | 02/85250 A2 | 10/2002 |
| WO | 03/02021 A2 | 1/2003 |
| WO | 03/05937 A1 | 1/2003 |
| WO | 03/07854 A1 | 1/2003 |
| WO | 03/20169 A2 | 3/2003 |
| WO | 03/21308 A2 | 3/2003 |
| WO | 03/22165 A1 | 3/2003 |
| WO | 03/28587 A2 | 4/2003 |
| WO | 03/43488 A2 | 5/2003 |
| WO | 03/03951 A1 | 6/2003 |
| WO | 2003/101308 A1 | 12/2003 |
| WO | 2004/008949 A2 | 1/2004 |
| WO | 03/59180 A2 | 3/2004 |
| WO | 2004/030582 A2 | 4/2004 |
| WO | 2004/034924 A2 | 4/2004 |
| WO | 2004/062505 A1 | 7/2004 |
| WO | 2004/064603 A2 | 8/2004 |
| WO | 2004/069033 A2 | 8/2004 |
| WO | 2004/073563 A2 | 9/2004 |
| WO | 2004/078220 A2 | 9/2004 |
| WO | 2004/078221 A2 | 9/2004 |
| WO | 2004/080316 A1 | 9/2004 |
| WO | 2004/082526 A2 | 9/2004 |
| WO | 2004/098420 A2 | 11/2004 |
| WO | 2004/098453 A2 | 11/2004 |
| WO | 2004/108022 A1 | 12/2004 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/094297 A2 | 10/2005 |
| WO | 2005/112834 A2 | 12/2005 |
| WO | 2005/112835 A2 | 12/2005 |
| WO | 2005/115261 A1 | 12/2005 |
| WO | 2006/017507 A2 | 2/2006 |
| WO | 2006/044920 A2 | 4/2006 |
| WO | 2006/047587 A2 | 5/2006 |
| WO | 2006/047645 A2 | 5/2006 |
| WO | 2006/058079 A2 | 6/2006 |
| WO | 2006/058281 A2 | 6/2006 |
| WO | 2006/060420 A1 | 6/2006 |
| WO | 2006/063083 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/078972 A2 | 7/2006 |
| WO | 2006/081843 A1 | 8/2006 |
| WO | 2006/108067 A2 | 10/2006 |
| WO | 2006/118944 A1 | 11/2006 |
| WO | 2007/009107 A2 | 1/2007 |
| WO | 2007/022194 A2 | 2/2007 |
| WO | 2007/028098 A2 | 3/2007 |
| WO | 2007/048012 A2 | 4/2007 |
| WO | 2007/067726 A2 | 6/2007 |
| WO | 2007/084427 A2 | 7/2007 |
| WO | 2007/119212 A2 | 10/2007 |
| WO | 2007/124130 A2 | 11/2007 |
| WO | 2008/005627 A2 | 1/2008 |
| WO | 2008/011378 A1 | 1/2008 |
| WO | 2008/044057 A1 | 4/2008 |
| WO | 2008/064842 A2 | 6/2008 |
| WO | 2008/070863 A2 | 6/2008 |
| WO | 2008/103781 A2 | 8/2008 |
| WO | 2008/103832 A2 | 8/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2009/147527 A2 | 12/2009 |
| WO | 2009/152919 A1 | 12/2009 |
| WO | 2010/011348 A1 | 1/2010 |
| WO | 2010/068725 A2 | 6/2010 |
| WO | 2010/075451 A1 | 7/2010 |
| WO | 2010/075555 A2 | 7/2010 |
| WO | 2010/088766 A1 | 8/2010 |

(56) References Cited

FOREIGN PATENT DOCUMENTS

| | | |
|---|---|---|
| WO | 2010/121002 A1 | 10/2010 |
| WO | 2010/136170 A1 | 12/2010 |
| WO | 2010/148112 A1 | 12/2010 |
| WO | 2011/013047 A2 | 2/2011 |
| WO | 2011/046459 A1 | 4/2011 |
| WO | 2011/046460 A1 | 4/2011 |
| WO | 2011/060087 A1 | 5/2011 |
| WO | 2011/079910 A2 | 7/2011 |
| WO | 2011/119617 A1 | 9/2011 |
| WO | 2011/142761 A1 | 11/2011 |
| WO | 2011/150350 A1 | 12/2011 |
| WO | 2012/009152 A1 | 1/2012 |
| WO | 2012/027490 A2 | 3/2012 |
| WO | 2012/028182 A1 | 3/2012 |
| WO | 2012/030331 A1 | 3/2012 |
| WO | 2012/089317 A1 | 7/2012 |
| WO | 2012/103254 A2 | 8/2012 |
| WO | 2012/122294 A1 | 9/2012 |
| WO | 2012/129197 A1 | 9/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/148176 A1 | 10/2013 |
| WO | 2013/149611 A1 | 10/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2015/004660 A1 | 1/2015 |
| WO | 2015/013479 A2 | 1/2015 |
| WO | 2015/022039 A1 | 2/2015 |
| WO | 2015/048997 A1 | 4/2015 |
| WO | 2016/069796 A1 | 5/2016 |
| WO | 2016/118246 A1 | 7/2016 |
| WO | 2016/127139 A1 | 8/2016 |
| WO | 2017/040881 A1 | 3/2017 |
| WO | 2017/136620 A1 | 8/2017 |
| WO | 2018/078148 A1 | 5/2018 |

OTHER PUBLICATIONS

Brochure for PERPOS PLS System Surgical Technique by Interventional Spine, 2008, 8 pages.
Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.
Burkoth et al., A review of photocrosslinked polyanhydrides: in situ forming degradable networks. Biomaterials. Dec. 2000; 21 (23): 2395-2404.
Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.
Chin, "Early Results of the Triage Medical Percutaneous Transfacet Pedicular BONE-LOK Compression Device for Lumbar Fusion", Accessed online Jul. 10, 2017, 10 pages.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Fuchs, "The use of an interspinous implant in conjuction with a graded facetectomy procedure", Spine vol. 30, No. 11, pp. 1266-1272, 2005.
Gore, "Technique of Cervical Interbody Fusion", Clinical Orthopaedics and Related Research, Sep. 1984, pp. 191-195, No. 188.
Gray's Anatomy, Crown Publishers, Inc., 1977, pp. 33-54.
Hoogland et al., "Total Lumar Intervertebral Disc Replacement: Testing a New Articulating Space in Human Cadaver Spines-24 1", Annual ORS, Dallas, TX, Feb. 21-23, 1978, 8 pages.
Hunt, "Expandable Cage Placement Via a Posterolateral Approach in Lumbar Spine Reconstructions", Journal of Neurosurgery: Spine, Sep. 2006, pp. 271-274, vol. 5.
Iprenburg et al., "Transforaminal Endocopic Surgery in Lumbar Disc Hermiation in an Economic crises—The Tessys Method", US Musculoskeletal, 2008, pp. 47-49.
Kambin et al., "Percutaneous Lateral Discectomy of the Lumbar Spine: A Preliminary Report", Clin. Orthop,: 1983, 174: 127-132.
King., "Internal Fixation for Lumbosacral Fusion", The Journal of Bone and Joint Surgery, J. Bone Joint Surg. Am., 1948; 30: 560-578.
Krbec, "Replacement of the Vertebral Body with an Expansion Implant (Synex)", Acta Chir Orthop Traumatol Cech, 2002, pp. 158-162, vol. 69(3).
Link SB Charite Brochure—Intervertebral Prosthesis 1988, 29 pages.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Medco Forum, "Percutaneous Lumbar Fixation Via PERPOS PLS System Interventional Spine", Sep. 2008, vol. 15, No. 37.
Medco Forum, "Percutaneous Lumbar Fixation via PERPOS System From Interventional Spine", Oct. 2007, vol. 14, No. 49.
Morgenstern, "Transforaminal Endoscopic Stenosis Surgery—A Comparative Study of Laser and Reamed Foraminoplasty", in European Musculoskeletal Review, Issue 1, 2009.
Niosi, "Biomechanical Characterization of the three-dimentional kinematic behavior of the dynesys dynamic stabilization system: an in vitro study", Eur Spine J. (2006), 15: pp. 913-922.
Polikeit, "The Importance of the Endplate for Interbody Cages in the Lumbar Spine", Eur. Spine J., 2003, pp. 556-561, vol. 12.
ProMap TM EMG Navigation Probe. Technical Brochure Spineology Inc, Dated May 2009.
Shin, "Posterior Lumbar Interbody Fusion via a Unilateral Approach", Yonsei Medical Journal, 2006, pp. 319-325, vol. 47(3).
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Spine Solutions Brochure—Prodisc 2001, 16 pages.
Talwar "Insertion loads of the X STOP interspinous process distraction system designed to treat neurogenic intermittent claudication", Eur Spine J. (2006) 15: pp. 908-912.
U.S. Appl. No. 60/424,055, Method and apparatus for spinal fixation, filed Nov. 5, 2002.
U.S. Appl. No. 60/397,588, Method and apparatus for spinal fixation, filed Jul. 19, 2002.
U.S. Appl. No. 61/675,975, Expandable Implant, filed Jul. 26, 2012.
U.S. Appl. No. 60/942,998, Method and Apparatus for Spinal Stabilization, filed Jun. 8, 2007.
U.S. Appl. No. 14/640,220, filed Mar. 6, 2015, entitled Expandable Intervertebral Implant.
U.S. Appl. No. 14/685,358, filed Apr. 13, 2015, entitled Expandable Intervertebral Implant.
U.S. Appl. No. 14/685,402, filed Apr. 13, 2015, entitled Expandable Intervertebral Implant.
U.S. Appl. No. 14/790,866, filed Jul. 2, 2015, entitled Expandable Implant.
U.S. Appl. No. 60/794,171, filed Apr. 21, 2006, entitled Method and Apparatus for Spinal Fixation.
Zucherman, "A Multicenter, Prospective, Randomized Trial Evaluating the X STOP Interspinous Process Decompression System for the Treatment of Neurogenic Intermittent Claudication", SPINE, vol. 30, No. 12, pp. 1351-1358, 2005.

(56) References Cited

OTHER PUBLICATIONS

International Patent Application No. PCT/US2013/029014, International Search Report dated Jul. 1, 2013, 2 pages.
Bruder et al., Identification and characterization of a cell surface differentiation antigen on human osteoprogenitor cells. 42nd Annual Meeting of the Orthopaedic Research Society, p. 574, Feb. 19-22, 1996, Atlanta, Georgia.
Bruder et al., Monoclonal antibodies reactive with human osteogenic cell surface antigens. Bone. Sep. 1997;21(3):225-235.
Cambridge Scientific News, FDA Approves Cambridge Scientific, Inc.'s Orthopedic WISORB (TM) Malleolar Screw [online], Jul. 30, 2002 [retrieved on Oct. 14, 2003]. Retrieved from the Internet <URL: http://www.cambridgescientificinc.com>.
Carrino, John A., Roxanne Chan and Alexander R. Vaccaro, "Vertebral Augmentation: Vertebroplasty and Kyphoplasty", Seminars in Roentgenology, vol. 39, No. 1 Jan. 2004: pp. 68-84.
Cheng, B.C., Ph.D., Biomechanical pullout strength and histology of Plasmapore Registered XP coated implants: Ovine multi time point survival study. Aesculap Implant Systems, LLC, 2013, 12 pages.
Edeland, H.G., "Some Additional Suggestions For An Intervertebral Disc Prosthesis", J of Bio Medical Engr., vol. 7(1) pp. 57-62, Jan. 1985.
European Search Report EP03253921 dated Nov. 13, 2003, 4 pages.
Flemming et al., Monoclonal anitbody against adult marrow-derived mesenchymal stem cells recognizes developing vasculature in embryonic human skin. Developmental Dynamics. 1998;212:119-132.
Ha et al. (Topographical characterization and microstructural interface analysis of vacuum-plasma-sprayed titanium and hydroxyapatite coatings on carbon fiber-reinforced poly(etheretherketone), Journal of Materials Science: Materials in Science 9 (1997), pp. 891-896.
Haas, Norbert P., New Products from AO Development [online], May 2002 [retrieved on Oct. 14, 2003], Retrieved from the Internet <URL: http://www.ao.asif.ch/development/pdf_tk_news_02.pdf>.
Hao et al., Investigation of nanocomposites based on semi-interpenetrating network of [L-poly (epsilon-caprolactone)]/[net-poly (epsilon-caprolactone)] and hydroxyapatite nanocrystals. Biomaterials. Apr. 2003;24(9): 1531-9.
Harsha et al., Tribo performance of polyaryletherketone composites, Polymer Testing (21) (2002) pp. 697-709.
Haynesworth et al., Cell surface antigens on human marrow-derived mesenchymal cells are detected by monoclonal antibodies. Bone. 1992;13(1):69-80.
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
International Patent Application No. PCT /US2013/029014, International Search Report dated Jul. 1, 2013, 7 pages.
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kandziora, Frank, et al., "Biomechanical Analysis of Biodegradable Interbody Fusion Cages Augmented with Poly(propylene Glycol-co-Fumaric Acid)," SPINE, 27(15): 1644-1651 (2002).
Kotsias, A., Clinical trial of titanium-coated PEEL cages anterior cervical discectomy and fusion. [Klinishe Untersuching zum Einsatz von titanbeschichteten Polyetheretherketon-Implantaten bei der cervikalen interkorporalen fusion]. Doctoral thesis. Department of Medicine, Charite, University of Medicine Berlin, 2014, 73 pages. (German language document/Engl. summary).
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci US A. Jan. 30, 2001;98(3):842-7. Epub Jan. 23, 2001.

Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster#54, 5 pages.
McAfee et al., Minimally invasive anterior retroperitoneal approach to the lumbar spine: Emphasis on the lateral BAK. SPINE. 1998;23(13):1476-84.
Mendez et al., Self-curing acrylic formulations containing PMMA/ PCL composites: properties and antibiotic release behavior. J Biomed Mater Res. Jul. 2002;61 (1 ):66-74.
Nguyen et al., Poly(Aryl-Ether-Ether-Ketone) and its Advanced Composites: A Review, Polymer Composites, Apr. 1987, vol. 8, No. 2, pp. 57-73.
OSTEOSET Registered DBM Pellets (Important Medical Information) [online], Nov. 2002 [retrieved on Oct. 14, 2003], Retrieved from the Internet <URL: http://www.wmt.com/Literature>.
POROCOAT(R) Porous Coating, 1 Page, https://emea.depuysynthese.com/hcp/hip/products/qs/porocoat-porous-coatingemea Accessed on Jul. 31, 2017.
Regan et al., Endoscopic thoracic fusion cage. Atlas of Endoscopic Spine Surgery. Quality Medical Publishing, Inc. 1995;350-354.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.
Timmer et al., In vitro degradation of polymeric networks of poly(propylene fumarate) and the crosslinking macromer poly(propylene fumarate)-diacrylate. Biomaterials. Feb. 2003;24(4 ):571-7.
United States Disctrict Court, Central District of California, Case No. 1 :10-CV-00849-LPS, *Nuvasive, Inc.*, vs., *Globus Medical, Inc.*, Videotaped Deposition of: Luiz Pimenta, M.D., May 9, 2012, 20 pages.
Walsh et al., Preparation of porous composite implant materials by in situ polymerization of porous apatite containing epsilon-caprolactone or methyl methacrylate. Biomaterials. Jun. 2001;22( 11):1205-12.
Zimmer.com, Longer BAK/L Sterile Interbody Fusion Devices. Date believed to be 1997. Product Data Sheet.Zimmer. Retrieved Jul. 23, 2012 from <http:/ catalog.zimmer.com/contenUzpc/products/ 600/600/620/S20/S045. html>, 2 pages.
CN Office Action dated Apr. 24, 2020 for ON Application No. 201780040910.
U.S. Appl. No. 09/558,057, filed Apr. 26, 2000, entitled Bone Fixation System.
Allcock, "Polyphosphazenes"; The Encyclopedia of Polymer Science; 1988; pp. 31-41; vol. 13; Wiley Intersciences, John Wiley & Sons.
Cohn, "Biodegradable PEO/PLA Block Copolymers"; Journal of Biomedical Materials Research; 1988; pp. 993-1009; vol. 22; John Wiley & Sons, Inc.
Cohn, "Polymer Preprints"; Journal of Biomaterials Research; 1989; p. 498; Biomaterials Research Labortatory, Casal Institute of Applied Chemistry, Israel.
Heller, "Poly (Otrho Esters)"; Handbook of Biodegradable Polymers; edited by Domb; et al.; Hardwood Academic Press; 1997; pp. 99-118.
Japanese Office Action for Application No. 2013-542047, dated Sep. 8, 2015 (12 pages).
Japanese Office Action for Application No. 2016-135826, dated Jun. 6, 2017, (7 pages).
Kemnitzer, "Degradable Polymers Derived From the Amino Acid L-Tyrosine"; 1997; pp. 251-272; edited by Domb, et al., Hardwood Academic Press.
Khoo, "Minimally Invasive Correction of Grade I and II Isthmic Spondylolisthesis using AxiaLIF for L5/S1 Fusion", pp. 1-7, Rev B Sep. 15, 2008.

(56) References Cited

OTHER PUBLICATIONS

Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.
U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.
Vandorpe, "Biodegradable Polyphosphazenes for Biomedical Applications"; Handbook of Biodegradable Polymers; 1997; pp. 161-182; Hardwood Academic Press.

\* cited by examiner

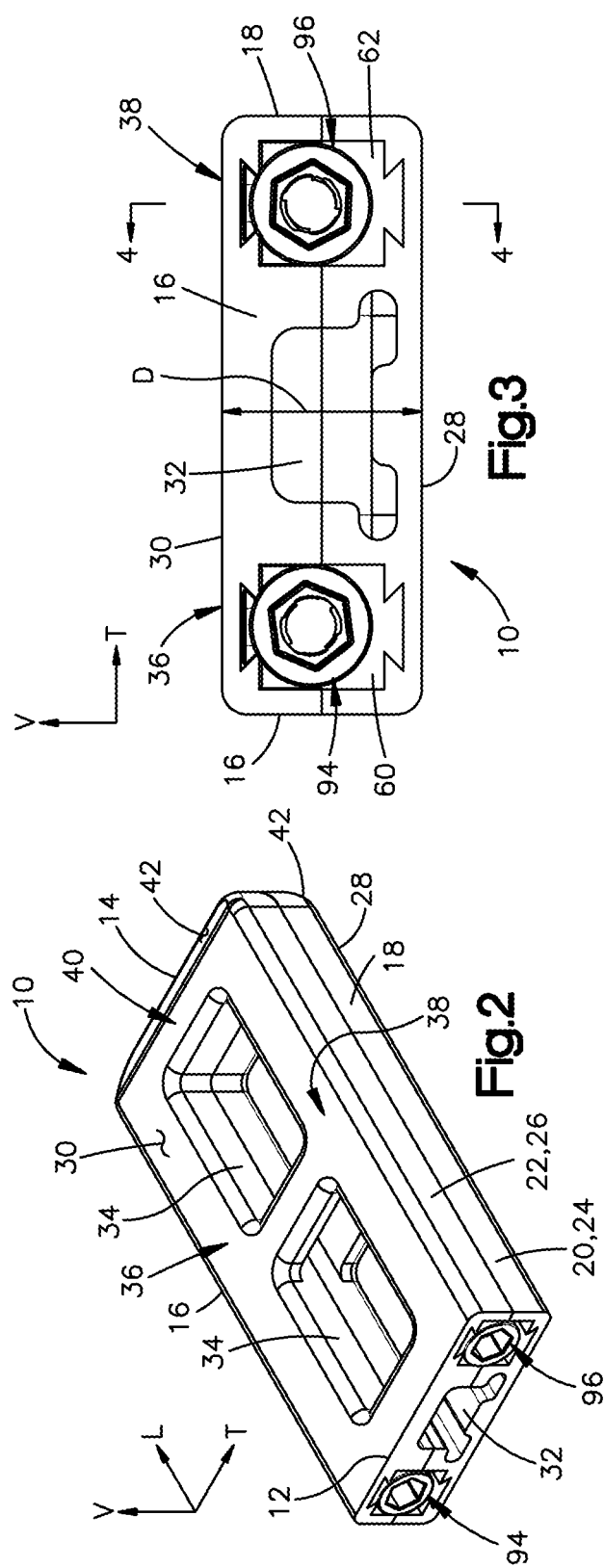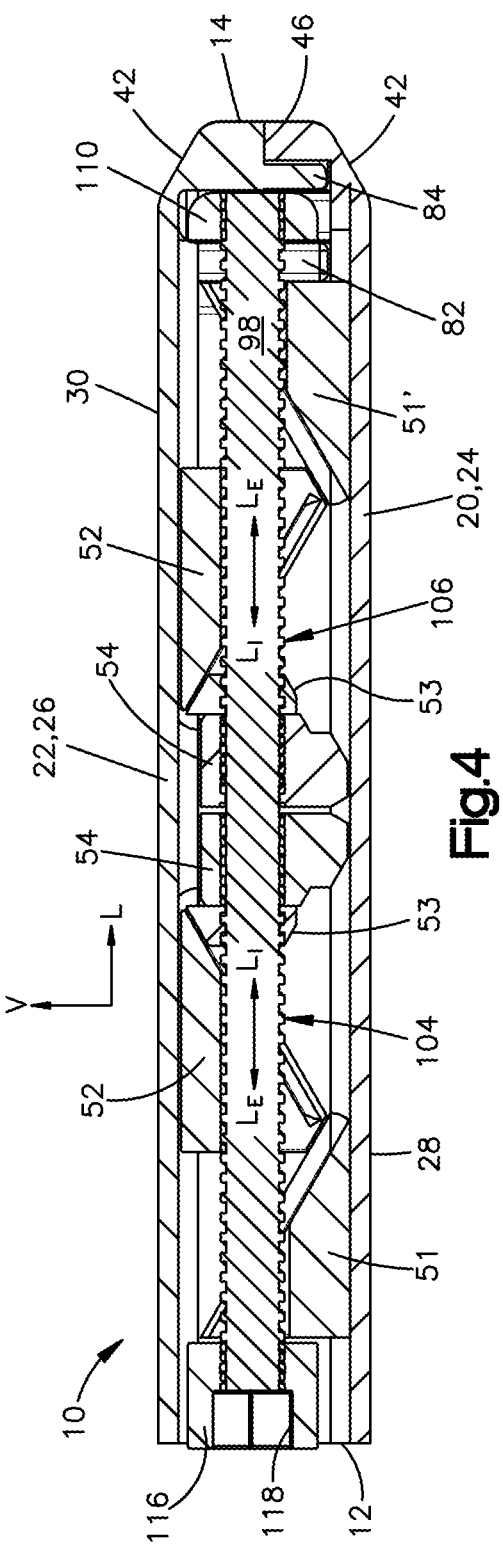

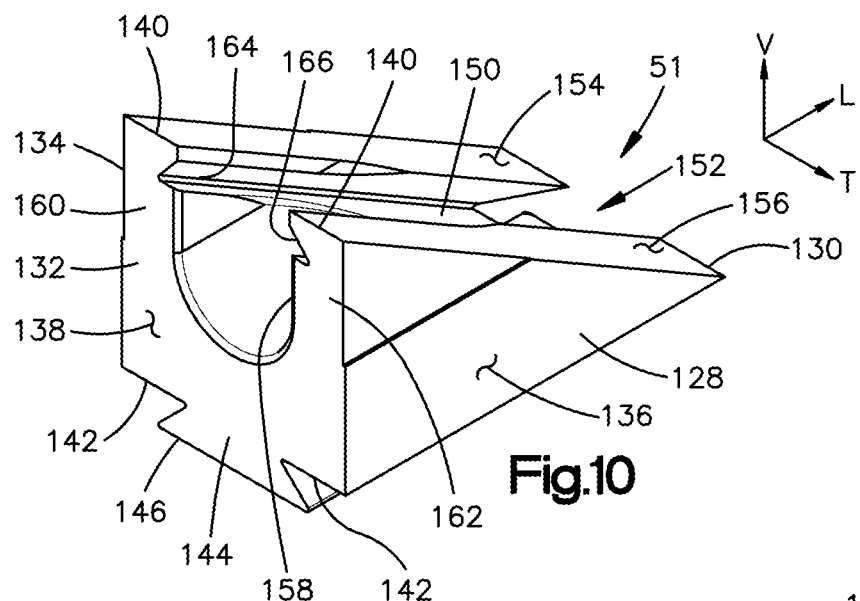
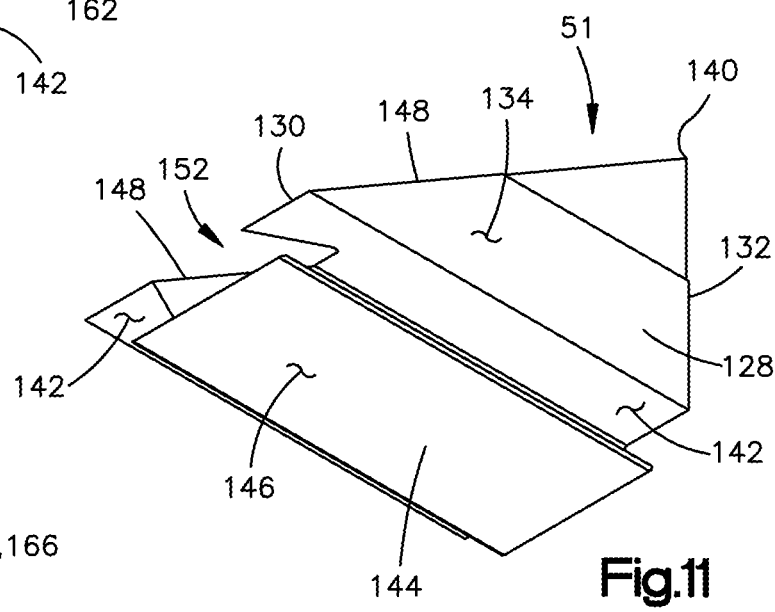
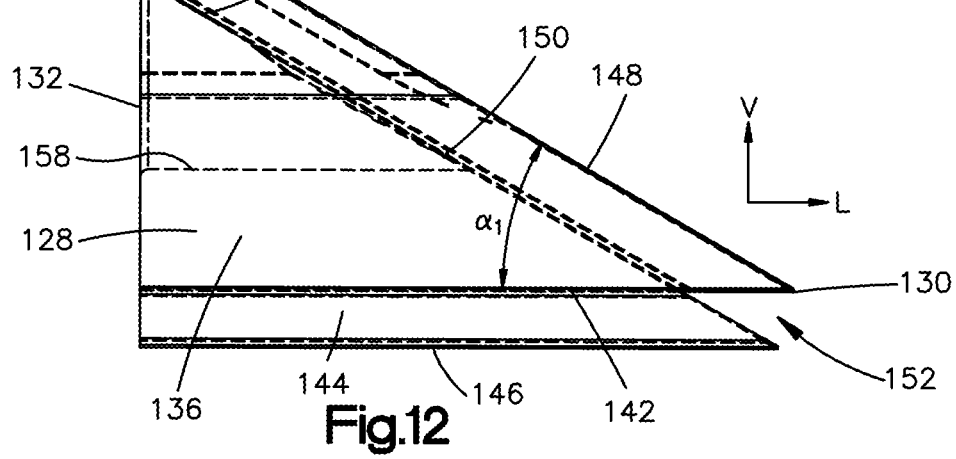

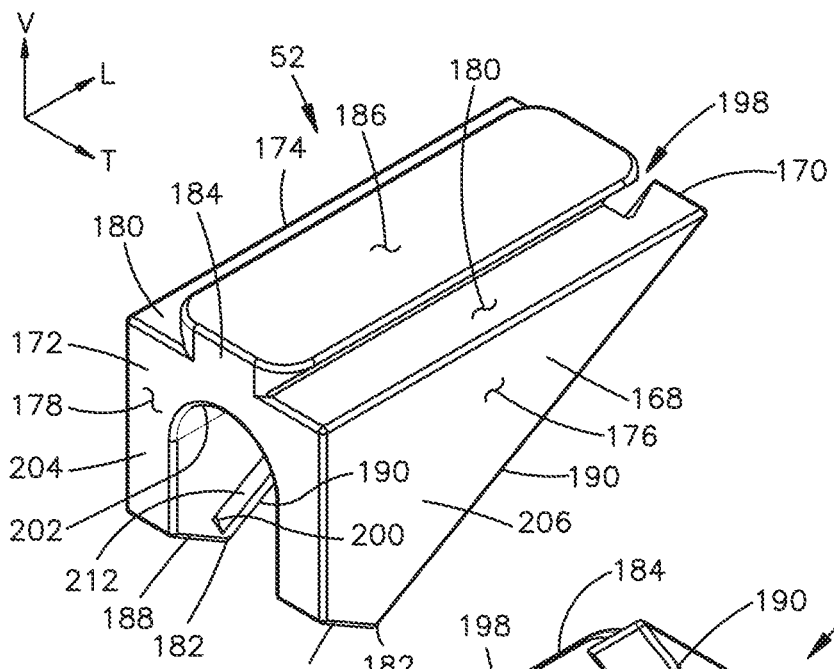
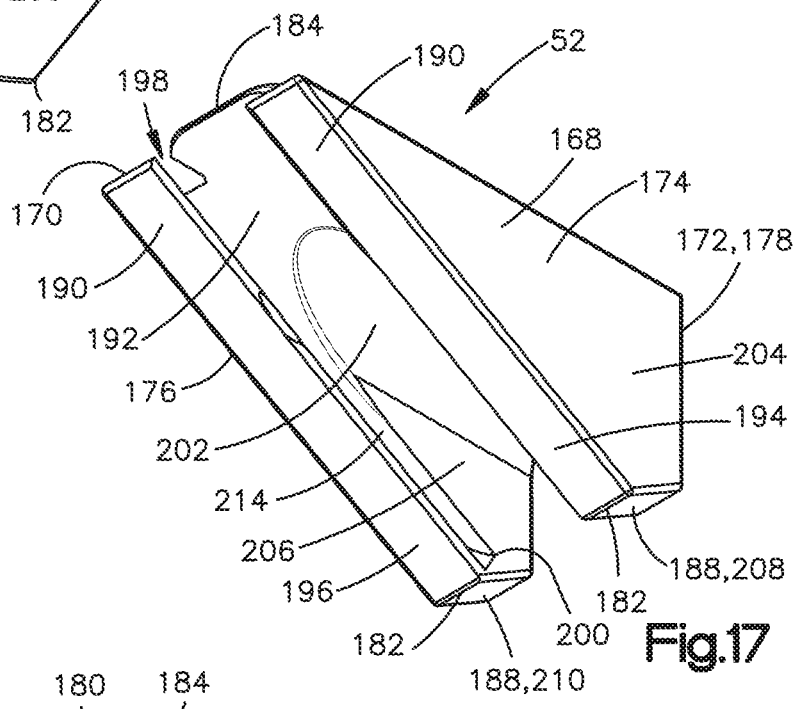
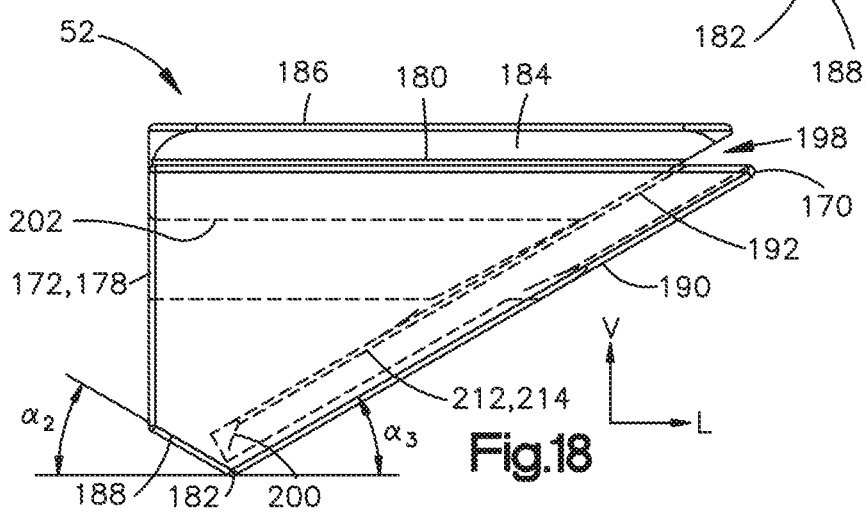

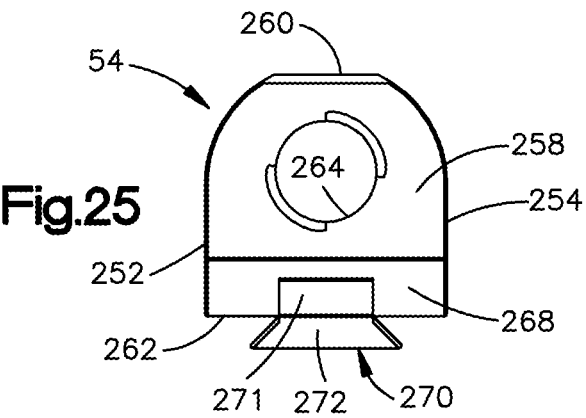
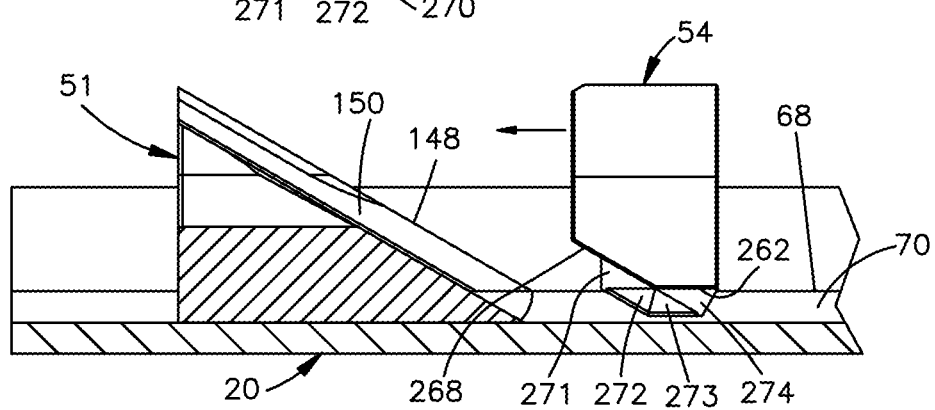
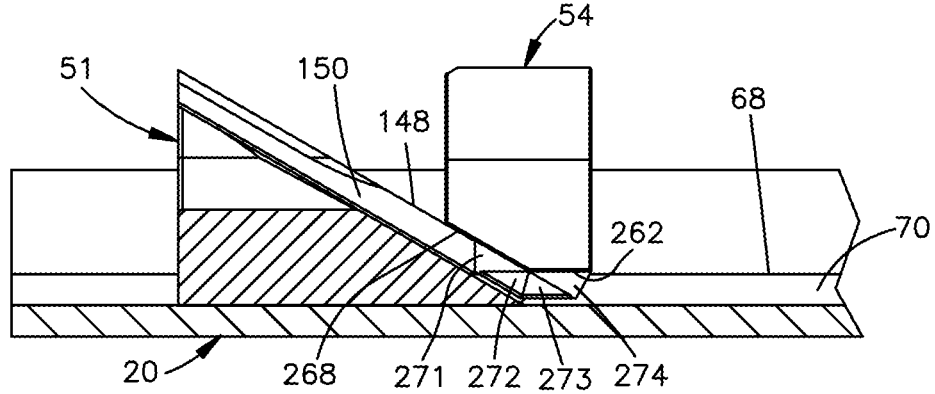
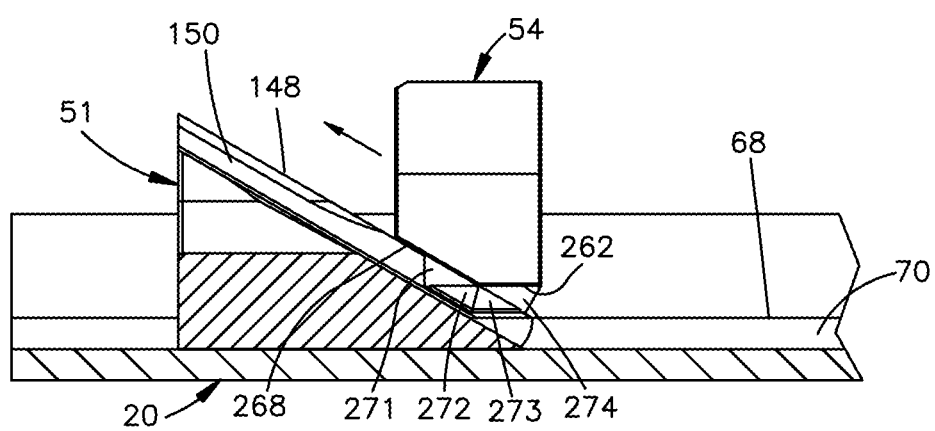

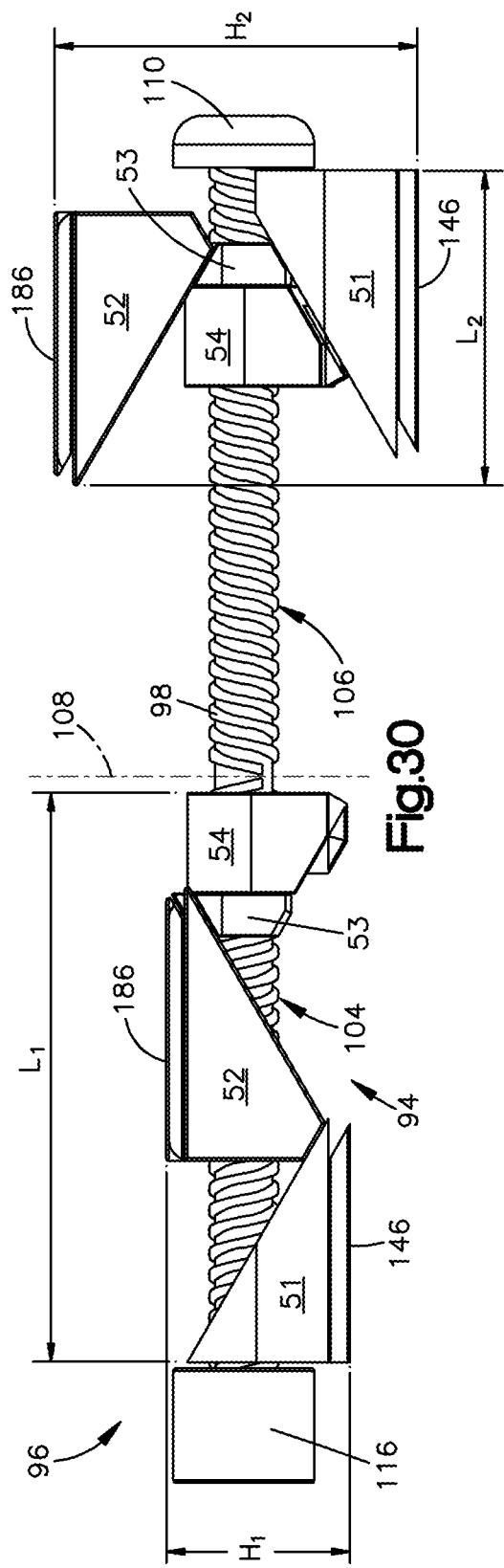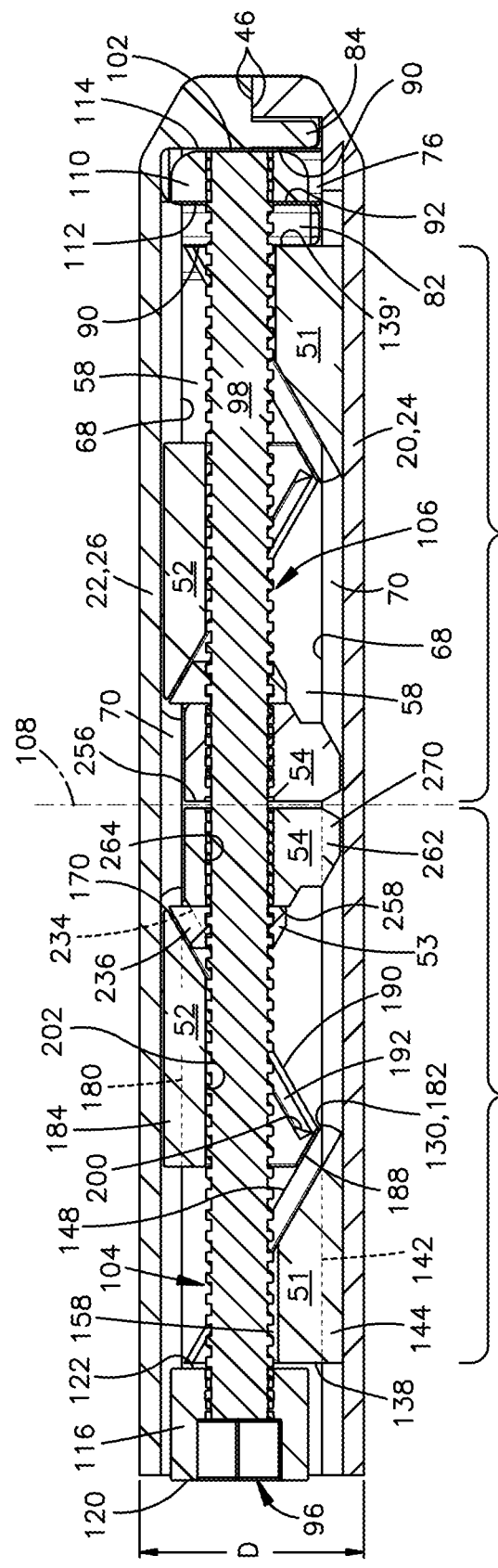

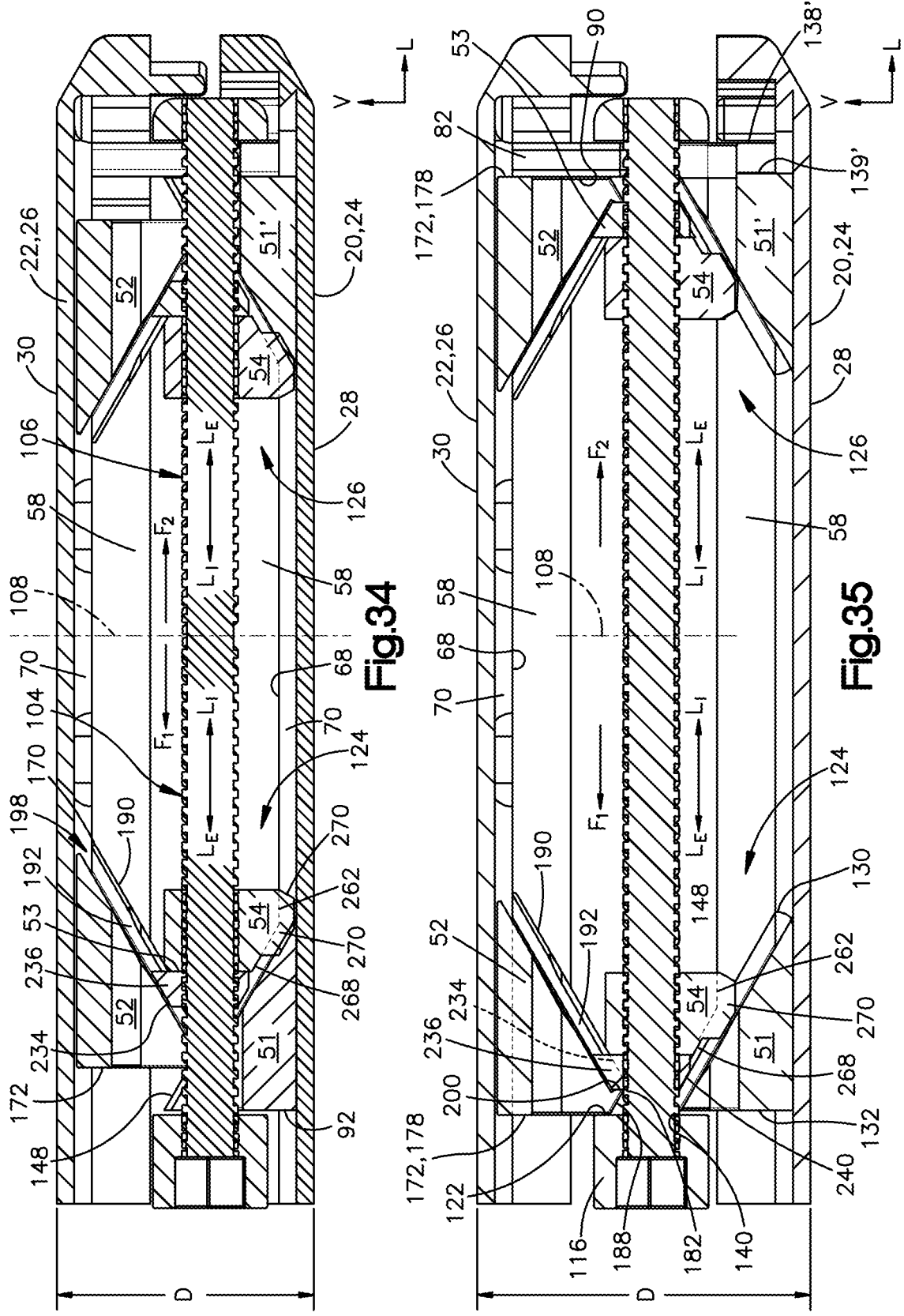

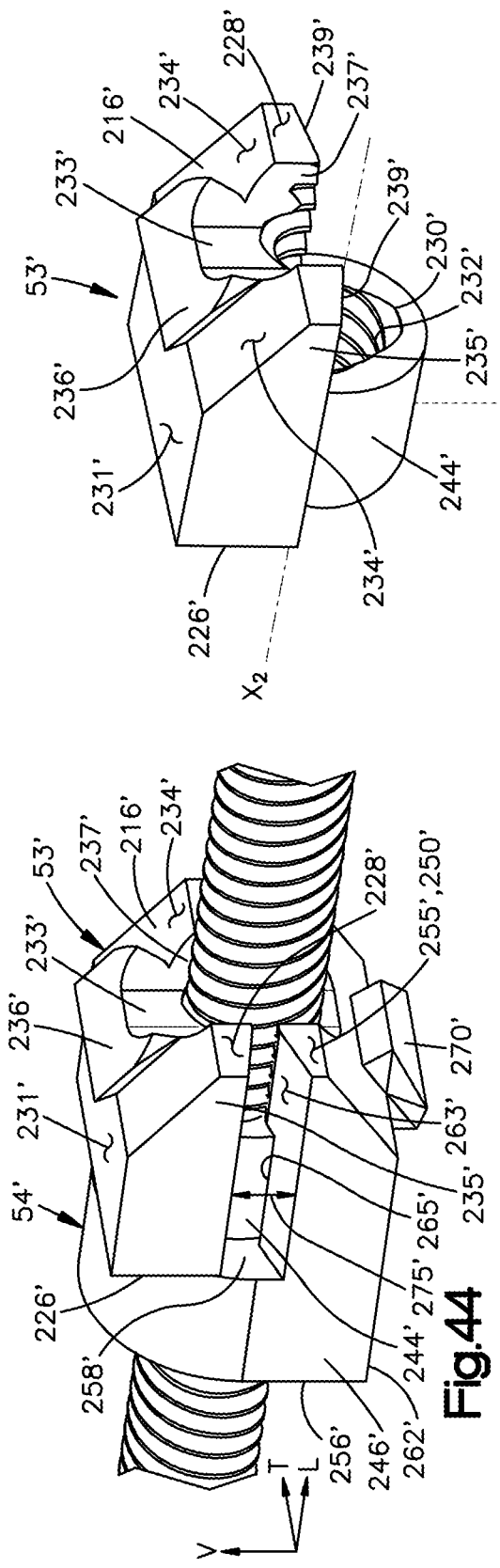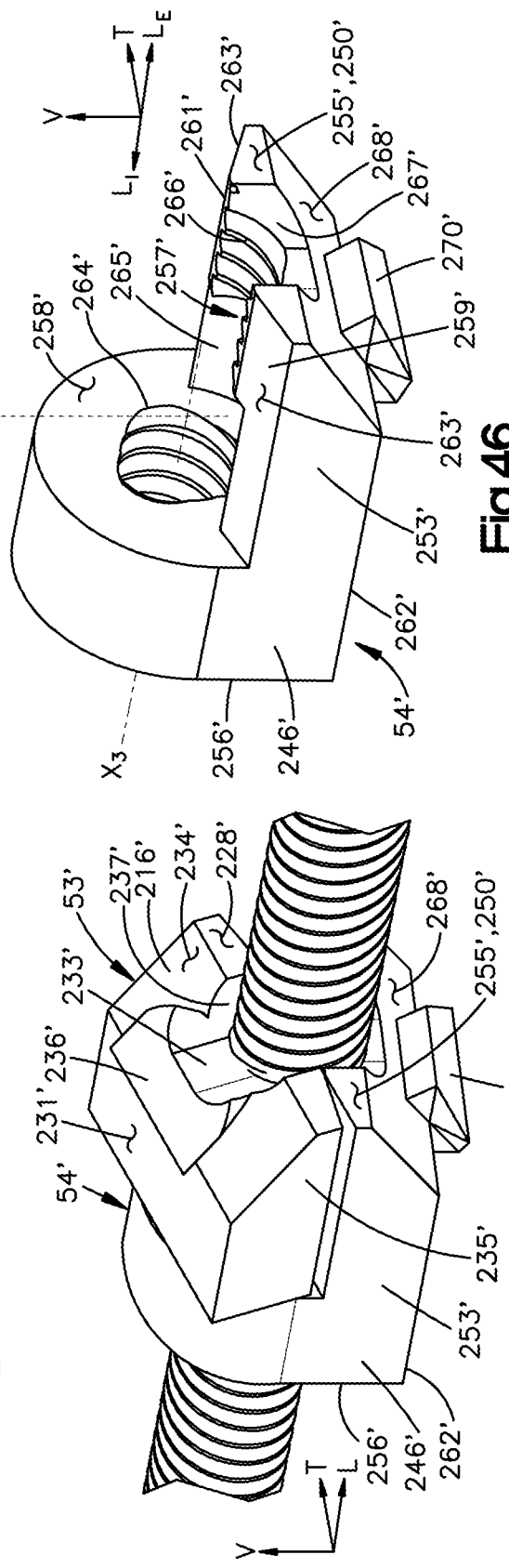

EXPANDABLE CAGE

CROSS REFERENCE TO RELATED APPLICATION

This application is a continuation of U.S. application Ser. No. 15/589,209, filed May 8, 2017, the entire contents of which are hereby incorporated by reference.

TECHNICAL FIELD

The present invention relates to an expandable intervertebral implant, particularly to an implant having a pair of endplates, at least one of which being independently expandable and rotatable relative to the other, and related methods

BACKGROUND

Removal of an intervertebral disc is often desired if the disc degenerates. Spinal fusion may be used to treat such a condition and involves replacing a degenerative disc with a device such as a cage or other spacer that restores the height of the disc space and allows bone growth through the device to fuse the adjacent vertebrae. Spinal fusion attempts to restore normal spinal alignment, stabilize the spinal segment for proper fusion, create an optimal fusion environment, and allows for early active mobilization by minimizing damage to spinal vasculature, dura, and neural elements. When spinal fusion meets these objectives, healing quickens and patient function, comfort and mobility improve. Spacer devices that are impacted into the disc space and allow growth of bone from adjacent vertebral bodies through the upper and lower surfaces of the implant are known in the art. Yet there continues to be a need for devices that minimize procedural invasiveness yet stabilize the spinal segment and create an optimum space for spinal fusion.

SUMMARY

According to an embodiment of the present disclosure, an intervertebral implant that is configured to iterate between a collapsed configuration and an expanded configuration includes a first plate and a second plate spaced from one another along a first direction. The first plate defines a first bone-contacting surface and the second plate defines a second bone-contacting surface that faces away from the first bone-contacting surface along the first direction. The implant includes an expansion assembly disposed between the first and second plates with respect to the first direction. The expansion assembly includes a first support wedge that supports the first plate and defines a first ramp and a second support wedge that supports the second plate and defines a second ramp and a third ramp. The expansion assembly includes an expansion wedge that defines a fourth ramp, wherein each of the first, second, third, and fourth ramps is inclined with respect to a second direction that is substantially perpendicular to the first direction. At least one of the first and second support wedges is slidable along the respective supported first or second plate. The implant includes an actuator configured to apply a drive force to the expansion wedge so as to cause 1) the fourth ramp to ride along the third ramp so as to increase a distance between the first and second bone-contacting surfaces along the first direction, and 2) the second ramp to ride along the first ramp, thereby further increasing the distance, thereby iterating the implant from the collapsed configuration to the expanded configuration.

According to another embodiment of the present disclosure, an implant for lateral insertion into an intervertebral space includes an expansion mechanism disposed between a first endplate and a second endplate with respect to a vertical direction. The first endplate defines a first-bone contacting surface and the second endplate defines a second bone-contacting surface that faces away from the first bone-contacting surface along the vertical direction. The expansion mechanism includes an anterior actuation assembly arranged along a first axis and a posterior actuation assembly arranged along a second axis. The first and second axes are each oriented along a longitudinal direction that is substantially perpendicular to the vertical direction. The first and second axes are spaced from one another along a transverse direction that is substantially perpendicular to the vertical and longitudinal directions. A first distance between the first and second bone-contacting surfaces along the vertical direction intersects the first axis, and a second distance between the first and second bone-contacting surfaces along the vertical direction intersects the second axis. The anterior and posterior actuation assemblies each include a first support wedge that supports the first endplate and a second support wedge that supports the second endplate and is slidable with respect to the first support wedge. The actuation assemblies each also include an expansion wedge slidable with respect to the second support wedge, and a drive shaft that is coupled to the expansion wedge and is rotatable about the respective first or second axis so as to cause 1) the expansion wedge to ride along the second support wedge, and 2) the second support wedge to ride along the first support wedge, thereby varying the respective first or second distance. The drive shafts of the anterior and posterior actuation assemblies are rotatable independently of each other so as to provide a difference between the first and second distances.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 2 is a perspective view of the implant of FIG. 1, shown in the collapsed configuration;

FIG. 3 is an end view of the implant of FIG. 1, shown in the collapsed configuration;

FIG. 4 is a longitudinal sectional view of the implant shown of FIG. 1, shown in the collapsed configuration;

FIG. 10 is a perspective view of a first expansion wedge of the expansion assemblies shown in FIGS. 5 and 6;

FIG. 11 is another perspective view of the first expansion wedge of FIG. 10;

FIG. 12 is a side view of the first expansion wedge of FIG. 10;

FIG. 16 is a perspective view of a second expansion wedge of the expansion assemblies shown in FIGS. 5 and 6;

FIG. 17 is another perspective view of the second expansion wedge of FIG. 16;

FIG. 18 is a side view of the second expansion wedge of FIG. 16;

FIG. 25 is a front end view of the fourth expansion wedge of FIG. 22;

FIG. 26 is a side, partial sectional view of the first and fourth wedges during a first phase of expansion of an expansion assembly shown in FIGS. 5 and 6;

FIG. 27 is a side, partial sectional view of the first and fourth wedges of FIG. 26 between the first phase and a second phase of expansion of the expansion assembly;

FIG. 28 is a side, partial sectional view of the first and fourth wedges during a second phase of expansion of the expansion assembly;

FIG. 30 is a side view of an actuation assemblies shown in FIGS. 5 and 6, with a proximal expansion assembly shown in a collapsed configuration and a distal expansion assembly shown in a fully expanded configuration for comparison;

FIG. 31 is an enlarged view of the longitudinal sectional view of FIG. 4, showing the implant in the collapsed configuration;

FIG. 34 is a longitudinal sectional view of the implant shown in FIGS. 32 and 33, taken along section line 34-34 of FIG. 33;

FIG. 35 is a longitudinal sectional view of the implant of FIG. 1, shown in a fully expanded configuration;

FIG. 44 is a perspective view of a pair of wedge members of the expansion mechanism of FIG. 43 positioned along a drive shaft of the expansion mechanism;

FIG. 45 is another perspective view of the wedge members of FIG. 44, shown with one of the wedge members rotated relative to the other wedge member about the drive shaft;

FIG. 46 is an exploded, perspective view of the wedge members of FIG. 44;

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Figure 1:
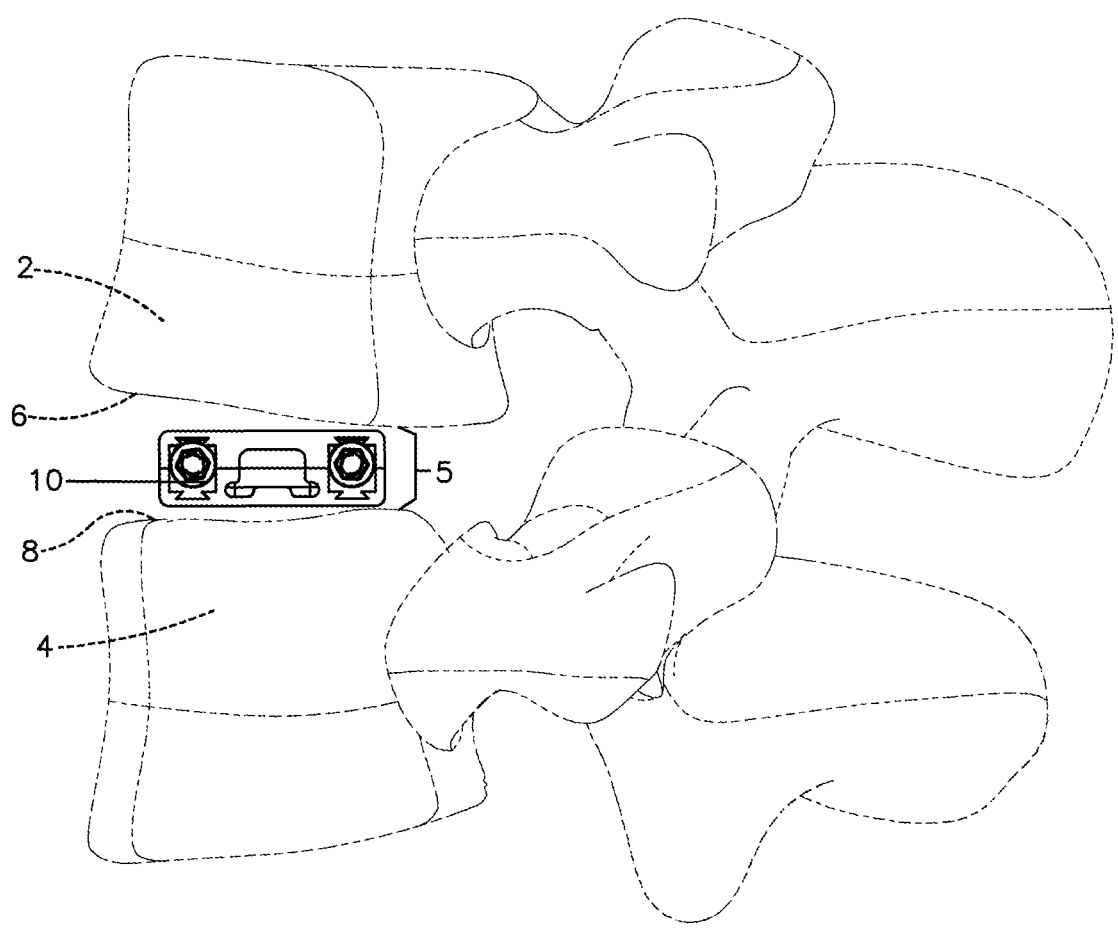
FIG. 1 is an end view of an implant positioned between adjacent vertebral bodies, wherein the implant is in a collapsed configuration, according to a first example embodiment of the present disclosure.

Referring to FIG. 1, a superior vertebral body 2 and an adjacent inferior vertebral body 4 define an intervertebral space 5 extending between the vertebral bodies 2, 4. The superior vertebral body 2 defines superior vertebral surface 6, and the adjacent inferior vertebral body 4 defines an inferior vertebral surface 8. The vertebral bodies 2, 4 can be anatomically adjacent, or can be remaining vertebral bodies after an intermediate vertebral body has been removed from a location between the vertebral bodies 2, 4. The intervertebral space 5 in FIG. 1 is illustrated after a discectomy, whereby the disc material has been removed or at least partially removed to prepare the intervertebral space 5 to receive an expandable intervertebral implant 10. The implant 10 is shown in a collapsed configuration, in which configuration the implant 10 can be configured for lateral insertion (i.e., along a medial-lateral trajectory) within the intervertebral space 5.

Once inserted in the intervertebral space 5, the implant 10 can be expanded in a cranial-caudal (i.e., vertical) direction, or otherwise iterated, between the collapsed configuration and a fully expanded configuration to achieve appropriate height restoration. Additionally, one of the sides of the implant 10 can be expanded vertically to a greater extent than the opposite side to achieve lordosis or kyphosis, as disclosed in more detail below.

The intervertebral space 5 can be disposed anywhere along the spine as desired, including at the lumbar, thoracic, and cervical regions of the spine. It is to be appreciated that certain features of the implant 10 can be similar to those set forth in U.S. Patent Publication No. 2014/0243982 A1, published Aug. 28, 2014 in the name of Miller, the entire disclosure of which is incorporated herein by this reference.

Certain terminology is used in the following description for convenience only and is not limiting. The words "right", "left", "lower" and "upper" designate directions in the drawings to which reference is made. The words "inner", "internal", and "interior" refer to directions towards the geometric center of the implant 10, while the words "outer", "external", and "exterior" refer to directions away from the geometric center of the implant. The words, "anterior", "posterior", "superior," "inferior," "medial," "lateral," and related words and/or phrases are used to designate various positions and orientations in the human body to which reference is made. When these words are used in relation to the implant 10 or a component thereof, they are to be understood as referring to the relative positions of the implant 10 as implanted in the body as shown in FIG. 1. The terminology includes the above-listed words, derivatives thereof and words of similar import.

The implant 10 is described herein as extending horizontally along a longitudinal direction "L" and a transverse direction "T", and vertically along a vertical direction "V". The longitudinal direction L can be at least substantially perpendicular to each of the transverse and vertical directions T, V. The transverse direction T can be at least substantially perpendicular to each of the longitudinal and vertical directions L, V. The vertical direction V can be at least substantially perpendicular to each of the longitudinal and transverse directions L, T. Unless otherwise specified herein, the terms "longitudinal," "transverse," and "vertical" are used to describe the orthogonal directional components of various implant components and implant component axes with reference to the orientation in which the implant 10 is configured to be located in the intervertebral space 5; however, such directional terms can be used consistently with reference to the implant regardless of its actual orientation. Additionally, it should be appreciated that while the longitudinal and transverse directions L, V are illustrated as extending along and defining a horizontal plane (also referred to herein as a "longitudinal-transverse plane"), and that the vertical direction is illustrated as extending along a vertical plane (such as either a "vertical-longitudinal plane" or a "vertical-transverse plane," as respectively referred to herein), the planes that encompass the various directions may differ during use. For instance, when the implant 10 is inserted into the intervertebral space 5, the vertical direction V extends generally along the superior-inferior (or caudal-cranial) direction, the longitudinal direction L extends generally along the medial-lateral direction, and the transverse direction L extends generally along the anterior-posterior direction. Thus, the horizontal plane lies generally in the anatomical plane defined by the anterior-posterior direction and the medial-lateral direction. Accordingly, the directional terms "vertical", "longitudinal", "transverse", and "horizontal" may be used to describe the implant 10 and its components as illustrated merely for the purposes of clarity and illustration, and such terms. With the foregoing in mind, the terms "expand" and "expansion," when used in reference to the implant 10, refer to expansion along the vertical direction V.

Referring now to FIG. 2, the implant 10 according to a first embodiment can define a proximal end 12 and a distal end 14 spaced from one another along the longitudinal direction L. In particular, the distal end 14 can be spaced from the proximal end 12 in a distal direction and the proximal end 12 can be spaced from the distal end 14 in a proximal direction opposite the distal direction. Thus, as used herein, the term "longitudinal direction L" is bi-directional and is defined by the mono-directional distal and opposed proximal directions. Additionally, the implant 10 can define an anterior side 16 and a posterior side 18 spaced from one another along the transverse direction T. In particular, the anterior side 16 can be spaced from the posterior side 18 in an anterior direction and the posterior side 18 can be spaced from the anterior side 16 in a posterior direction opposite the anterior direction. Thus, as used herein, the term "transverse direction T" is bi-directional and is defined by the mono-directional anterior and opposed posterior directions.

The implant 10 can include a first or inferior plate 20 and a second or superior plate 22 spaced from each other along the vertical direction V. The inferior and superior plates 20, 22 may be referred to as "endplates." The inferior plate 20 can define first or inferior plate body 24 and the superior plate 22 can define a second or superior plate body 26. The inferior plate body 24 can define a first or inferior bone-contacting surface 28 on an exterior thereof. The superior plate body 26 can define a second or superior bone-contacting surface 30 on an exterior thereof, as shown in FIG. 3. The inferior and superior bone-contacting surfaces 28, 30 can face away from one another. In particular, the superior bone-contacting surface 30 can face the superior vertebral surface 6 of the superior vertebra 2 and the inferior bone-contacting surface 28 can face the inferior vertebral surface 8 of the inferior vertebral body 4. The inferior and superior bone-contacting surfaces 28, 30 can each be substantially planar; however, in other embodiments, each bone-contacting surface 28, 30 can be at least partially convex, for example, and can at least partially define a texture (not shown), such as spikes, ridges, cones, barbs, indentations, or knurls, which are configured to engage the respective vertebral bodies 2, 4 when the implant 10 is inserted into the intervertebral space 5.

When the implant 10 is in the collapsed configuration, the inferior and superior bone-contacting surfaces 28, 30 can be spaced from one another by a distance D in the range of about 5 mm and about 20 mm along the vertical direction V, by way of non-limiting example, although other sizes are within the scope of the present disclosure. Additionally, when the implant 10 is in the collapsed configuration, the inferior and superior bone-contacting surfaces 28, 30 can be parallel with one another with respect to both the transverse direction T, and thus can have a neutral (i.e., neither lordotic or kyphotic) collapsed profile. As used herein, the terms "lordosis", "kyphosis", and their respective derivatives can be used interchangeably, with each term referring to any configuration of the implant 10 wherein the inferior and superior bone-contacting surfaces 28, 30 are angled with respect to each other in the vertical-transverse plane.

It is to be appreciated that the inferior and superior plate bodies 24, 26 can overly one another such that the proximal and distal ends 12, 14 of the implant 10 can be characterized as the proximal and distal ends 12, 14 of each plate 20, 22 or plate body 24, 26. Similarly, the anterior and posterior sides 16, 18 of the implant 10 can also be characterized as the anterior and posterior sides 16, 18 of each plate 20, 22 or plate body 24, 26.

As shown in FIGS. 2 and 3, the proximal end 12 of the implant 10 can include a coupling feature, such as a coupling aperture 32, for receiving an insertion instrument configured to insert the implant 10 into the intervertebral space. The coupling aperture 32 can be collectively defined by the inferior and superior plate bodies 24, 26. The implant 10 can also define one or more vertical apertures 34 (FIG. 2) extending through the inferior and superior plate bodies 24, 26 along the vertical direction V. The vertical apertures 34 can be in communication with one another and with the coupling aperture 32 and can be configured to receive bone growth material following expansion of the implant 10 for fusion with the superior and inferior vertebral bodies 2, 4.

With continued reference to FIG. 2, the implant 10 can generally define an anterior portion 36 and a posterior portion 38 each elongated along the longitudinal direction L and located on opposite sides of the vertical apertures 34 with respect to the transverse direction T. The implant 10 can also generally define a distal portion 40 spaced from the vertical apertures 34 in the distal direction. The distal end 14 of the implant 10 can also be termed the "insertion end" of the implant 10. To facilitate insertion, the superior and inferior plate bodies 12, 18 can each define a tapered surface 42 adjacent the distal end 14, wherein each tapered surface 42 is declined in the distal direction, as shown in FIGS. 2 and 4.

Figure 5:
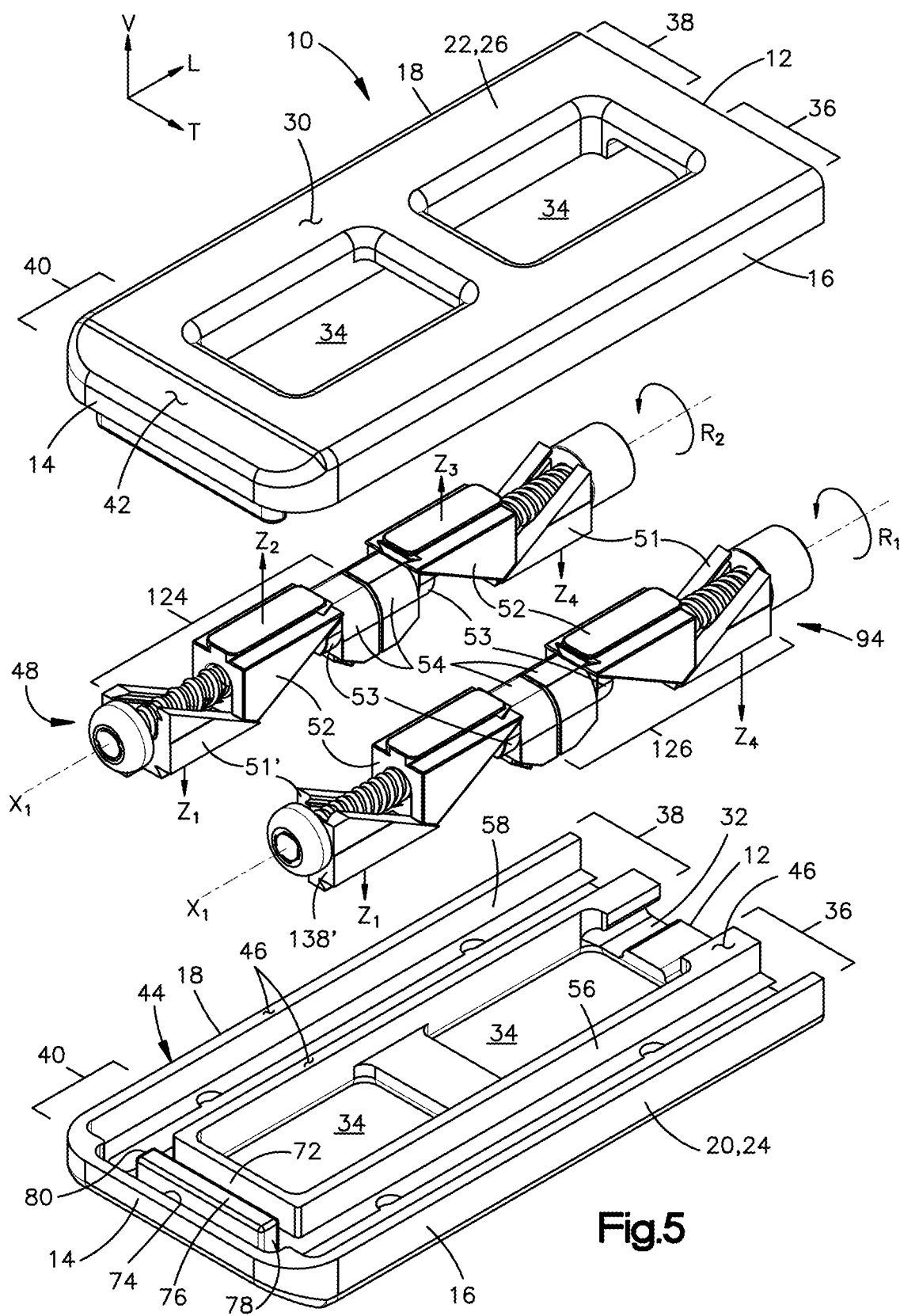
FIG. 5 is a partially exploded, perspective view of the implant of FIG. 1, with bone plates of the implant separated in a manner showing an internal expansion mechanism of the implant in a collapsed configuration.
Figure 6:
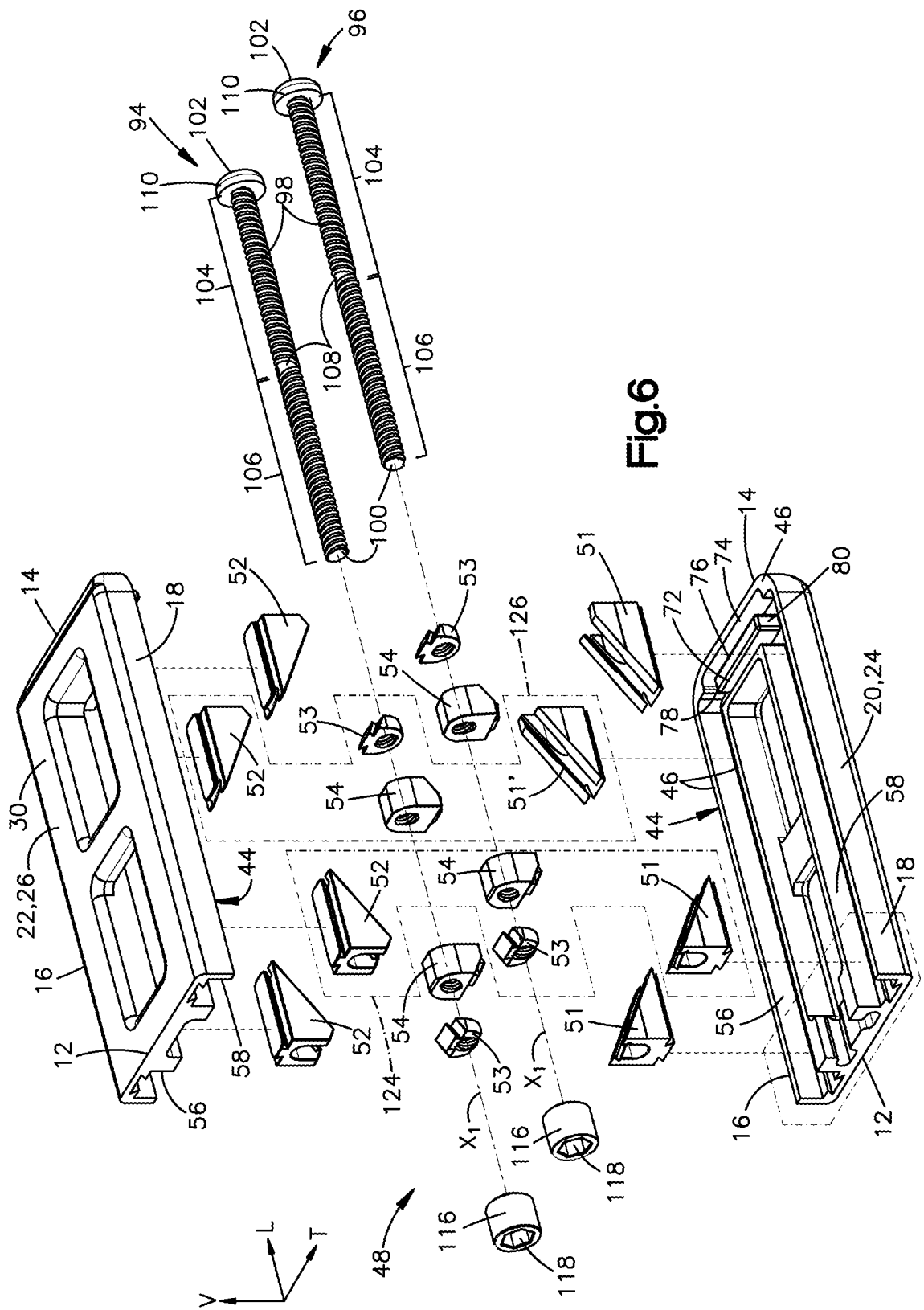
FIG. 6 is an exploded view of the implant of FIG. 1.

Referring now to FIGS. 5 and 6, each of the inferior and superior plate bodies 24, 26 can define an internal face 44 opposite the respective bone-contacting surface 28, 30 with respect to the vertical direction V. Additionally, the internal faces 44 of the inferior and superior plate bodies 24, 26 can each define one or more internal contact surfaces 46. When the implant 10 is in the collapsed configuration, the internal contact surfaces 46 of the superior plate body 26 can abut the internal contact surfaces 46 of the inferior plate body 24. The internal faces 44 of the inferior and superior plate bodies 24, 26 can be coupled to, and configured to interface with, an expansion mechanism 48 that is configured to move expansion members, such as wedges 51, 52, 53, 54, with respect to one another in a manner expanding the implant 10 along the vertical direction V, as discussed in more detail below.

The internal face 44 of each plate body 24, 26 can also define an anterior channel 56 and a posterior channel 58 each elongated along the longitudinal direction L. The anterior channel 56 and the posterior channel 58 of each plate 20, 22 can extend into the respective plate body 24, 26 from the internal contact surface 46 thereof toward the respective bone-contacting surface 28, 30 along the vertical direction V. The anterior channels 56 of the plates 12, 18 can be located within the anterior portion 36 of the implant 10, and the posterior channels 58 of the plates 12, 18 can be located within the posterior portion 38 of the implant 10. The anterior channels 56 of the plates 12, 18 can overly one another so as to at least partially define a first or anterior compartment 60 of the implant 10, while the posterior channels 58 of the plates 12, 18 can overly one another so as to at least partially define a second or posterior compartment 62 of the implant 10 (FIG. 3). The anterior and posterior compartments 60, 62 can be configured to house components of the expansion mechanism 48. Thus, the compartments 60, 62 can be termed "expansion compartments."

Figure 7:
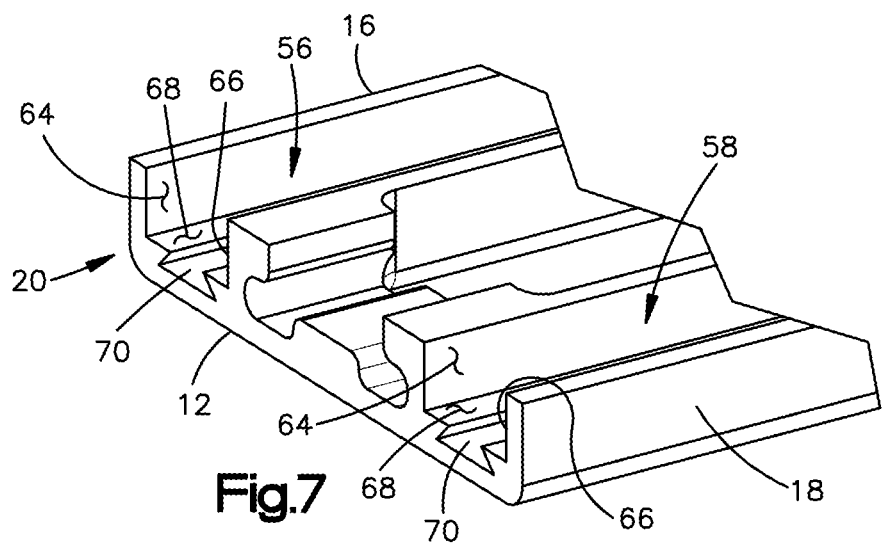
FIG. 7 is an enlarged view of an end portion of one of the bone plates shown in FIG. 6.

As shown more clearly in the enlarged view of FIG. 7, the anterior and posterior channels 56, 58 can each extend between opposed anterior and posterior sidewalls 64, 66 spaced apart along the transverse direction T. Each channel 56, 58 can also extend along the vertical direction V from the internal contact surface 46 to a base surface 68 of the channel 56, 58. Thus, the base surface 68 of each channel 56, 58 can be characterized as being vertically recessed within the plate body 24, 26 from the respective internal contact surface 46 toward the respective bone-contacting surface 28, 30. The base surface 68 of each channel can extend along the longitudinal and transverse directions L, T, and can optionally be substantially planar.

Each channel 56, 58 can also include a guide feature, such as a guide slot 70, that is recessed from the base surface 68 toward the bone-contacting surface 28, 30. Each guide slot 70 of the channels 56, 58 can also be referred to as a "plate guide slot" 70. The plate guide slot 70 can have a geometry configured to guide movement of one or more components of the expansion mechanism 48 within the channel 56, 58 along the longitudinal direction L. Optionally, the plate guide slot 70 can also be configured to provide mechanical interference with such components in the vertical direction V toward to the internal contact surface 46 of the associated plate 20, 22. Stated differently, the plate guide slot 70 can optionally have a geometry such that the plate body 24, 26 interlocks with said component of the expansion mechanism 48 in a manner preventing decoupling of the component from the plate guide slot 70 (and, by extension, from the channel 56, 58). Thus, the plate guide slot 70 can also be characterized as a retention feature. For example, the plate guide slot 70 can have a dovetail profile in the vertical-transverse plane, as shown. However, it is to be appreciated that other profiles and geometries of the plate guide slot 70 are within the scope of the present disclosure.

The internal faces 44 of the inferior and superior plate bodies 24, 26 can also define one or more coupling features for coupling the inferior and superior plate bodies 24, 26 together, particularly in the collapsed configuration. The coupling features of the plate bodies 14, 20 can be configured to nest within one another in a manner stabilizing the implant 10 throughout various phases of operation. For example, as shown in FIGS. 5 and 6, at the distal portion 40 of the inferior plate body 24, the internal face 44 can define a first transverse slot 72, a second transverse slot 74 spaced from the first transverse slot 72 in the distal direction, and a transverse wall 76 positioned between the first and second transverse slots 72, 74. The transverse wall 76 can extend along the transverse direction T between an anterior wall end 78 and a posterior wall end 80.

Figure 8:
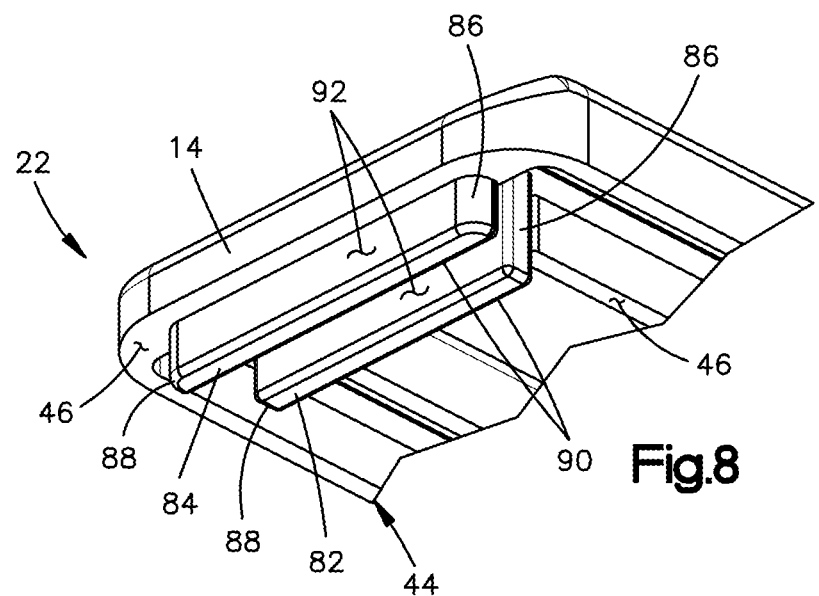
FIG. 8 is a reverse perspective view of an end portion of the other bone plate shown in FIG. 6.

As shown in FIG. 8, at the distal portion 40 of the superior plate body 26, the inner face 44 can define a first transverse protrusion 82 and a second transverse protrusion 84 spaced from the first transverse protrusion 82 in the distal direction. Each of the first and second transverse protrusions 82, 84 can protrude from the superior plate body 26 beyond the internal contact surfaces 46 thereof toward the inferior plate body 24. The first and second transverse protrusions 82, 84 can each extend along the transverse direction T between an anterior end 86 and a posterior end 88, and can extend along the longitudinal direction L between a proximal face 90 and a distal face 92. When the implant 10 is in the collapsed configuration, the first and second transverse protrusions 82, 84 of the superior plate body 26 can nest within the first and second transverse slots 72, 74, respectively, of the inferior plate body 24 (FIG. 4). As the implant 10 expands from the collapsed configuration, the transverse protrusions 82, 84 and transverse slots 72, 74 can effectively stabilize the implant and inhibit relative movement between the inferior and superior plate bodies 24, 26 along the longitudinal direction L.

Referring again to FIGS. 5 and 6, the expansion mechanism 48 can be positioned between the inferior and superior plates 20, 22. In the illustrated embodiment, the expansion mechanism 48 can be configured to convert one or more rotational input forces applied by a physician into one or more corresponding linear expansion forces along the vertical direction V. The expansion mechanism 48 can include one or more actuation assemblies 94, 96 each configured to convert a rotational input force into linear expansion forces along the vertical direction V. As shown, the expansion mechanism 48 can include a first or anterior actuation assembly 94 and a second or posterior actuation assembly 96 spaced from each other along the transverse direction T. The anterior actuation assembly 94 can be configured to convert a first rotational input force $R_1$ into a plurality of linear expansion forces $Z_1, Z_2, Z_3, Z_4$, along the vertical direction V so as expand the anterior portion 36 of the implant 10 along the vertical direction V. Similarly, the posterior actuation assembly 96 can be configured convert a second rotational input force $R_2$ into a plurality of linear expansion forces $Z_1, Z_2, Z_3, Z_4$, along the vertical direction V so as expand the posterior portion 38 of the implant 10 along the vertical direction V.

The anterior and posterior actuation assemblies 94, 96 can be driven so as to provide uniform or non-uniform expansion or contraction of the implant 10 along the vertical direction, as desired by a physician. For example, either of the actuation assemblies 94, 96 can be driven independently of the other. When driven independently, the anterior and posterior actuation assemblies 94, 96 can expand the anterior and posterior portions 36, 38 of the implant 10 to different expanded heights along the vertical direction V, providing the implant 10 with a lordotic profile in the intervertebral space 5, as discussed in more detail below. Thus, the implant 10 allows vertical expansion within the intervertebral space and adjustment of the lordotic angle of the implant 10 independently of one another.

Figure 9:
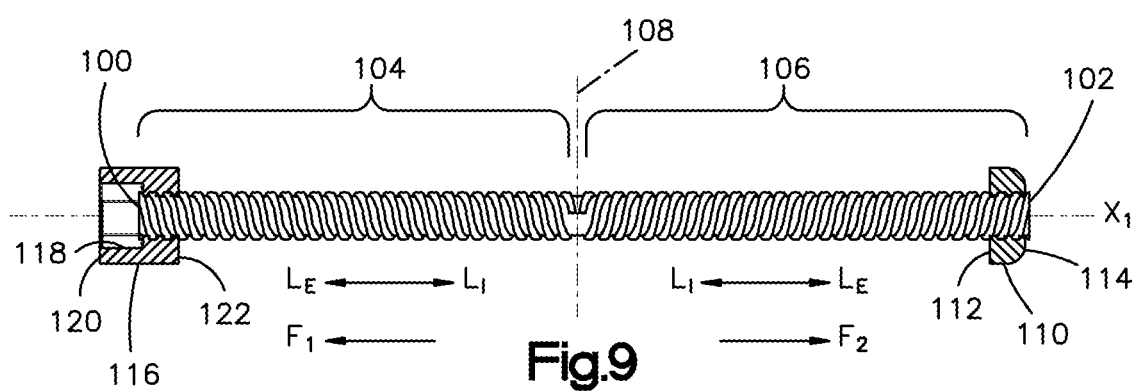
FIG. 9 is a longitudinal side view of an actuation member of the expansion mechanism shown in FIGS. 5 and 6.

The anterior and posterior actuation assemblies 94, 96 can be configured substantially similarly; accordingly, the same reference numbers will be used herein with reference to the corresponding components and features of the actuation assemblies 94, 96. Each actuation assembly 94, 96 can include an actuator, such as a drive shaft 98, as also shown in FIG. 9. Each drive shaft 98 can define a central shaft axis $X_1$ that extends along the longitudinal direction L, and can also define a proximal end 100 and a distal end 102 spaced from one another along the central shaft axis $X_1$.

With continued reference to FIG. 9, the drive shaft 98 can include one or more threaded portions 104, 106 configured to transmit one or more linear drive forces $F_1, F_2$ along the longitudinal direction L. For example, the drive shaft 98 can include a first or proximal threaded portion 104 and a second or distal threaded portion 106 spaced from the proximal threaded portion 104 in the distal direction along the central shaft axis $X_1$. The threading of the proximal and distal threaded portions 104, 106 can have different thread qualities. For example, in the illustrated embodiment, the proximal threaded portion 104 defines a thread pattern that is oriented in a direction opposite that of the distal threaded portion 106. In this manner, upon rotation of the drive shaft 98, the proximal threaded portion 104 can provide a first linear drive force $F_1$, the distal threaded portion 106 can provide a second linear drive force $F_2$, and the first and second linear drive forces $F_1, F_2$ can be opposite one another.

The drive shaft 98 can include an intermediate portion 108 positioned between the proximal and distal threaded portions 104, 106. The threading of the proximal threaded portion 104 can be substantially contiguous with the threading of the distal threaded portion 106 at the intermediate portion 108. Thus, the intermediate portion 108 can define a boundary between the threaded portions 104, 106. In the illustrated embodiment, the intermediate portion 108 can be characterized as an internal end of each of the proximal and distal threaded portions 104, 106, while the proximal end 100 of the drive shaft 98 can define the external end of the proximal threaded portion 104, and the distal end 102 of the drive shaft 98 can define the external end of the distal threaded portion 106. Furthermore, in the illustrated embodiment, the intermediate portions 108 of the anterior and posterior drive shafts 98 can define a center or midpoint of the implant 10 with respect to the longitudinal direction L. Thus, with respect to each threaded portion 104, 106 of the drive shaft 98 (and any component positioned thereon), an external longitudinal direction $L_E$ extends from the internal end 108 to the external end 100, 102, and an internal longitudinal direction $L_I$ extends from the external end 100, 102 to the internal end 108.

A head 110 can be located at the distal end 102 of the drive shaft 98 and can be contiguous with the distal threaded portion 106. The head 110 can be monolithic with the drive shaft 98 or can be a separate component, such as a nut that is threadedly coupled to the distal threaded portion 106. The head 110 can define a proximal end 112 and a distal end 114 spaced from the proximal end 112 along the longitudinal direction L. A drive coupling, such as a nut socket 116, can be threadedly coupled to the proximal end 100 of the drive shaft 98 and can be contiguous with the proximal threaded portion 104. The nut socket 116 can define a socket aperture 118 extending from a proximal end 120 of the nut socket 116 toward a distal end 122 thereof. The socket aperture 118 can define a hex socket, as depicted, although other socket configurations can be employed for connection to a driving tool operated by a physician.

Referring again to FIGS. 5 and 6, each actuation assembly 94, 96 can include one or more expansion assemblies 124, 126 (also referred to as "wedge assemblies") that expand along the vertical direction V. For example, a first or proximal wedge assembly 124 can be engaged with the proximal threaded portion 104 of the drive shaft 98 and a second or distal wedge assembly 126 can be engaged with the distal threaded portion 106 of the drive shaft 98. In FIG. 6, the proximal wedge assembly 124 of the posterior actuation assembly 96 is identified in dashed lines, while the distal wedge assembly 126 of the anterior actuation assembly 94 is identified in dashed lines. The proximal and distal wedge assemblies 124, 126 can be characterized as subassemblies of the respective anterior and posterior actuation assemblies 94, 96. Additionally, within each actuation assembly 94, 96, the proximal and distal wedge assemblies 124, 126 can optionally be substantial mirror images of one another about a vertical-transverse plane positioned at the intermediate portion 108 of the drive shaft 98. Stated differently, the distal wedge assembly 126 can be configured virtually identical (or at least substantially similar) to the proximal wedge assembly 126, with the primary difference being that the distal wedge assembly 126 is flipped with respect to the longitudinal direction L. Some minor variations in the proximal and distal wedge assemblies 124, 126 will be set forth more fully below.

Each proximal and distal wedge assembly 124, 126 can include a plurality of expansion members, or wedges 51, 52, 53, 54, that are movable relative to each other so as to increase their collective height along the vertical direction V. For example, the expansion members can include a first wedge 51, a second wedge 52, a third wedge 53, and a fourth wedge 54. One or more of the wedges 51, 52, 53, 54 can engage the respective threaded portion 104, 106 of the drive shaft 98.

With reference to FIG. 4, when the implant 10 is in the collapsed configuration, the first wedge 51 can be positioned adjacent the external end of the respective threaded portion 104, 106 of the drive shaft 98; the second wedge 52 can be spaced from the first wedge 51 in the internal longitudinal direction $L_I$; the third wedge 53 can be spaced from the second wedge 52 in the internal longitudinal direction $L_I$; and the fourth wedge 54 can be spaced from the third wedge 53 in the internal longitudinal direction $L_I$. Accordingly, the first wedge 51 can be characterized as an "external-most" wedge, while the fourth wedge 54 can be characterized as an "internal-most" wedge, although other configurations are possible. Additionally, the wedges 51, 52, 53, 54 can define geometries that provide each wedge assembly 124, 126 with telescopic mobility in the longitudinal and vertical directions L, V. Stated differently, the wedges 51, 52, 53, 54 can be shaped such that, as the wedges 51, 52, 53, 54 engage one another, their collective height can increase while their collective length decreases, and vice versa, as set forth in more detail below.

Referring now to FIGS. 10 through 12, the first wedge 51 can have a first wedge body 128 that defines an internal end 130 and an external end 132 spaced from the internal end 130 along the longitudinal direction L. The first wedge body 128 can also define anterior and posterior side surfaces 134, 136 spaced from each other along the transverse direction T. The external end 132 of the first wedge body 128 can define an external face 138 extending between an upward apex 140 and a bottom or base surface 142 of the body 128 along the vertical direction V. The external face 138 can be substantially planar, although other geometries are within the scope of the present disclosure. The external face 138 can be configured to abut another component of the implant 10 in a manner limiting or preventing motion of the first wedge body 128 in the external longitudinal direction $L_E$ during operation of the implant 10 within a patient. For example, in the proximal wedge assembly 124, the external face 138 of the first wedge 51 can be configured to abut the distal end 122 of the nut socket 116, by way of non-limiting example.

The upward apex 140 can be located at the external end 132 of the first wedge body 128. The base surface 142 of the first wedge body 128 can be configured to engage the base surface 68 of the respective anterior or posterior channel 56, 58 of the inferior plate body 24. At least a portion of the base surface 142 of the first wedge body 128 can be substantially planar and can be configured to translate at least partially across the base surface 68 of the respective channel 56, 58, for example, at least during assembly of the implant 10. In other embodiments, once in place within the respective channel 56, 58, the first wedge 51 can be fixed to the inferior plate body 24, such as by welding, brazing, adhesives, or mechanical fasteners. In further embodiments, the first wedge 51 can be monolithic with the inferior plate body 24. As the first wedge 51 can be characterized as "supporting" the inferior plate body 24, the first wedge 51 can be referred to herein as a "support member" or a "support wedge."

In the illustrated embodiments, the first wedge 51 can also include a first or inferior guide element, such as a guide protrusion 144, that is configured to translate within the plate guide slot 70 of the associated channel 56, 58 during assembly of the implant 10, for example. The guide protrusion 144 can extend from the base surface 142 of the first guide body 128. A bottom surface 146 of the guide protrusion 144 can define a bottom-most portion of the first wedge 51 and of the respective wedge assembly 124, 126. The guide protrusion 144 can have a geometry that is configured to guide movement of the first wedge body 128 within the respective channel 56, 58 along the longitudinal direction L. Additionally, the guide protrusion 144 of the first wedge body 128 and the respective guide slot 70 of the inferior plate body 24 can be cooperatively shaped so that the first wedge body 128 interlocks with the inferior plate body 24 in a manner preventing the first wedge body 128 and the inferior plate body 24 from detaching along the vertical direction V. For example, the guide protrusion 144 and the plate guide slot 70 can have corresponding dovetail profiles in the vertical-transverse plane, as shown, although other geometries are within the scope of the present disclosure. In this manner, the first wedge 51 can be longitudinally movable but substantially vertically immovable within the respective channel 56, 58 of the inferior plate body 24. Thus, the guide protrusion 144 can also be characterized as a retention feature of the first wedge 51. Additionally, the profiles of the guide protrusion 144 and of the plate guide slot 70 can allow the first wedge 51 and the inferior plate body 24 to be rotationally interlocked with one another so that, for example, the first wedge 51 and the inferior plate body 24 can maintain the same angular position about the central shaft axis $X_1$ during expansion and optionally during lordosis. In other embodiments, the rotational interlocking of the first wedge 51 and the inferior plate body 24 can allow rotation of the first wedge 51 about the central shaft axis $X_1$ to cause a substantially similar degree of rotation of the inferior plate body 24 about the central shaft axis $X_1$, and vice versa.

The first wedge body 128 can also include an engagement element configured to engage a portion of one or more other wedges of the respective wedge assembly 124, 126, such as the second wedge 52 and the fourth wedge 54, for example. The engagement element can include a first inclined surface, or ramp 148, extending between the internal end 130 and the upward apex 140 of the first wedge body 128. When positioned within the respective actuation assembly, 94, 96, the first wedge 51 can be oriented so that the first ramp 148 is inclined in the external longitudinal direction $L_E$. In the illustrated embodiment, the first ramp 148 can be oriented at a first incline angle $\alpha_1$ in a range of about 10 degrees and about 60 degrees with respect to the longitudinal direction L (FIG. 12). In other embodiments, the first incline angle cu can be in the range of about 20 degrees and about 40 degrees with respect to the longitudinal direction L. In further embodiments, the first incline angle $\alpha_1$ can be in the range of about 25 degrees and about 35 degrees with respect to the longitudinal direction L. In additional embodiments, the first incline angle $\alpha_1$ can be less than 10 degrees or greater than 60 degrees with respect to the longitudinal direction L.

The first wedge body 128 can also define a second or superior guide feature, such as a guide slot 150, configured to guide relative motion between the first wedge 51 and another wedge of the associated wedge assembly 124, 126, such as the fourth wedge 54, for example. The guide slot 150 can be recessed into the first wedge body 128 from the first ramp 148. The guide slot 150 can extend from a guide slot opening 152 at the internal end 130 of the first wedge body 128 to the external face 138 of the first guide body 128 with respect to the longitudinal direction L. The guide slot 150 can extend parallel with the first ramp 148 and can have a geometry configured to guide movement therein of an associated guide element of the fourth wedge 54. Optionally, the guide slot 150 can also be configured to interlock with the associated guide element in a manner preventing the fourth wedge 54 from detaching from the first wedge 51, at least in a direction orthogonal to the first ramp 148. As shown, the guide slot 150 can have a dovetail profile in the vertical-transverse plane, although other geometries are within the scope of the present disclosure. The guide slot 150 can traverse an entire length of the first ramp 148, as shown, or can optionally traverse less than the entire length. Additionally, the guide slot 150 can separate the first ramp 148 into anterior and posterior portions 154, 156, which can be characterized as "rails."

The first wedge body 128 can define a channel 158 extending through the body 128 along the longitudinal direction L. The channel 158 can be U-shaped, and portions of the first wedge body 128 located on opposite transverse sides of the channel 158 can be characterized as anterior and posterior arms 160, 162 of the first wedge body 128 (FIG. 10). The channel 158 can be sized, shaped, and/or otherwise configured to provide space for the respective threaded portion 104, 106 of the drive shaft 98 to extend at least partially through the body 128 (i.e., between the arms 160, 162) without mechanically interfering with the body 128. Accordingly, the first wedge body 128 can have a U-shaped profile in a vertical-transverse plane. The channel 158 can also intersect the guide slot 150 in a manner effectively dividing a portion of the guide slot 150 into anterior and posterior slots 164, 166 defined in the anterior and posterior arms 160, 162, respectively.

Figure 13:
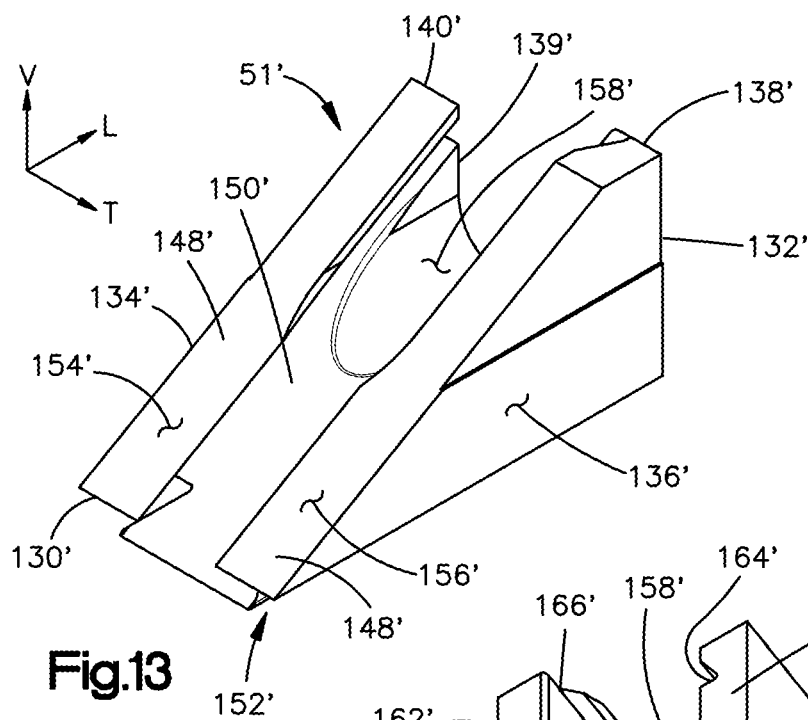
FIG. 13 is a perspective view of a variant of the first expansion wedge shown in FIGS. 10 through 12.
Figure 14:
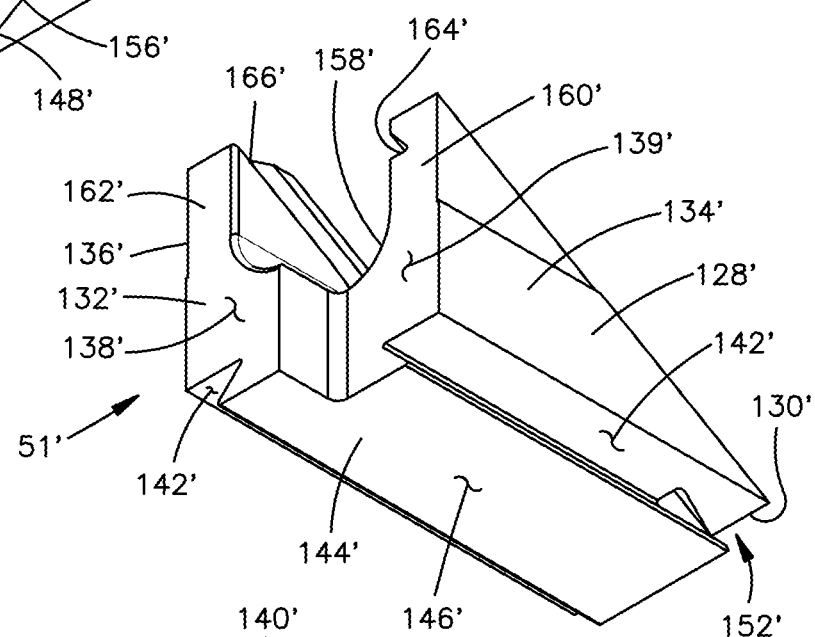
FIG. 14 is another perspective view of the variant of the first expansion wedge of FIG. 13.
Figure 15:
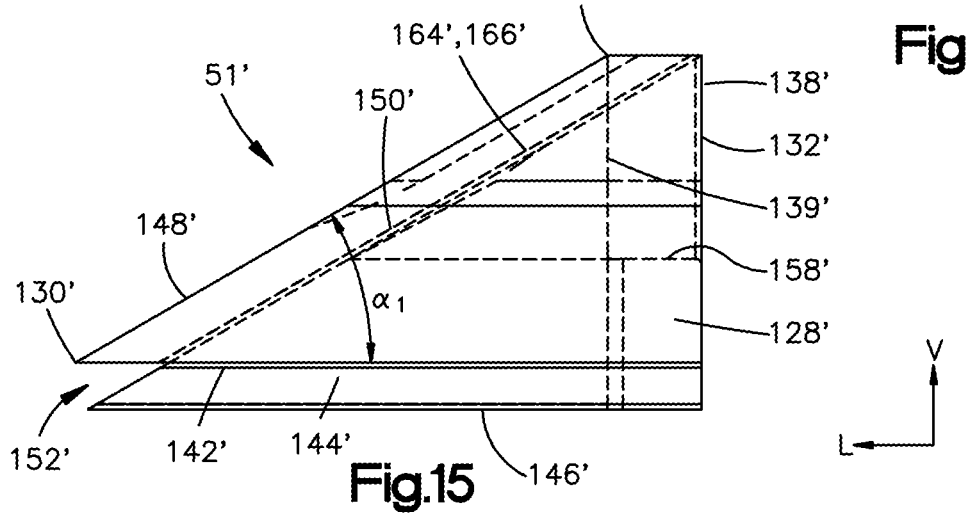
FIG. 15 is a side view of the variant of the first expansion wedge of FIG. 13.

Referring now to FIGS. 13 through 15, a variation of the first wedge 51' is shown. In particular, the variant 51' can be employed in the posterior actuation assembly 96. The variant 51' can be substantially similar to the first wedge 51 shown in FIGS. 10 through 12; thus, like reference numbers can be used, with the corresponding features of the variant first wedge 51' denoted with a "prime" notation. The primary difference in the variant first wedge 51' can be that the external face 138' of the first wedge body 128' is a first external face 138' that is defined by a transversely external one of the anterior and posterior arms 160', 162'. Additionally, the opposite (i.e., transversely internal) one of the arms 160', 162' can define a second external face 139' that is recessed from the first external face 138' in the internal longitudinal direction $L_1$.

The first external face 138' of the first wedge 51' can abut the proximal side 112 of the head 110, and the second external face 139' can abut the proximal face 90 of the first transverse protrusion 82 of the superior plate body 26 (FIG. 30). Thus, the proximal face 90 of the first transverse protrusion 82 can be termed an abutment surface of the superior plate body 26. Such a configuration can add stability to the implant 10 at least during expansion, contraction, and/or lordotic angulation of the implant 10. In other embodiments, however, the first wedge 51 of the distal wedge assembly 126 can be virtually identical to the first wedge 51 of the proximal wedge assembly 124. As with the first wedge 51, the variant 51' can be characterized as a "support member" or "support wedge" and can optionally be rigidly fixed to the inferior plate body 24 by welding, brazing, adhesives, or mechanical fasteners. It is to be appreciated that the variant first wedge 51' of the anterior actuation assembly 94 can be a substantial mirror image of its counterpart in the posterior actuation assembly 96 about a vertical-longitudinal plane positioned between the actuation assemblies 94, 96.

Referring now to FIGS. 16 through 18, the second wedge 52 can have a second wedge body 168 that defines an internal end 170 and an external end 172 spaced from the external end 172 along the longitudinal direction L. The second wedge body 168 can also define anterior and posterior side surfaces 174, 176 spaced from each other along the transverse direction T. The second wedge body 168 can also define an external face 178 at the external end 172. The external face 178 of the second wedge body 168 can extend along the vertical and transverse directions V, T and can be substantially planar, although other geometries are within the scope of the present disclosure. The second wedge body 168 can also define an upper base surface 180 and an opposed downward apex 182 spaced from the upper base surface 180 along the vertical direction V. The upper base surface 180 can extend along the longitudinal direction L between the internal and external ends 170, 172 of the body 168. The downward apex 182 can be located between the external and internal ends 170, 172 of the second wedge body 168 with respect to the longitudinal direction L.

The upper base surface 180 can be configured to engage the base surface 68 of the respective anterior or posterior channel 56, 58 of the superior plate body 26. Accordingly, the second wedge 52 can be characterized as "supporting" the superior plate body 26 and can be referred to herein as a "support member" or "support wedge." At least a portion of the upper base surface 180 can be substantially planar and can be configured to translate at least partially across the base surface 68 of the respective channel 56, 58 during expansion of the implant 10. Thus, the second wedge 52 can also be referred to as a "slider."

The second wedge body 168 can define a third or superior guide element, such as a guide protrusion 184, extending from the upper base surface 180 along the vertical direction V. A top surface 186 of the guide protrusion 184 can define a top-most portion of the second wedge 52. The top surface 186 can also define a top-most portion of the respective wedge assembly 124, 126. The guide protrusion 184 can be configured to translate within the guide slot 70 of the associated channel 56, 58 of the superior plate body 26. The guide protrusion 184 of the second wedge body 168 can have a design and function generally similar to those of the guide protrusion 144 of the first wedge body 128 set forth above. By way of non-limiting example, the guide protrusion 184 of the second wedge body 168 and the guide slot 70 of the associated channel 56, 58 of the superior plate body 26 can have corresponding dovetail profiles that interlock the second wedge 52 to the superior plate body 26. In this manner, guide protrusion 184 (which can also be characterized as a "retention" feature) can be longitudinally movable but substantially vertically immovable within the respective channel 56, 58 of the superior plate body 26. Additionally, the profiles of the guide protrusion 184 and of the plate guide slot 70 can allow the second wedge 52 and the superior plate body 26 to be rotationally interlocked with one another so that, for example, rotation of the second wedge 52 about the central shaft axis $X_1$ of the drive shaft 98 causes a substantially similar degree of rotation of the superior plate body 26 about the central shaft axis $X_1$, and vice versa.

The second wedge 52 can include one or more engagement elements configured to engage portions of one or more of the other wedges of the associated wedge assembly 124, 126. By way of non-limiting example, the second wedge body 168 can define a second inclined surface, or ramp 188, extending from the external face 178 to the downward apex 182, and a third inclined surface, or ramp 190, extending from the downward apex 182 to the internal end 170 of the second wedge body 168. The internal end 170 of the second wedge body 168 can define a shared edge between the upper base surface 180 and the third ramp 190. The second wedge 52 can be oriented in each actuation assembly 94, 96 so that the second ramp 188 is inclined in the external longitudinal direction $L_E$ and the third ramp 190 is declined in the external longitudinal direction $L_E$ (and thus inclined in the internal longitudinal direction $L_I$). The second ramp 188 can be configured to engage the first ramp 148 of the first wedge body 128 during expansion of the implant 10. The third ramp 190 can be configured to engage a portion of another wedge of the respective wedge assembly 124, 126, such as the third wedge 53, for example.

The second ramp 188 can optionally be substantially parallel with the first ramp 148 of the first wedge body 128. The second ramp 188 can be oriented at a second incline angle $\alpha_2$ in a range of about 10 degrees and about 60 degrees with respect to the longitudinal direction L (FIG. 18). In other embodiments, the second incline angle $\alpha_2$ can be in the range of about 20 degrees and about 40 degrees with respect to the longitudinal direction L. In further embodiments, the second incline angle $\alpha_2$ can be in the range of about 25 degrees and about 35 degrees with respect to the longitudinal direction L. In additional embodiments, the second incline angle $\alpha_2$ can be less than 10 degrees or greater than 60 degrees with respect to the longitudinal direction L.

The third ramp 190 can be oriented at a third incline angle $\alpha_3$ in the range of about 10 degrees and about 60 degrees with respect to the longitudinal direction L. In other embodiments, the third incline angle $\alpha_3$ can be in the range of about 20 degrees and about 40 degrees with respect to the longitudinal direction L. In further embodiments, the third incline angle $\alpha_3$ can be in the range of about 25 degrees and about 35 degrees with respect to the longitudinal direction L. In additional embodiments, the third incline angle $\alpha_3$ can be less than 10 degrees or greater than 60 degrees with respect to the longitudinal direction L.

The second wedge 52 can include a fourth guide feature, such as a guide slot 192, configured to guide relative motion between the second wedge 52 and another wedge of the associated wedge assembly 124, 126, such as the third wedge 53, for example. The guide slot 192 can be recessed into the second wedge body 168 from the third ramp 190 and can separate the third ramp 190 into anterior and posterior portions 194, 196, which can be characterized as "rails." The guide slot 192 can extend parallel with the third ramp 190 and can have a geometry configured to guide movement of, and optionally interlock with, an associated guide element of the third wedge 53. As shown, the guide slot 192 can have a dovetail profile, and can be configured similarly to the guide slot 150 of the first wedge body 128, as set forth above, although other geometries are within the scope of the present disclosure. The guide slot 192 can extend from a guide slot opening 198 at the upper base surface 180 to a stop feature 200 configured to prevent the guide element of the third wedge 53 from moving beyond the stop feature 200 along the external longitudinal direction $L_E$. The stop feature 200 can be spaced from the downward apex 182 in the internal longitudinal direction $L_I$. Thus, the guide slot 192 can extend less than an entire length of the third ramp 190.

The second wedge body 168 can define a channel 202 extending therethrough along the longitudinal direction L. The channel 202 of the second wedge body 168 can be configured similarly to the channel 158 of the first wedge body 128 set forth above. Thus, the second wedge body 168 can have a U-shaped profile in a vertical-transverse plane and can include anterior and posterior arms 204, 206 on opposite transverse sides of the channel 202. Additionally, the channel 202 can separate the second ramp 188 into anterior and posterior portions 208, 210, which can be characterized as "rails." The channel 202 can also intersect the guide slot 192 in a manner effectively converting a portion of the guide slot 192 into anterior and posterior slots 212, 214 defined in the anterior and posterior arms 204, 206, respectively.

Figure 19:
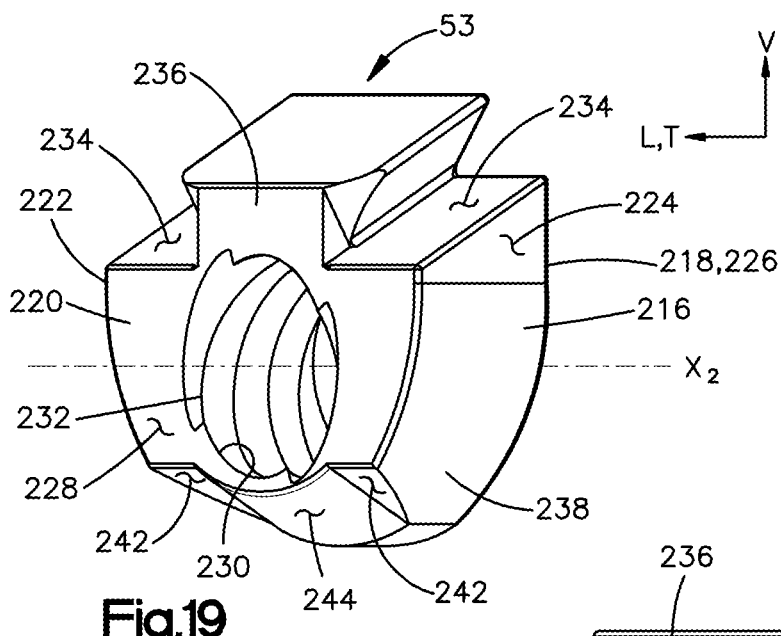
FIG. 19 is a perspective view of a third expansion wedge of the expansion assemblies shown in FIGS. 5 and 6.
Figure 20:
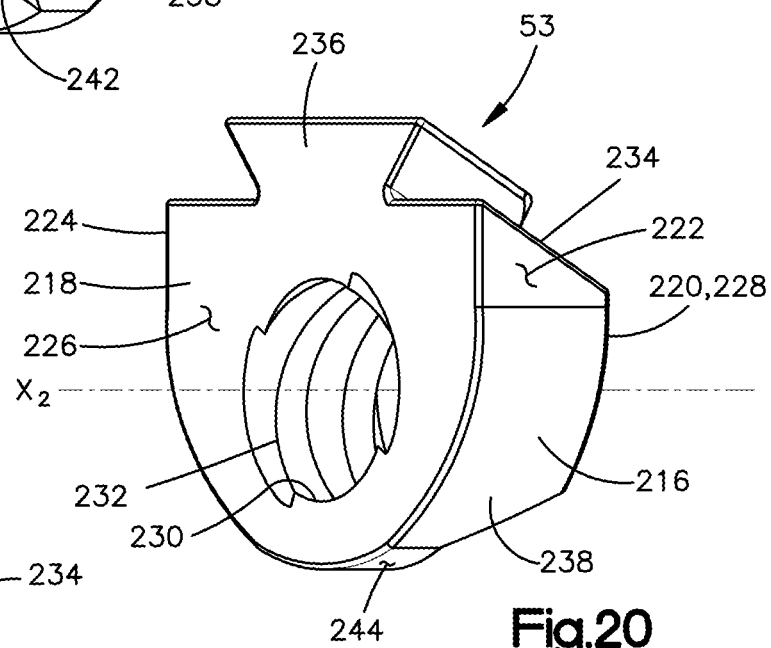
FIG. 20 is another perspective view of the third expansion wedge of FIG. 19.
Figure 21:
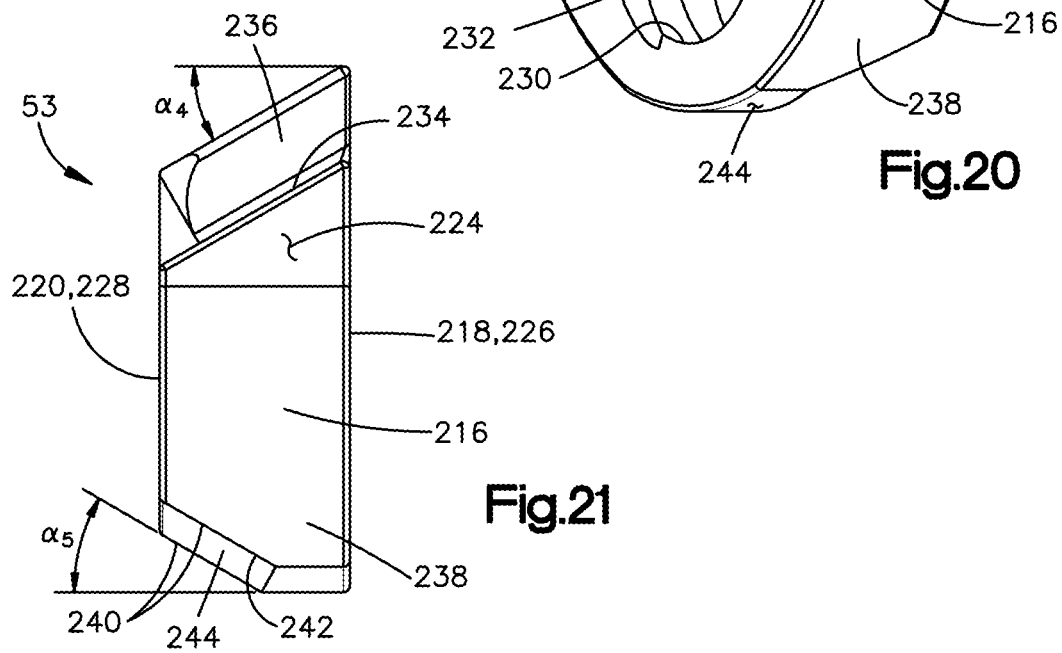
FIG. 21 is a side view of the third expansion wedge of FIG. 19.
Figure 22:
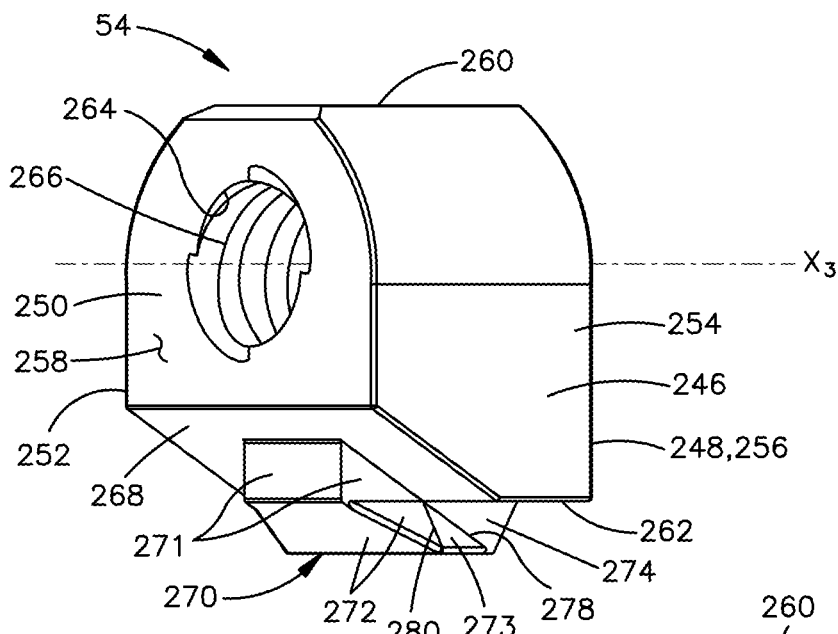
FIG. 22 is a perspective view of a fourth expansion wedge of the expansion assemblies shown in FIGS. 5 and 6.
Figure 23:
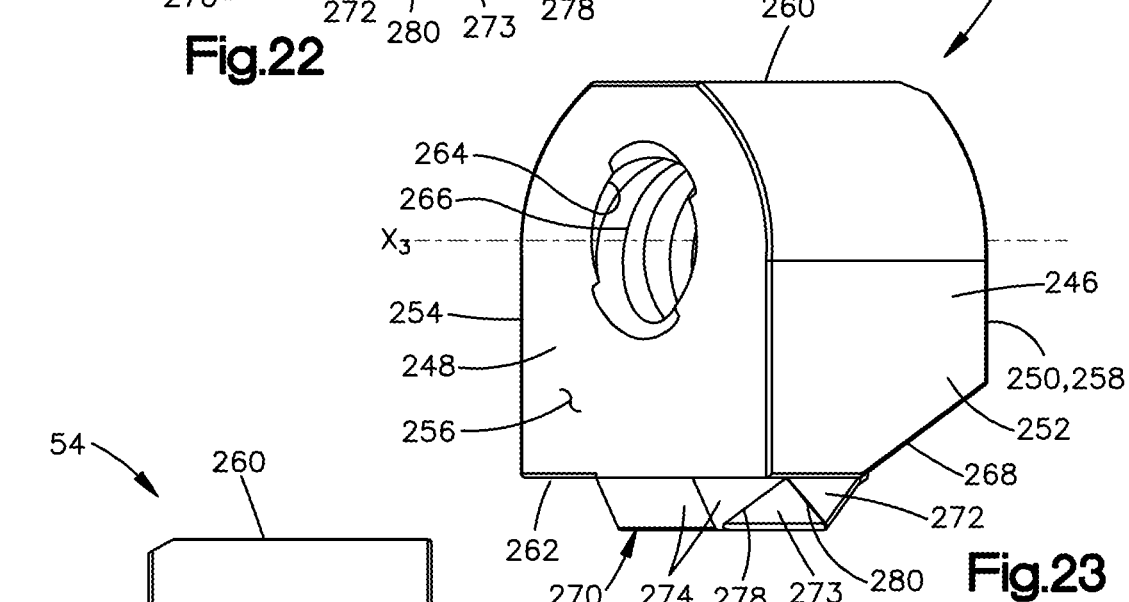
FIG. 23 is another perspective view of the fourth expansion wedge of FIG. 22.
Figure 24:
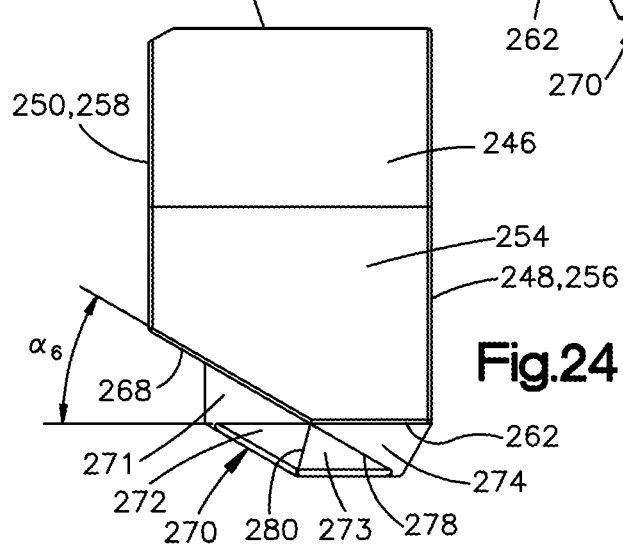
FIG. 24 is a side view of the fourth expansion wedge of FIG. 22.

Referring now to FIGS. 19 through 21, the third wedge 53 can have a third wedge body 216 that defines an internal end 218 and an external end 220 spaced from the internal end 218 along the longitudinal direction L. The third wedge body 216 can also define anterior and posterior side surfaces 222, 224 spaced from each other along the transverse direction T. The third wedge body 216 can also define an internal face 226 at the internal end 218 thereof and an external face 228 at the external end 220. The internal and external faces 226, 228 of the third wedge body 216 can each extend along the vertical and transverse directions V, T and can each be substantially planar, although other geometries are within the scope of the present disclosure. The third wedge body 216 can define a central bore 230 extending along a central bore axis $X_2$. The central bore 230 can be a through bore, and the central bore axis $X_2$ can extend along the longitudinal direction L. The central bore 230 can define threading 232 that is configured to engage at least one of the proximal and distal threaded portions 104, 106 of the drive shaft 98 so that rotation of the drive shaft 98 threadedly translates the third wedge 53 along the longitudinal direction L. Accordingly, the central bore axis $X_2$ can be coextensive with the central shaft axis $X_1$. The third wedge body 216 can also be configured to rotate about the central bore axis $X_2$, as set forth in more detail below.

The third wedge 53 can include one or more engagement elements configured to engage portions of one or more of the other wedges of the associated wedge assembly 124, 126, such as the second and fourth wedges 52, 54. For example, the internal face 226 of the third wedge 53 can be configured to engage (such as by abutting) a portion of the fourth wedge 54. Additionally, the third wedge body 216 can define a fourth inclined surface, or ramp 234, located at an upper side of the body 216. The fourth ramp 234 can extend between the internal and external faces 226, 228 along the longitudinal direction L. The fourth ramp 234 can be declined in the external longitudinal direction $L_E$ (and thus inclined in the internal longitudinal direction $L_I$).

The fourth ramp 234 can be configured to engage the third ramp 188 of the second wedge body 168, including during expansion of the implant 10. The fourth ramp 234 can optionally be substantially parallel with the third ramp 190 of the second wedge body 168. The fourth ramp 234 can be oriented at a fourth incline angle $\alpha_4$ in a range of about 10 degrees and about 60 degrees with respect to the longitudinal direction L (FIG. 21). In other embodiments, the fourth incline angle $\alpha_4$ can be in the range of about 20 degrees and about 40 degrees with respect to the longitudinal direction L. In further embodiments, the fourth incline angle $\alpha_4$ can be in the range of about 25 degrees and about 35 degrees with respect to the longitudinal direction L. In additional embodiments, the fourth incline angle $\alpha_4$ can be less than 10 degrees or greater than 60 degrees with respect to the longitudinal direction L.

The third wedge 53 can include a fifth guide element, such as a guide protrusion 236, configured to guide motion between the third wedge 53 and the second wedge 52. For example, the guide protrusion 236 of the third wedge 53 can extend vertically from the fourth ramp 234 and can be configured to translate within the guide slot 192 of the second wedge 52. The guide protrusion 236 can be cooperatively shaped with the guide slot 192 in a manner preventing the guide protrusion 236 from exiting the guide slot 192, at least in a direction orthogonal to the third ramp 190. For example, the guide protrusion 236 and the guide slot 192 can have corresponding dovetail profiles in a vertical-transverse plane, as shown. In such an embodiment, the guide protrusion 236 can only enter and exit the guide slot 192 through the guide slot opening 198. Additionally, the profiles of the guide slot 192 and the guide protrusion 236 can allow the second and third wedges 52, 53 to be rotationally interlocked with one another so that, for example, rotation of the third wedge 53 about the central bore axis $X_2$ causes a substantially similar degree of rotation of the second wedge 52 about the central bore axis $X_2$.

The third wedge 53 can have a geometry configured to avoid contact with the first wedge 51 during relative movement between the first and third wedges 51, 53. For example, the third wedge body 216 can have a rounded underside 238 configured so as not to contact or otherwise directly engage or interfere with the first ramp 148 or the anterior and posterior arms 160, 162 of the first wedge body 128 during translational and rotational movement of the third wedge body 216 over the first wedge body 128. Additionally, the underside 238 can define a fifth inclined surface, or ramp 240, that is oriented at a fifth incline angle as that is substantially parallel with the first incline angle $\alpha_1$ of the first ramp 148. The fifth ramp 240 can be configured so as not to contact the first ramp 148. For example, the fifth ramp 240 can include a pair of planar portions 242 positioned on opposite transverse sides of a rounded portion 244. The rounded portion 244 can be configured to extend within the guide slot 150 of the first wedge body 128 without contacting the first ramp 148 or any other portion of the first wedge body 128 during translational and rotational movement of the third wedge body 216 over the first wedge body 128. Additionally, the planar portions 242 of the fifth ramp 240 can be remote from the first ramp 148 or any other portion of the first wedge body 128 during movement of the third wedge body 216 over the first wedge body 128.

Referring now to FIGS. 22 through 25, the fourth wedge 54 can have a fourth wedge body 246 that defines an internal end 248 and an external end 250 spaced from the internal end 248 along the longitudinal direction L. The fourth wedge body 246 can also define anterior and posterior side surfaces 252, 254 spaced from each other along the transverse direction T. The fourth wedge body 246 can also define an internal face 256 at the internal end 248 thereof and an external face 258 at the external end 250. The internal and external faces 256, 258 of the fourth wedge body 246 can each extend along the vertical and transverse directions V, T and can each be substantially planar, although other geometries are within the scope of the present disclosure. The fourth wedge body 246 can include a top surface 260 and a bottom surface 262 opposite the top surface 260 with respect to the vertical direction V. The bottom surface 262 can also be referred to as a "base" surface of the fourth wedge 54, and can extend along the longitudinal and transverse directions L, T. The bottom surface 262 can optionally be planar. The fourth wedge body 246 can be rounded or chamfered between the top surface 260 and the side surfaces 252, 254 so as to avoid contacting or otherwise directly engaging or interfering with the third ramp 190 or any other portion of the second wedge body 168 during translational and rotational movement of the fourth wedge body 246 under the second wedge body 168, for example.

The fourth wedge body 246 can define a central bore 264 extending along a central bore axis $X_3$. The central bore 264 can be a through bore and can extend along the longitudinal direction L. The central bore axis $X_3$ of the fourth wedge body 246 can be coextensive with the central shaft axis $X_1$ of the drive shaft 98 and with the central bore axis $X_2$ of the third wedge body 216. The central bore 264 of the fourth wedge body 246 can define threading 266 that is configured to engage the same one of the proximal and distal threaded portions 104, 106 as the threading 232 of the third wedge body 216. In the illustrated embodiments, rotation of the drive shaft 98 can threadedly translate the third and fourth wedges 53, 54 together along the longitudinal direction L at the same rate. However, in other embodiments, the third and fourth wedges 53, 54 of each wedge assembly 124, 126 can move at different rates and/or in opposite directions along the drive shaft 98.

The fourth wedge 54 can include one or more engagement elements configured to engage portions of at least one of the other wedges of the associated wedge assembly 124, 126, such as the third wedge 53. For example, the external face 258 of the fourth wedge body 246 can be characterized as an engagement element because it can be configured to abut the internal face 226 of the third wedge body 216. The external face 258 of the fourth wedge body 54 can optionally be configured to abut the internal face 226 of the third wedge body 216 in a manner ensuring that the third and fourth wedge bodies 216, 158 translate along the respective threaded portion 104, 106 of the drive shaft 98 at the same rate. In this manner, the fourth wedge 54 can be characterized as a "pusher" or a "pusher member" that effectively pushes the third wedge 53 in the external longitudinal direction $L_E$. Additionally, it is to be appreciated that the third and fourth wedges 53, 54 can collectively be referred to as an "expansion wedge", with the third wedge 53 being referred to as a "first member" or "first portion" of the expansion wedge, and the fourth wedge 54 being referred to as a "second member" or "second portion" of the expansion wedge. Additionally, each of the third and fourth wedges 53, 54 can be referred to individually as an "expansion wedge."

The fourth wedge body 246 can also define a sixth inclined surface, or ramp 268, adjacent the bottom surface 262 of the body 246. The sixth ramp 268 can extend between the bottom surface 262 and the external face 256 of the fourth wedge body 246 with respect to the longitudinal direction L. The sixth ramp 268 can be inclined in the external longitudinal direction $L_E$ (and thus declined in the internal longitudinal direction $L_I$). The sixth ramp 268 can be configured to engage the first ramp 148 of the first wedge body 128 during expansion of the implant 10. The sixth ramp 268 can optionally be substantially parallel with the first ramp 148. The sixth ramp 268 can be oriented at a sixth incline angle $\alpha_6$ in a range of about 10 degrees and about 60 degrees with respect to the longitudinal direction L (FIG.

24). In other embodiments, the sixth incline angle $\alpha_6$ can be in the range of about 20 degrees and about 40 degrees with respect to the longitudinal direction L. In further embodiments, the sixth incline angle $\alpha_6$ can be in the range of about 25 degrees and about 35 degrees with respect to the longitudinal direction L. In additional embodiments, the sixth incline angle $\alpha_6$ can be less than 10 degrees or greater than 60 degrees with respect to the longitudinal direction L.

The fourth wedge 54 can include a sixth guide element, such as a guide protrusion 270, configured to guide motion between the fourth wedge 54 and each of the inferior plate 12 and the first wedge 51. The guide protrusion 270 can extend from each of the bottom surface 262 and the sixth ramp 268. The guide protrusion 270 can be configured such that, in one phase of expansion of the implant 10, the protrusion 270 can translate within the guide slot 70 of the respective channel 68 of the inferior plate body 24 and, during another phase of expansion, the protrusion 270 can translate within the guide slot 150 of the first wedge 51.

The guide protrusion 270 of the fourth wedge body 246 can include one or more portions configured to selectively engage guide features of the inferior plate body 24 and guide features of the first wedge 51. For example, in the non-limiting example shown in FIGS. 22 through 24, the guide protrusion 270 can include a first portion 271, a second portion 272, a third portion 273, and a fourth portion 274. The first portion 271 can extend from the sixth ramp 268. The fourth portion 274 can extend from the bottom surface 262. The second portion 272 can be located underneath the first portion 271. The third portion 273 can be generally underneath the fourth portion 274. The first and fourth portions 271, 274 can each have a rectangular profile in the vertical-transverse plane. The second and third portions 272, 273 can each have a dovetail profile in the vertical-transverse plane. On each of the anterior and posterior sides 252, 254 of the fourth wedge body 246, an edge 276 between the first and second portions 271, 272 can be parallel with the bottom surface 262. Also on each side 252, 254, an edge 278 between the third and fourth portions 273, 274 can be parallel with the sixth ramp 268. The second portion 272 can taper transversely inward toward the first portion 271 from an edge 280 between the second and third portions 272, 273. The third portion 273 can taper transversely inward toward the fourth portion 274 from the edge 280 between the second and third portions 272, 273.

As shown in FIG. 26, during a first phase of expansion of the implant 10, the second, third and fourth portions 272, 273, 274 of the guide protrusion 270 of the fourth wedge 54 can be positioned within the respective plate guide slot 70 while the first portion 271 is positioned external of the plate guide slot 70. As shown in FIG. 27, at the conclusion of the first phase, which can also be considered the commencement of a second phase of expansion, the protrusion 270 can be simultaneously positioned in both the plate guide slot 70 and the guide slot 150 of the first wedge 51. The geometry of the protrusion 270 allows it to transition from the plate guide slot 70 to the first wedge guide slot 150, and to remain within the first wedge guide slot 150 during the second phase of expansion, as shown in FIG. 28. During the second phase, the first, second, and third portions 271, 272, 273 of the guide protrusion 270 can be positioned within the guide slot 150 of the first wedge 51 while the fourth portion 274 can be external of the guide slot 150.

It is to be appreciated that the dovetail profile of the guide protrusion 270, particularly at the edge 280 between the second and third portions 272, 273, can substantially match the dovetail profiles of the guide slots 70 of each channel 62, 64 as well as the guide slot 102 of the first wedge 51. The second portion 272 of the guide protrusion 270 can be configured to allow the guide protrusion 270 to transfer from the guide slot 70 of the inferior plate body 24 to the guide slot 150 of the first wedge 51 between the first and second phases. The third portion 273 of the guide protrusion 270 can be configured to allow the guide protrusion 270 to transfer from the guide slot 150 of the first wedge 51 to the guide slot 70 of the inferior plate body 24 during an optional reverse expansion process (i.e., during a collapsing or "contracting" process) of the implant 10, as set forth in more detail below.

The third portion 273 of the guide protrusion 270, particularly at the edge 280 between the second and third portions 272, 273, can be cooperatively shaped with the guide slot 150 of the first wedge 51 in a manner preventing the guide protrusion 270 from exiting the guide slot 150, at least in a direction orthogonal to the first ramp 148 and optionally in any direction except a direction parallel with the first ramp 148. In the illustrated embodiment, the guide protrusion 270 can enter and exit the guide slot 150 only at the internal end 130 (through the guide slot opening 198) or optionally at the external end 132 of the first wedge body 128.

Additionally, the second portion 272 of the guide protrusion 270, particularly at the edge 280 between the second and third portions 272, 273, can be cooperatively shaped with the guide slot 70 of the respective channel 62, 64 of the inferior plate body 24 in a manner preventing the guide protrusion 270 from exiting the guide slot 70, at least in a direction orthogonal to the channel base surface 68 and optionally in any direction except the longitudinal direction L or a direction parallel with the first ramp 148. Additionally, the profiles of the guide protrusion 270 and of the plate guide slot 70 can allow the inferior plate body 24 to be rotationally interlocked with the fourth wedge 54 when the guide protrusion 270 is within the plate guide slot 70 (FIG. 26) so that, for example, the fourth wedge 54 and the inferior plate body 24 can maintain the same angular position about the central shaft axis $X_1$. Because the first wedge 51 can be rotationally interlocked with the inferior plate body 24 (FIG. 40), and the fourth wedge 54 can be rotationally interlocked with either the inferior plate body 24 or with the first wedge 51 (FIGS. 26 through 28), the inferior plate body 24 can thus be rotationally interlocked with both of the first and fourth wedges 51, 54 during all phases of expansion.

It is to be appreciated that, in the illustrated embodiment, the second, third and fourth wedges 52, 53, 54 of the proximal wedge assembly 124 can be substantially similar, or even virtually identical, to their respective counterparts in the distal wedge assembly 126. However, in other embodiments, one or more of the second, third and fourth wedges 52, 53, 54 of the proximal wedge assembly 124 can be configured differently than their respective counterparts in the distal wedge assembly 126.

Figure 29:
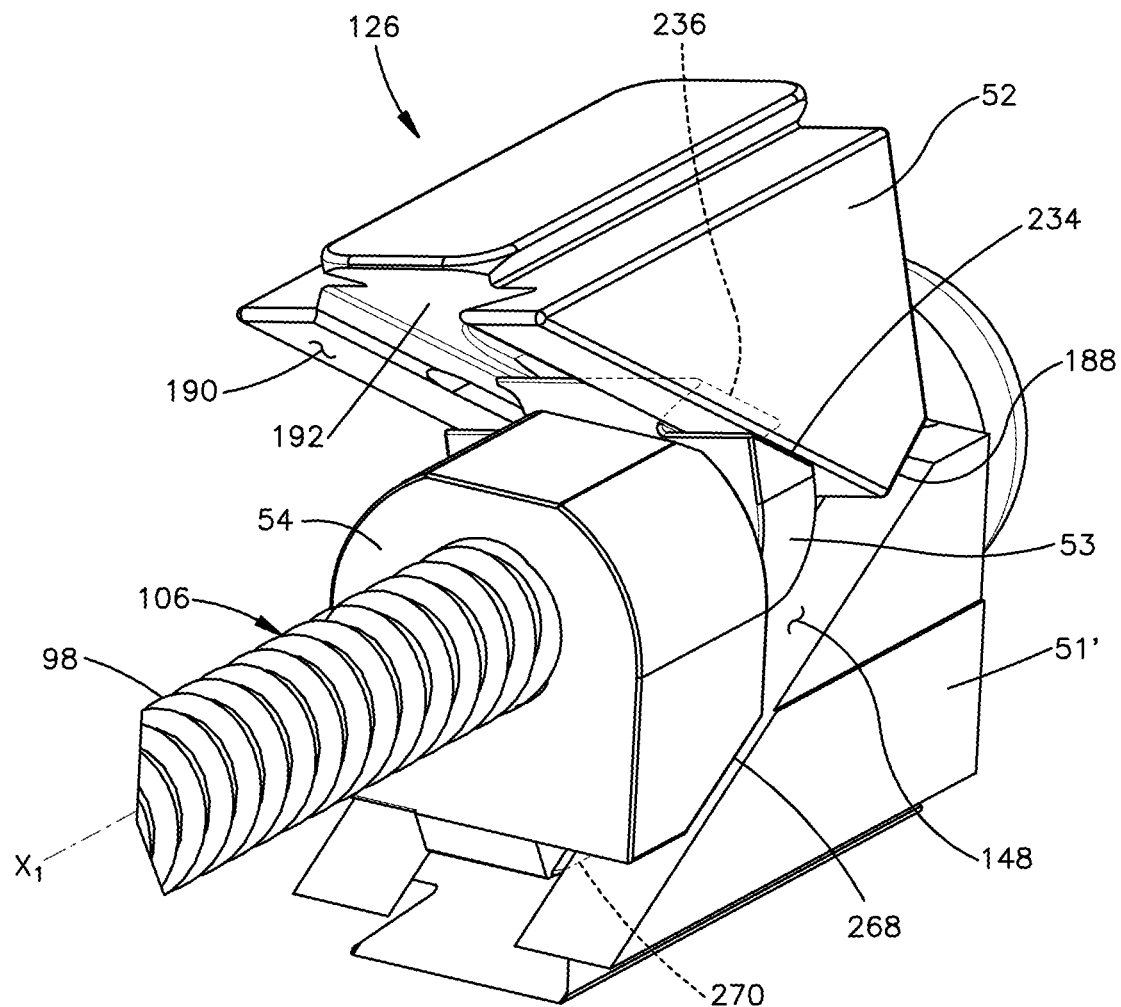
FIG. 29 is a perspective view of an internal end of an expansion assembly of FIGS. 5 and 6, wherein the expansion assembly is shown in an expanded and lordotic configuration.

Referring now to FIG. 29, a distal wedge assembly 126 is illustrated during the second phase of expansion. The profiles of the guide slot 192 of the second wedge 52 and the guide protrusion 236 of the third wedge can allow the second wedge 52 to be rotationally interlocked with the third wedge 53 as the third wedge 53 rotates relative to the fourth wedge 54 about the axis $X_1$ of the drive shaft 98, as set forth above. Additionally, as also set forth above, the profiles of the guide slot 150 of the first wedge 51 and the guide protrusion 270 of the fourth wedge 54 can allow the first and fourth wedges 51, 54 to be rotationally interlocked with one another when the guide protrusion 270 is within the guide slot 150 so that, for example, the first and fourth wedges 51, 54 maintain the same angular position about the central shaft axis $X_1$ or, in other embodiments, so that the first and fourth wedges 51, 54 rotate by the same degree about the central shaft axis $X_1$ during operation of the implant 10.

Referring now to FIG. 30, the wedges 51, 52, 53, 54 of each wedge assembly 124, 126 can have telescopic mobility in the longitudinal and vertical directions L, V. It is to be appreciated that, when the implant 10 is in the collapsed configuration, each of the anterior and posterior actuation assemblies 94, 96, and each of the proximal and distal wedge assemblies 124, 126 can also be considered as being in its respective collapsed configuration. For purposes of comparison, FIG. 30 depicts the proximal wedge assembly 124 in the collapsed configuration while the distal wedge assembly 124 is depicted in the fully expanded configuration. Each wedge assembly 124, 126 can define a length, measured from the external face 138 of the first wedge 51 to the internal face 256 of the fourth wedge 54 along the longitudinal direction L, and a height, measured from the bottom surface 146 of the guide protrusion 144 of the first wedge 51 to the top surface 186 of the guide protrusion 184 of the second wedge 122 along the vertical direction V. In the collapsed configuration, each wedge assembly 124, 126 can define a collapsed length $L_1$ and a collapsed height $H_1$. In the fully expanded configuration, each wedge assembly 124, 126 can define an expanded length $L_2$ that is less than the collapsed length $L_1$, and an expanded height $H_2$ that is greater than the collapsed height $H_1$. Stated differently, each wedge assembly 124, 126 can decrease in length as it increases in height. The ratio of the expanded height $H_2$ to the collapsed height $H_1$ can be in the range of about 1.5:1 to 3.5:1, by way of non-limiting example. Accordingly, the vertical distance D between the bone-contacting surfaces 28, 30 (FIG. 31) can also increase by a similar margin during expansion of the implant 10. For example, the vertical distance D can increase by a factor in the range of about 1.05 and about 3.0 from the collapsed configuration to the fully expanded configuration, by way of non-limiting example.

Operation of the implant 10, including expansion and lordosis, will now be discussed with reference to FIGS. 31 through 41, beginning with the implant in the collapsed configuration, as shown in FIG. 31.

Referring now to FIG. 31, while the posterior actuation assembly 96 is depicted, it is to be appreciated that the following description can also apply to the corresponding components of the anterior actuation assembly 94. When the implant 10 is in the collapsed configuration, the internal contact surfaces 46 of the inferior and superior plate bodies 24, 26 can abut one another. Additionally, when collapsed, each actuation assembly 94, 96 can be disposed substantially entirely within the associated compartment 60, 62 (FIG. 2) defined by the overlying channels 56, 58 of the plates 12, 18. The proximal end 120 of the nut socket 116 can be generally aligned with the proximal end 12 of the implant 10 along the transverse direction T. The drive shaft 98 can extend along the longitudinal direction L through the channels 56, 58. One or both of the distal end 114 of the head 110 and the distal end 102 of the drive shaft 98 can abut or be adjacent to the proximal face 90 of the second transverse protrusion 84 of the superior plate body 26. The proximal end 112 of the head 110 can abut or be adjacent to the distal face 92 of the first transverse protrusion 82 of the superior plate body 26. In this manner, the head 110 can be aligned with the transverse wall 76 of the inferior plate body 24 along the transverse direction T.

With reference to the proximal wedge assembly 124 in the collapsed configuration, the external face 138 of the first wedge 51 can abut or be adjacent to the distal end 122 of the nut socket 116. The bottom base surface 142 of the first wedge 51 can abut the base surface 68 of the posterior channel 58 of the inferior plate body 24 and the guide protrusion 144 of the first wedge 51 can be received within the guide slot 70 of the posterior channel 58 of the inferior plate body 24. The proximal threaded portion 104 of the drive shaft 98 can extend through the U-shaped channel 158 of the first wedge 51.

The second wedge 52 can be positioned such that the second ramp 188 abuts the first ramp 148 at a location adjacent the internal end 130 of the first wedge 51. The upper base surface 180 of the second wedge 52 can abut the base surface 68 of the posterior channel 58 of the superior plate body 26 and the guide protrusion 184 of the second wedge 52 can be received within the guide slot 70 of the posterior channel 58 of the superior plate body 26. The proximal threaded portion 104 of the drive shaft 98 can extend through the U-shaped channel 202 of the second wedge 52.

The third wedge 53 can be positioned such that the fourth ramp 234 thereof abuts the third ramp 190 of the second wedge 52 at a location adjacent the internal end 170 thereof. The guide protrusion 236 of the third wedge 53 can be received within the guide slot 192 of the second wedge 52. The drive shaft 98 can extend through the central bore 230 of the third wedge 53, with the threading 232 thereof engaged with the proximal threaded portion 104 of the drive shaft 98.

The fourth wedge 54 can be positioned such that the external face 258 thereof abuts or is adjacent to the internal face 226 of the third wedge 53. The internal face 256 of the fourth wedge 54 can be positioned at or adjacent the intermediate portion 108 of the drive shaft 98 (i.e., the internal end of the proximal threaded portion 104). The bottom surface 262 of the fourth wedge 54 can abut the base surface 68 of the posterior channel 58 of the inferior plate body 24 and the guide protrusion 270 of the fourth wedge 54 can be received within the guide slot 70 of the posterior channel 58 of the inferior plate body 24. The drive shaft 98 can extend through the central bore 264 of the fourth wedge 53, with the threading 266 thereof engaged with the proximal threaded portion 104 of the drive shaft 98.

It is to be appreciated that, as set forth above, the distal wedge assembly 126 can effectively be a substantial mirror image of the proximal wedge assembly 124 about a vertical-transverse plane positioned at the intermediate portion 108 of the drive shaft 98. Thus, the relative positions of the wedges 51', 52, 53, 54 of the distal wedge assembly 126 and the distal threaded portion 106 of the drive shaft 98 can be substantially similar to that of the proximal wedge assembly 124 and the proximal threaded portion 104 of the drive shaft. With regards to the variant of the first wedge 51', the first external face 138' thereof can abut or be adjacent the proximal end 112 of the head 110 (FIG. 5) while the second external face 139' of the first wedge 51' can abut or be adjacent to the proximal face 90 of the first transverse protrusion 82 of the superior plate body 26 (FIG. 4).

Figure 32:
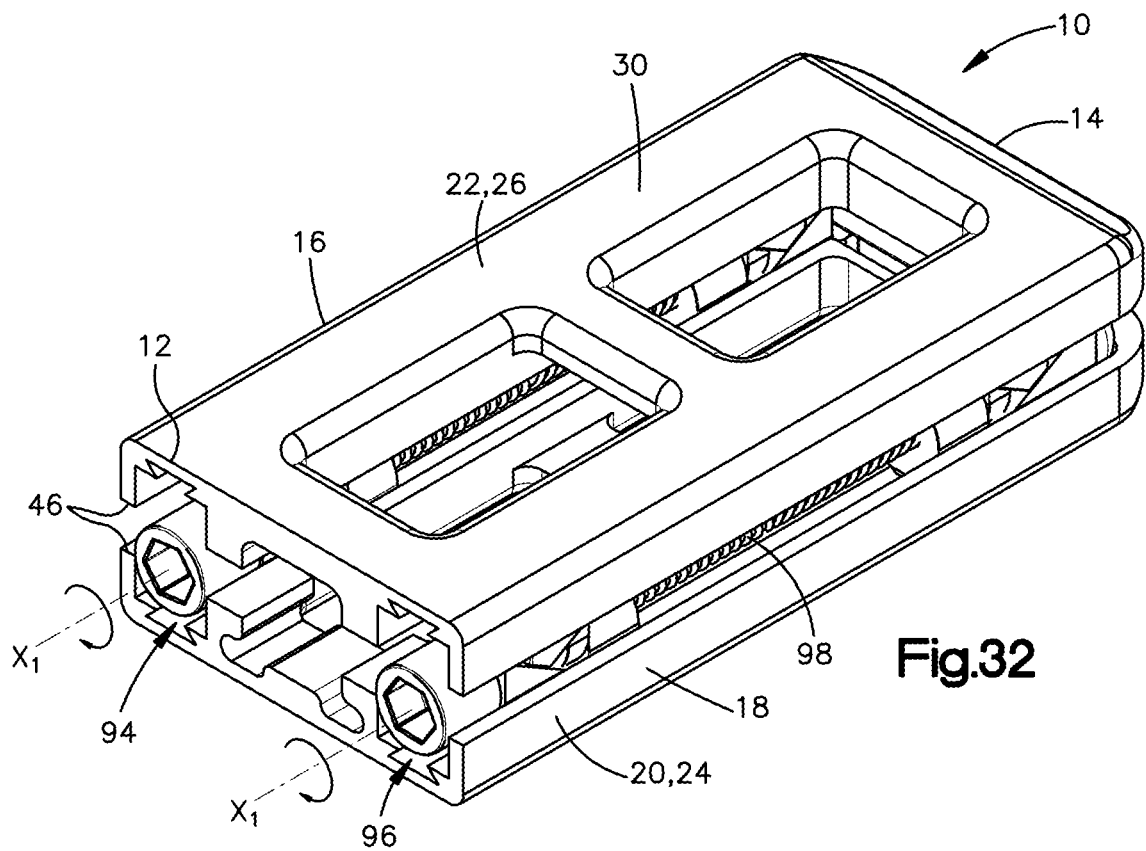
FIG. 32 is a perspective view of the implant of FIG. 1 in a partially expanded configuration.
Figure 33:
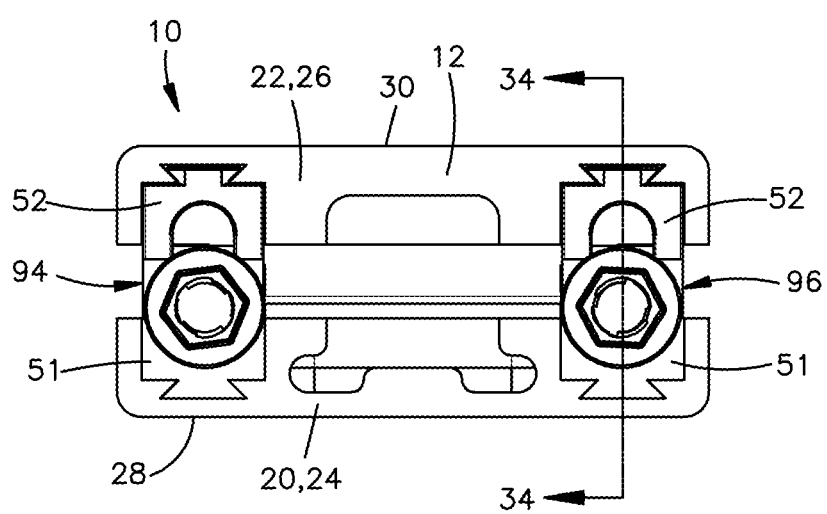
FIG. 33 is an end view of the implant shown in FIG. 32.

Expansion of the implant 10 between the collapsed configuration and a first partially expanded configuration, as shown in FIGS. 32 through 34, will now be discussed, according to an example mode of expansion. It is to be appreciated that, while FIGS. 32 through 34 depict the anterior and posterior actuation assemblies 94, 96 actuated concurrently so as to expand the implant 10 uniformly, each of the anterior and posterior actuation assemblies 94, 96 can be operated independently to provide non-uniform expansion or contraction of the implant 10 (i.e., lordosis).

During a first phase of expansion, the drive shaft 98 can be rotated about its central shaft axis $X_1$ in a first rotational direction (such as clockwise, for example) so that the proximal threaded portion 104 provides a first or proximal drive force $F_1$ in the external longitudinal direction $L_E$ thereof (i.e., the proximal direction) and the distal threaded portion 106 provides a second or distal drive force $F_2$ in the external longitudinal direction $L_E$ thereof (i.e., the distal direction). The threading 232, 178 of the central bores 146, 176 of the third and fourth wedges 53, 54, respectively, can engage the associated threaded portion 104, 106 of the drive shaft 98 in a manner transmitting the respective drive force $F_1$, $F_2$ to the third and fourth wedges 53, 54 causing the third and fourth wedges 53, 54 to translate in the external longitudinal direction $L_E$.

Referring to FIG. 34, as the third and fourth wedges 53, 54 translate, each of the following can occur: the bottom surface 262 of the fourth wedge 54 rides along the base surface 68 of the respective anterior channel 56, 58 of the inferior plate 20; the guide protrusion 270 of the fourth wedge 54 rides within the guide slot 70 of the respective channel 56, 58; the fourth ramp 234 of the third wedge 53 rides along the third ramp 190 of the second wedge 52; and the guide protrusion 236 of the third wedge 53 rides within the guide slot 192 of the second wedge 52. The vertical distance D between the inferior and superior bone-contacting surfaces 28, 30 can increase by a factor in the range of about 0.2 and about 1.0 as a result of the fourth ramp 234 riding along the third ramp 190. As the fourth ramp 234 rides along the third ramp 190, the first drive force $F_1$ can be conveyed at least to the second wedge 52 causing the second ramp 188 (not visible in FIG. 34) to ride along the first ramp 148 of the first wedge 51, further increasing the distance D between the bone-contacting surfaces 28, 30 along the vertical direction V by a factor in the range of about 0.2 to 1.0 (with respect to the collapsed distance D).

As the fourth ramp 234 rides along the third ramp 190 and as the second ramp 188 rides along the first ramp 148, the sixth ramp 268 of the fourth wedge 54 can approach the first ramp 148 of the first wedge 51. In the present example, the first phase of expansion can be complete when the sixth ramp 268 abuts the first ramp 148, at which point the protrusion 270 of the fourth wedge 54 can enter the opening 152 of the guide slot 150 of the first wedge 51 (FIG. 28). As set forth above, the geometry of the guide protrusion 270 of the fourth wedge 54 can allow the protrusion 270 to be simultaneously positioned within the plate guide slot 70 and the guide slot 150 of the first wedge 51 at the conclusion of the first phase of expansion (and at the commencement of the second phase of expansion).

At the conclusion of the first phase and commencement of the second phase of expansion, the external end 172 of the second wedge 52, as well as the entire second ramp 188, can be positioned intermediate the internal and external ends 130, 132 of the first wedge 51 with respect to the longitudinal direction L. Moreover, the entire fourth ramp 234 can be positioned intermediate the downward apex 182 and the internal end 170 of the second wedge 52, while the protrusion 236 of the third wedge 53 can be positioned intermediate the stop feature 200 and the opening 198 of the guide slot 192 of the second wedge 52, each with respect to the longitudinal direction L. It is to be appreciated that, while views of the internal end 90 of the first wedge 51 and the downward apex 182 and stop feature 200 of the second wedge 52 are each obstructed in FIG. 34, such features are visible in FIG. 31.

Figure 36:
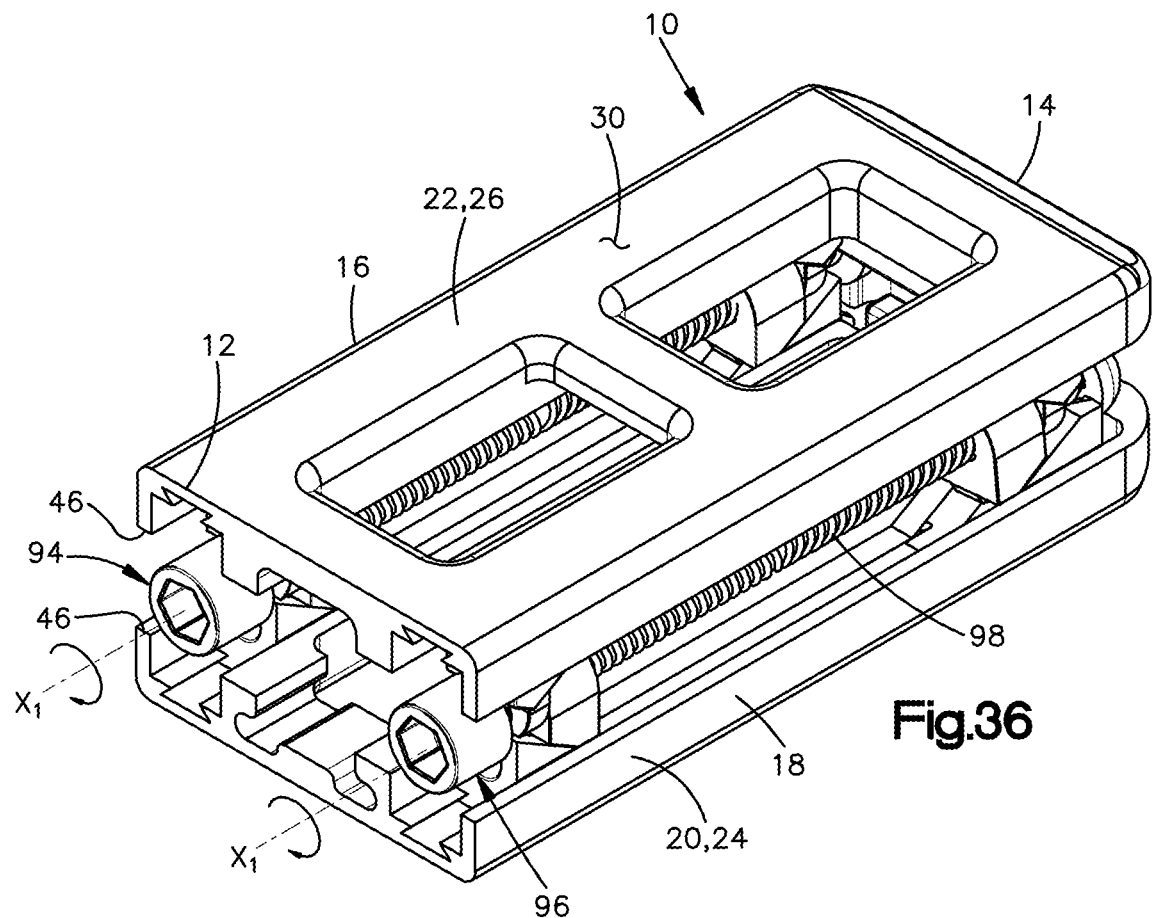
FIG. 36 is a perspective view of the implant shown in FIG. 35.
Figure 37:
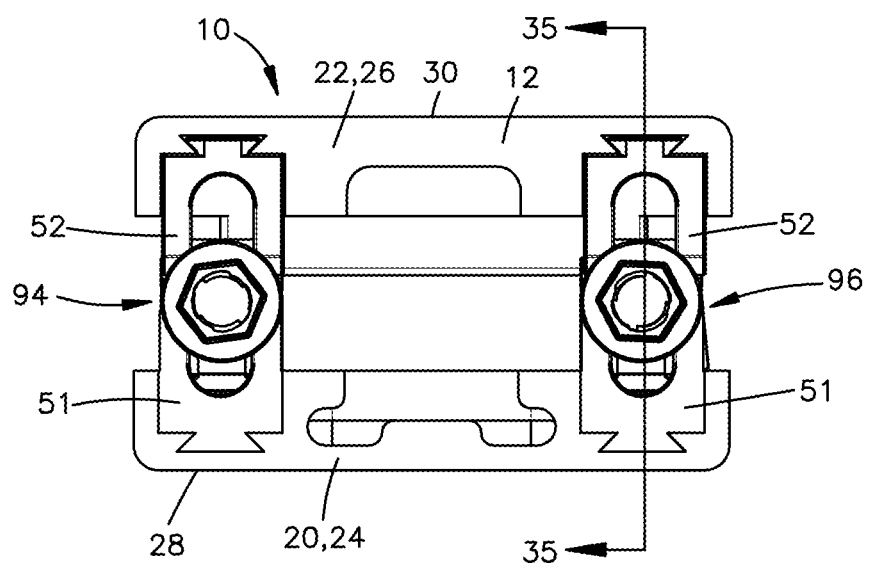
FIG. 37 is an end view of the implant shown in FIG. 36.

Expansion of the implant 10 between the first partially expanded configuration, as shown in FIGS. 32 through 34, and a fully expanded configuration, as shown in FIGS. 35 through 37, will now be discussed, according to the example mode of expansion.

Referring now to FIGS. 35 through 37, the implant 10 is shown uniformly expanded at the conclusion of the second phase of expansion, which can be commensurate with the fully expanded configuration. As above, it is to be appreciated that the anterior and posterior actuation assemblies 94, 96 can each be operated independently to provide non-uniform expansion or contraction of the implant 10 (i.e., lordosis) between the first partially expanded configuration and the fully expanded configuration.

Referring to FIGS. 35 through 37, during the second phase of expansion, the drive shaft 98 can be further rotated about its central shaft axis $X_1$ in the first rotational direction. The threading 232, 178 of the third and fourth wedges 53, 54, respectively, can continue to engage the associated threaded portion 104, 106 of the drive shaft 98 in a manner translating the third and fourth wedges 53, 54 further in the external longitudinal direction $L_E$. The second phase of expansion can be characterized as when the sixth ramp 268 rides along the first ramp 148, which yet further increases the distance D between the inferior and superior bone-contacting surfaces 28, 30.

As the fourth wedge 54 translates at the commencement of the second phase of expansion, the protrusion 270 can transition from the guide slot 70 of the channel 56, 58 of the inferior plate body 24 to the guide slot 150 of the first wedge 51. In particular, the geometry of the first, second, third and fourth portions 271, 272, 273, 274 of the protrusion 270 can engage the guide slot 150 of the first wedge 51 so that the protrusion 270 is caused to exit the plate guide slot 70 and to be received entirely within the guide slot 150 of the first wedge 51. Additionally, the fifth ramp 240 of the third wedge 53 can extend within the guide slot 150 of the first wedge 51 without contacting the first wedge body 128.

During at least a portion of the second phase of expansion, the sixth ramp 268 can ride along the first ramp 148 while the fourth ramp 234 rides along the third ramp 190, resulting in relative motion between the second wedge 52 and each of the third and fourth wedges 53, 54 along the longitudinal and vertical direction L, V. Such relative motion between the second wedge 52 and the third and fourth wedges 53, 54 during the second phase can cause the second ramp 188 to separate from, or otherwise become remote from, the first ramp 148 with respect to the vertical direction V. Additionally, such relative motion between the second wedge 52 and the third and fourth wedges 53, 54 can be initiated by a reactionary force imparted to at least one of the second, third, and fourth wedges 52, 53, 54. For example, the reactionary force can occur when a component of the implant 10, such as a stop feature in the channel 56, 58, the guide slot 70, or other portion of the plate body 24, 26, impedes motion of the second wedge 52 in the external longitudinal direction $L_E$. In another non-limiting example, the second and sixth ramps 124, 180 can ride along the first ramp 148 at or near the same rate until, in the proximal wedge assembly 124, the external face 178 of the second wedge 52 abuts the distal end 122 of the nut socket 116 while, in the distal wedge assembly 126, the external face 178 of second wedge 52 abuts the proximal face 90 of the first transverse protrusion 82. In each of the proximal and distal wedge assemblies 124, 126, the foregoing abutments can impede further movement of the second wedge 52 along the external longitudinal direction $L_E$ while the fourth ramp 234 continues to ride along the third ramp 190 and the sixth ramp 268 continues to ride along the first ramp 148, thus driving the second wedge 52 upward with respect to the first wedge 51.

In another non-liming example, the reactionary force can occur at the commencement of the second phase of expansion, causing the fourth ramp 234 to ride along the third ramp 190 as soon as the sixth ramp 268 rides along the first ramp 148. In such an example, in each of the proximal and distal wedge assemblies 124, 126, the fourth ramp 234 can ride along the third ramp 190 until the guide protrusion 236 of the third wedge 53 abuts the stop feature 200 of the guide slot 192 of the second wedge 52, after which the sixth ramp 268 can continue to ride along the first ramp 148 without any relative motion between the second wedge 52 and the third and fourth wedges 53, 54 along the longitudinal and vertical directions L, V. Thus, in each of the two preceding non-limiting examples, the second phase of expansion can include at least one portion or sub-phase that involves relative motion between the second wedge 52 and each of the third and fourth wedges 53, 54 with respect to the longitudinal and vertical directions L, V, and at least one other portion or sub-phase during which the second, third, and fourth wedges 52, 53, 54 are driven together along the longitudinal and vertical directions L, V without any relative motion therebetween.

In yet another non-limiting example, relative motion can occur between the second wedge 52 and each of the third and fourth wedges 53, 54 along the longitudinal and vertical directions L, V during substantially the entire second phase of expansion. In this example, in each of the proximal and distal wedge assemblies 124, 126, the reactionary force can occur at the commencement of the second phase of expansion, causing the fourth ramp 234 to ride along third ramp 190 and the guide protrusion 236 of the third wedge 53 to concurrently ride within the guide slot 192 as soon as the sixth ramp 268 rides along the first ramp 148. Furthermore, in this example, the guide protrusion 236 of the third wedge 53 can abut the stop feature 200 of the second wedge 52 substantially at the same time as the external face 178 of the second wedge 52 abuts the distal end 122 of the nut socket 116.

At the conclusion of the second phase of expansion, in the proximal wedge assembly 124, the external end 172 of the second wedge 52 can be substantially aligned with the external end 132 of the first wedge 51 along the vertical direction V, and, in the distal wedge assembly, the external end 172 of the second wedge 52 can be substantially aligned with the second external face 139' of the first wedge 51'. Additionally, in each wedge assembly 124, 126, the third and fourth wedges 53, 54 can each be entirely intermediate the internal and external ends 130, 132 of the first wedge 51 as well as the external and internal ends 170, 172 of the second wedge 52. Similarly, at the conclusion of the second phase of expansion, the downward apex 182 of the second wedge 52 can be spaced upward of the upward apex 140 of the first wedge 51.

Throughout expansion of the implant 10, the respective first wedges 51, 51' of the proximal and distal wedge assemblies 124, 126 can remain adjacent the external ends of the proximal and distal threaded portions 104, 106 of the drive shaft 98. Additionally, the second, third and fourth wedges 52, 53, 54 of each wedge assembly 124, 126 can move in the external longitudinal direction $L_E$ during expansion. Thus, the points of contact between the wedge assemblies 124, 126 and the superior and inferior plates 12, 28 are either initially located adjacent the proximal and distal ends 12, 14 of the implant 10 (as in the case of the first wedges 51, 51' coupled to the inferior plate 20) or move toward the proximal and distal ends 12, 14 of the implant 10 during expansion (as in the case of the second wedges 52 coupled to the superior plate 22). Such an arrangement provides enhanced support and stability to the implant 10 during expansion, particularly with respect to reactive forces, such as inner body forces, imparted to the implant 10 along the vertical direction V within the intervertebral space 5. However, it is to be appreciated that, in other embodiments (not shown), the respective first wedges 51, 51' of the proximal and distal wedge assemblies 124, 126 can be located adjacent the internal ends of the threaded portions 104, 106 of the drive shaft 98, and the second, third and fourth wedges 52, 53, 54 of each wedge assembly 124, 126 can move in the internal longitudinal direction $L_I$ during expansion.

Operation of the implant 10 to achieve lordosis will now be discussed.

Figure 38:
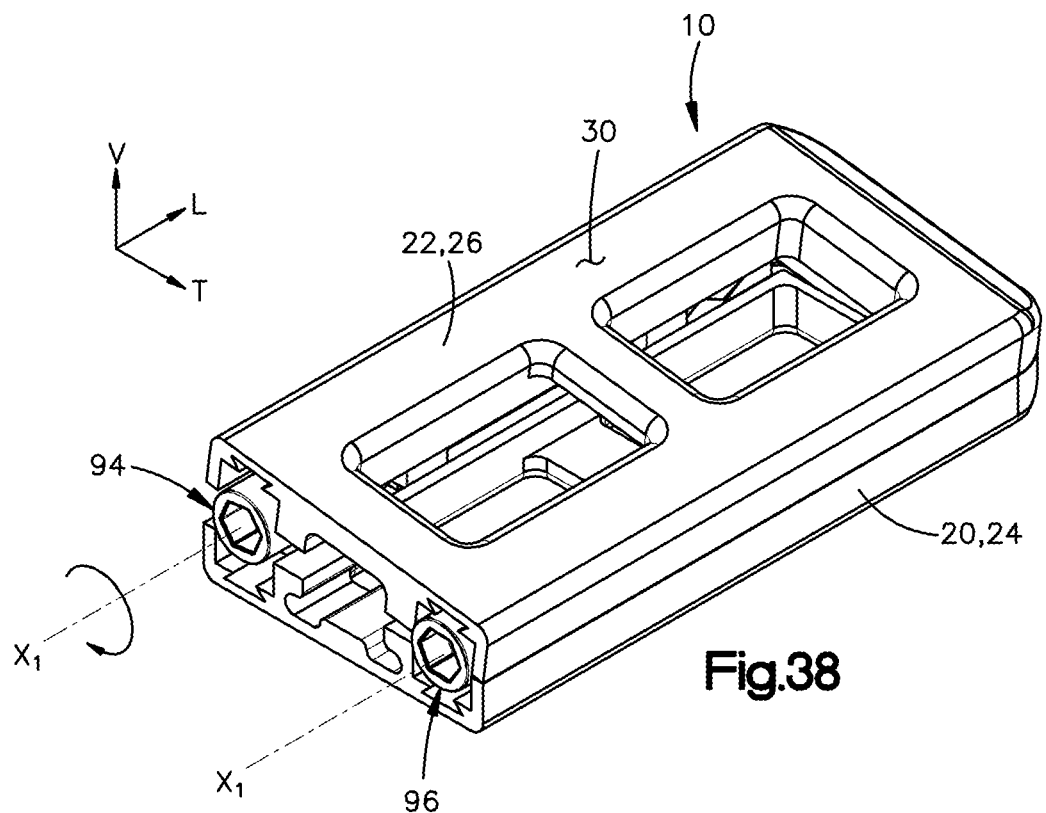
FIG. 38 is a perspective view of the implant of FIG. 1, shown in a partially expanded, lordotic configuration.
Figure 39:
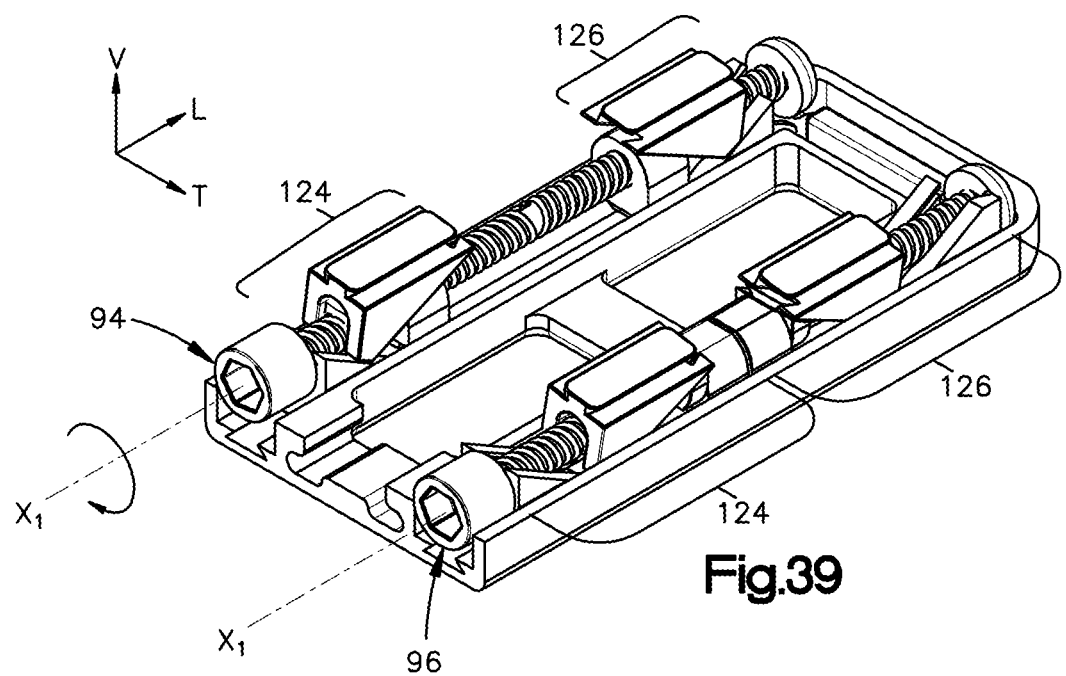
FIG. 39 is a perspective view of the implant of FIG. 38, shown with a bone plate removed for illustrative purposes.
Figure 40:
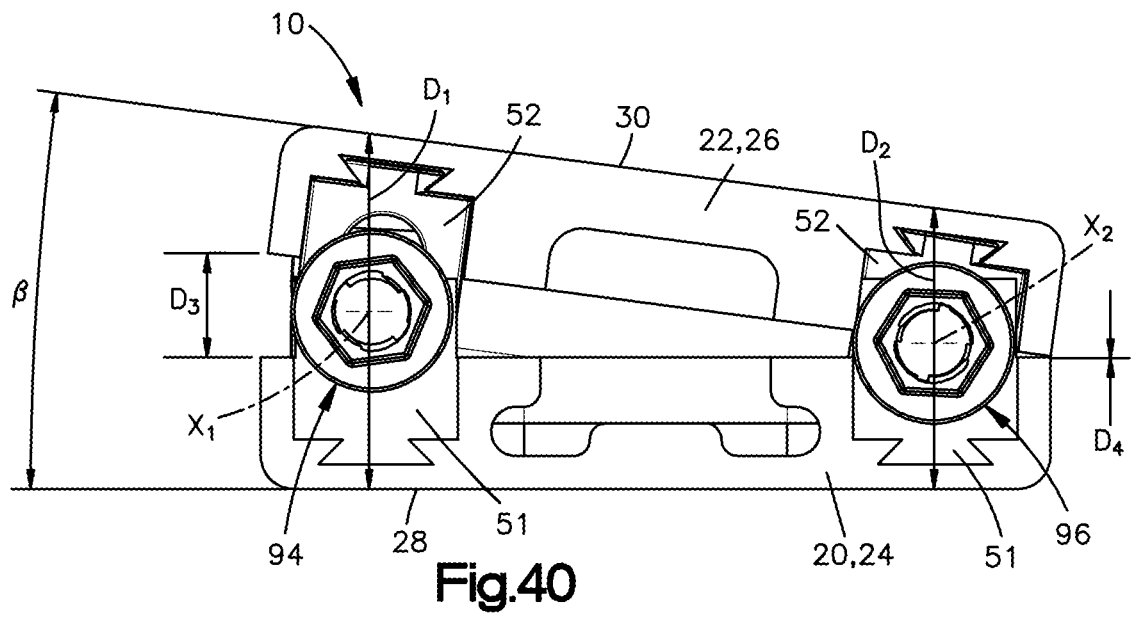
FIG. 40 is an end view of the implant of FIG. 38.

Referring now to FIGS. 38 through 40, the anterior and posterior actuation assemblies 94, 96 can be driven independently in a manner providing the implant 10 with a lordotic profile, as set forth above. Stated differently, the anterior and posterior actuation assemblies 94, 96 can be operated in a manner causing at least one of the inferior and superior plates 20, 22 to tilt relative to the other plate 20, 22 with respect to the transverse direction T. In some embodiments, at least one of the plates 20, 22 can tilt relative to the other plate 20, 22 about at least one of the first and second central shaft axes $X_1$. This can be accomplished by placing the wedge assemblies 124, 126 of one of the anterior and posterior actuation assemblies 94, 96 at a degree of expansion that is different than that of the wedge assemblies 124, 126 of the other actuation assembly 94, 96. In the example lordotic configuration of FIGS. 38 through 40, in the posterior actuation assembly 96, the proximal and distal wedge assemblies 124, 126 thereof can be at about the collapsed configuration (FIG. 39) while, in the anterior actuation assembly 94, the wedge assemblies 124, 126 thereof can be expanded to near the first partially expanded configuration, thus causing the superior plate 22 to tilt relative to the inferior plate 20 with respect to the transverse direction T at a lordotic angle β (FIG. 40).

When at least one of the plates 20, 22 is tilted lordotically with respect to the other, a first distance $D_1$ between the inferior and superior bone-contacting surfaces 28, 30, measured along the vertical direction L and intersecting the central shaft axis $X_1$ of the anterior actuation assembly 94, can be shorter or longer than a second distance $D_2$ between the inferior and superior bone-contacting surfaces 28, 30, measured along the vertical direction L and intersecting the central shaft axis $X_1$ of the posterior actuation assembly 96. Additionally, when at least one of the plates 20, 22 is tilted lordotically with respect to the other, a vertical distance $D_3$ between the inferior and superior plates 20, 22 at the anterior side 16 of the implant 10 can be shorter or longer than a vertical distance $D_4$ between the plates 20, 22 at the posterior side 18 of the implant 10. As shown in FIG. 40, one of $D_3$ and $D_4$ can be as small as zero, at which point the internal contact surfaces 46 at the respective side 16, 18 of the implant 10 can define a fulcrum. In some embodiments, the internal faces 44 of the inferior and superior plate bodies 24, 26 can be curved, canted or can otherwise define a gap therebetween at one or both of the anterior and posterior sides 16, 18 so that at least one of the plates 20, 22 can be tilted lordotically while one of the anterior and posterior actuation assemblies 94, 96 is in the collapsed configuration (i.e., lordosis can be induced from the collapsed configuration).

It is to be appreciated that the lordotic profile illustrated in FIGS. 38 through 40 represents merely one of numerous lordotic profiles achievable with the implant 10 of the present disclosure. For example, the physician can actuate the anterior actuation assembly 94 to a first expanded configuration and the posterior actuation assembly 96 to a second expanded configuration to provide a difference between the first distance $D_1$ and the second distance $D_2$. In particular, the physician can actuate one of the anterior and posterior actuation assemblies 94, 96 to the fully expanded configuration while the other actuation assembly 96, 94 remains near the fully collapsed configuration to provide the implant 10 with a maximum lordotic angle β in the range of about 0 degrees and about 45 degrees. It is to be appreciated that the physician can independently place each of the actuation assemblies 94, 96 in the collapsed configuration, the fully expanded configuration, or any position therebetween to provide the implant 10 with the desired lordotic angle β. It is also to be appreciated that an initial lordotic angle β can be built in to the implant 10. In such embodiments, the inferior and superior bone plates 20, 22 can be configured such that the bone-contacting surfaces 28, 30 thereof are oriented at a lordotic angle β when the implant 10 is in the collapsed configuration.

Figure 41:
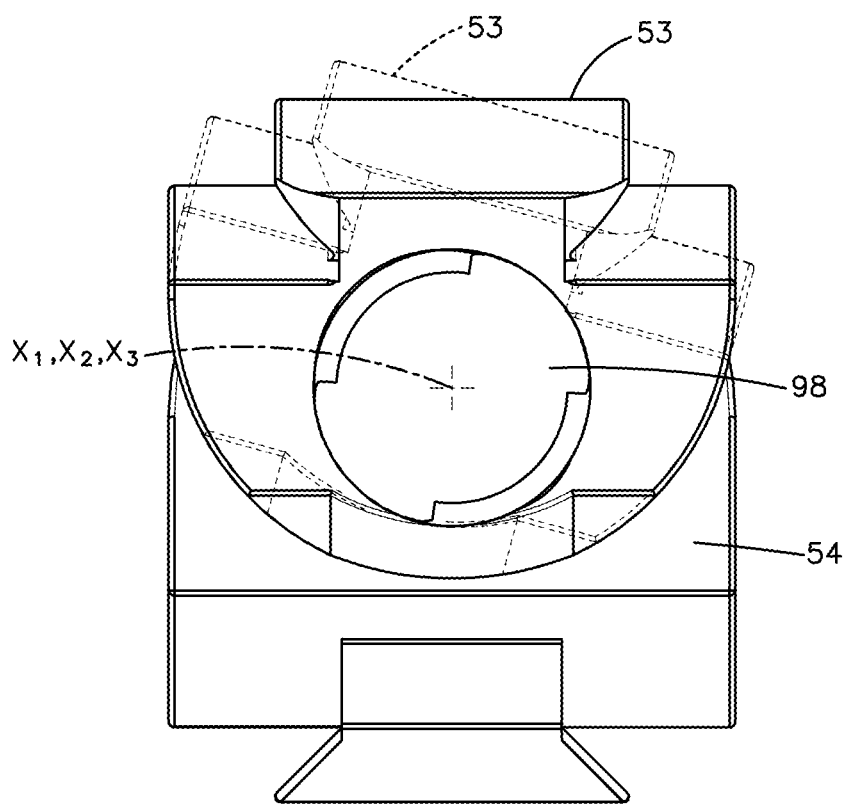
FIG. 41 is an end view of a pair of wedge members of an actuation assembly shown in FIGS. 5 and 6, illustrating rotation of one of the wedge members relative to the other.

The tilting can be rendered possible at least because the inferior plate 20 is rotationally interlocked with the first wedge 51, the superior plate 22 is rotationally interlocked with the second wedge 52, the second wedge 52 is rotationally interlocked with the third wedge 53, the third wedge 53 is rotatable about the respective central shaft axis $X_1$ relative to the fourth wedge 54 (as shown in FIG. 41), and the fourth wedge 54 is rotationally interlocked with the inferior plate 20 (either directly, as in the first phase of expansion, or via rotationally interlocking with the first wedge 51, which is rotationally interlocked with the inferior plate 20). It is to be appreciated that the fourth wedge 54 acts as a hinge of the implant 10 that facilitates lordotic tilting of at least one of the plates 20, 22. By utilizing the drive shaft 98 as the "through pin" of the hinge, the strength of the hinge is increased and the number of parts needed to complete the hinge is reduced. Additionally, the base surfaces 68 of the channels 56, 58, the base surfaces 142, 180, 262 of each wedge assembly 124, 126, and the ramp surfaces 148, 188, 190, 234, 268 of each wedge assembly 124, 126 collaboratively provide the implant 10 with added stability and strength to withstand inner body forces during and after implantation.

It is also to be appreciated that implant 10 provides the physician with enhanced freedom regarding the sequencing of achieving the desired expansion and/or lordosis of the implant 10. In particular, after predetermining the desired amount of expansion and/or lordosis of the implant 10 in the intervertebral space 5, the physician can insert the implant 10 in the collapsed configuration into the intervertebral space 5 along the medial-lateral direction, as shown in FIG. 1. If both expansion and lordosis are desired, the physician can expand the implant 10 uniformly to a partially expanded configuration, and then expand or retract the implant 10 in a non-uniform manner to achieve the desired lordotic angle β of the implant 10. The implant 10 can be expanded or retracted non-uniformly in various ways, including, for example: operating one of the actuation assemblies 94, 96 independently; operating both actuation assemblies 94, 96 simultaneously but at different rates; operating both actuation assemblies 94, 96 simultaneously but in different rotational directions; or any combination of the foregoing. The design of the implant 10, as disclosed herein allows the physician to utilize any of the foregoing modes of expansion, contraction and/or lordosis to achieve the final desired configuration, and to adjust the configuration of the implant 10 as necessary, including during subsequent physical procedures on the patient. The compact nature of the implant 10 in the collapsed configuration allows the implant 10 to fit within the standard lumbar disc space. Additionally, because the implant 10 can be adjusted to achieve up to 30 mm or more of expansion and up to 45 degrees or more of lordosis, the physician can use the implant 10 in many different locations within the spine and for many different purposes.

Figure 42:
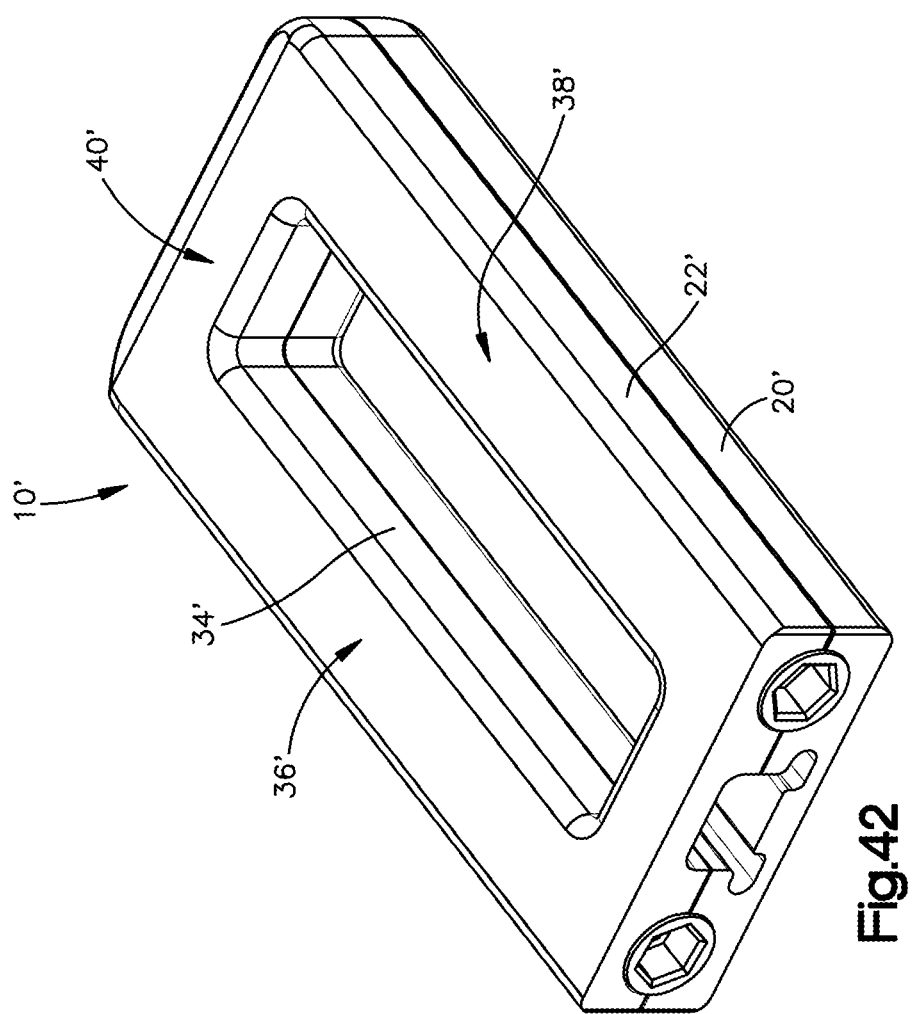
FIG. 42 is a perspective view of an implant in a collapsed configuration, according to a second example embodiment of the present disclosure.

Referring now to FIG. 42, a second embodiment of the implant 10' is shown. It is to be appreciated that the second embodiment can be similar to the first embodiment of the implant shown in FIGS. 1 through 41. Accordingly, the same reference numbers used above with reference to the first embodiment can be also used with a "prime" notation in reference to second embodiment. It is also to be appreciated that, unless otherwise set forth below, the components (and features thereof) of the implant 10' of the second embodiment can be similar to those of the first embodiment.

The inferior and superior plates 20', 22' of the second embodiment can define a single vertical aperture 34' extending through the implant 10' along the vertical direction V. The anterior and posterior portions 36', 38' of the implant 10 can be located on opposite sides of the vertical aperture 34'. The distal portion 40' of the implant 10' can be spaced from the vertical aperture 34' in the distal direction.

Figure 43:
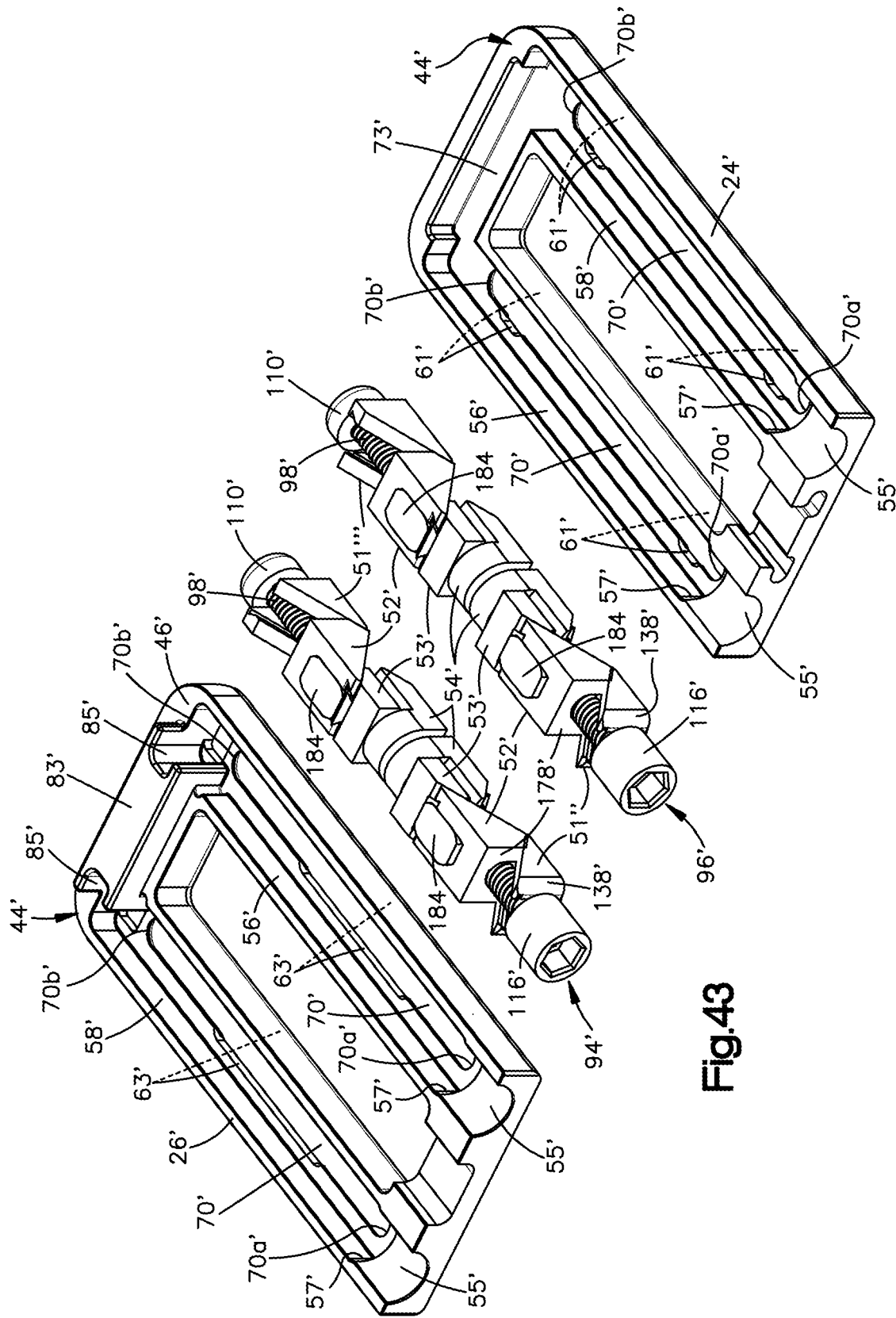
FIG. 43 is another perspective view of the implant of FIG. 42, shown with bone plates of the implant separated in a manner showing an internal expansion mechanism of the implant in a collapsed configuration, and also with a top one of the bone plates unfolded in book-like fashion showing internal faces of the bone plates.

Referring now to FIG. 43, the anterior and posterior channels 56', 58' of each of the inferior and superior plate bodies 24', 26' can include a proximal channel portion 55' that is contoured to match the outer contour of the nut socket 116'. At a distal end of each proximal channel portion 55', each plate body 24', 26' can define a shoulder 57'. The shoulders 57' of the inferior plate body 24' can be configured to abut the external faces 138' of the first wedges 51' of the anterior and posterior actuation assemblies 94', 96'. The shoulders 57' of the superior plate body 22' can be configured to abut, or at least be adjacent to, the external faces 178' of the second wedges 52' of the actuation assemblies 94', 96' when the actuation assemblies 94', 96' are in the fully expanded configuration.

Each of the channels 56', 58' of the inferior plate body 24' can define a first pair of cutouts 59' and a second pair of cutouts 61' spaced from each other along the longitudinal direction L. In each channel 56', 58', the cutouts 59' of the first pair can be opposed to each other along the transverse direction T, and the cutouts 61' of the second pair can be opposed to each other along the transverse direction T. While the view of FIG. 43 only shows the anterior cutout 61' of each pair, it is to be appreciated that the posterior cutout 61' of each pair can be a mirror image of the associated anterior cutout 61'. The first and second pairs of cutouts 59', 61' can each be in communication with the plate guide slots 70' of the inferior plate body 24' and can be sized to allow the base protrusions 142' of the first wedges 51' to be inserted into the plate guide slots 70' during assembly of the implant 10'.

Each of the channels 56', 58' of the superior plate body 26' can define a pair of central cutouts 63' generally centered with respect to the longitudinal direction L. In each channel 56', 58', the central cutouts 63' of each pair can be opposed to each other along the transverse direction T. While the view of FIG. 43 only shows the posterior central cutout 63' of each pair, it is to be appreciated that the anterior central cutout 63' of each pair can be a mirror image of the associated posterior central cutout 63'. The central cutouts 63' can each be in communication with the plate guide slots 70' of the superior plate body 26' and can be sized to allow the bottom protrusion 270' (FIGS. 44 through 46) of the fourth wedges 54' of each actuation assembly 94', 96' to be inserted into the plate guide slots 70' during assembly of the implant 10'.

With continued reference to FIG. 43, each of the plate guide slots 70' can define a proximal end 70a' and a distal end 70b'. In the inferior plate body 24', the proximal ends 70a' of the plate guide slots 70' can optionally be configured to abut the base protrusions of the first wedges 51'' of the proximal wedge assemblies 124', and the distal ends 70b' of the plate guide slots 70' can optionally be configured to abut the base protrusions of the first wedges 51''' of the distal wedge assemblies 126'. While the base protrusions of the first wedges 51'', 51''' of the present embodiment are not visible in FIG. 43, it is to be appreciated that these base protrusions can be configured similarly to the base protrusions 144, 144' shown in FIGS. 10 through 15. In the superior plate body 26', the proximal ends 70a' of the plate guide slots 70' can optionally be configured to abut the base protrusions 184' of the second wedges 52' of the proximal wedge assemblies 124' during operation of the implant, such as when each respective actuation assembly 94', 96' is in the fully expanded configuration. Similarly, the distal ends 70b' of the plate guide slots 70' can optionally be configured to abut the base protrusions 184' of the second wedges 52' of the distal wedge assemblies 126' during operation of the implant 10', such as when each respective actuation assembly 94', 96' is in the fully expanded configuration. It is to be appreciated that the proximal and distal ends 70a', 70b' of the guide slots 70' of the superior plate 22 can impede motion of the second wedges 52' in the external longitudinal direction $L_E$ during expansion of the implant 10.

At the distal portion 40' of the inferior plate body 24', the internal face 44' can define a single transverse slot 73' elongated along the transverse direction T. The distal portion 40' of the superior plate body 26' can define a single transverse protrusion 83' protruding beyond the internal contact surface 46' of the superior plate body 26'. When the implant 10' is in the collapsed configuration, the transverse protrusion 83' of the superior plate body 26' can nest within the transverse slot 73' of the inferior plate body 24'. The transverse protrusion 83' can define a pair of opposed recesses 85' extending into the protrusion 83' along the transverse direction T. The recesses 85' can be configured to receive therein portions of the heads 110' of the drive shafts 98' of the anterior and posterior actuation assemblies 94', 96', at least when the implant 10' is in the collapsed configuration.

It is to be appreciated that the third and fourth wedges 53', 54' of each of the actuation assemblies 94', 96' of the second embodiment can be different than their counterparts in the first embodiment. Referring to FIGS. 44 through 46, the third wedge body 216' can define an upper surface 231' extending between the internal face 226' and the fourth ramp 234' along the longitudinal direction L. The third wedge body 216' can define a vertical aperture 233' extending through the fourth ramp 234' and the guide protrusion 236', and can also define a pair of arms 235', 237' extending from the internal face 226' to the external face 228'. The vertical aperture 233' can be in communication with the central bore 230' of the third wedge 53'. A portion of the threading 232' of the central bore 230' can be defined on the inner sides of the arms 235', 237'. Each of the pair of arms 235', 237' can define a lower surface 239' (FIG. 46) that is canted toward the axis $X_2$ of the central bore 230' of the third wedge 53'. The rounded portion 244' of the third wedge 53' can extend downward from the lower surfaces 239' of the arms 235', 237', and can have a substantially semicircular profile in a vertical-transverse plane. The rounded portion 244' of the present embodiment can optionally not be inclined with respect to the longitudinal direction L. The rounded portion 244' can surround at least a portion of the central bore 230' of the third wedge body 216'.

The fourth wedge body 246' can define a front basket 253' extending from the external face 258' along the external longitudinal direction $L_E$. The front basket 253' can provide the bottom base surface 262 of the fourth wedge body 246' with increased length and thus increased stability as the bottom base surface 262 abuts and/or translates along the channel base surface 68. The external face 258' of the fourth wedge body 246' can be a first external face thereof, and the front basket 253' can define a second external face 255' that is spaced from the first external face 256' along the external longitudinal direction $L_E$. The second external face 255' can be positioned at the external end 250' of the fourth wedge body 246'. The bottom surface 262' of the fourth wedge body 246' can extend from the internal face 256' to the sixth ramp 268' along the longitudinal direction L and can extend along a portion of the basket 253'. The sixth ramp 268' can extend from the bottom surface 262' to the second external face 255' of the fourth wedge body 246'. The guide protrusion 270' of the fourth wedge body 246' of the second embodiment can be configured similarly to the guide protrusion 270' of the first embodiment.

The basket 253' can define a central recess 257' extending along the longitudinal direction L. The central recess 257' can be characterized as an extension of the central bore 264' of the fourth wedge body 246' along the basket 253'. The central recess 257' can separate an upper portion of the basket 253' into a pair of arms 259', 261' that each extend generally along the longitudinal direction L and each have an upper surface 263' that is canted towards the central bore axis $X_3$ of the fourth wedge 54'. The basket 253' can also define a trough 265' configured to receive the rounded portion 244' of the third wedge body 216'. The trough 265' can have a rounded profile that corresponds to the profile of the rounded portion 244' of the third wedge body 216' and can allow the rounded portion 244' of the third wedge body 216' to rotate within the trough 265 about the central bore axis $X_3$ of the third wedge body 216'. The central recess 257' can also define a portion of the threading 266' of the central bore 264' of the fourth wedge body 246'. The fourth wedge body 216' can define a vertical aperture 267' extending through the basket 253' at the external end 250' thereof. The vertical apertures 233', 267' of the third and fourth wedge bodies 216', 246' can be aligned with one another along the vertical direction V.

As shown in FIGS. 44 and 45, the third wedge body 216' can be coupled to the fourth wedge body 54' such that: the rounded portion 244' of the third wedge body 216' is received within the trough 265' of the fourth wedge body 246'; the internal face 226' of the third wedge body 216' abuts or is adjacent to the first external face 256' of the fourth wedge body; and the external face 228' of the third wedge body 216' is substantially aligned with the second external face 255' of the fourth wedge body 246' along the vertical direction V. When the plates 20', 22' are at a neutral (i.e., non-lordotic) configuration, a gap 275' is defined between the lower surfaces 239' of the arms 235', 237' of the third wedge body 216' and the upper surfaces 263' of the arms 259', 261' of the fourth wedge body 246'. The gap 275' and the canted arm surfaces 239', 263' can be configured to allow the third wedge body 216' to rotate relative to the fourth wedge body 246', as shown in FIG. 45. Additionally, the rounded portion 244' of the third wedge body 216' and the trough 265' of the fourth wedge body 246' can be cooperatively configured to translationally affix the third and fourth wedges 53', 54' together with respect to translation along the drive shaft 98'.

Figure 47:
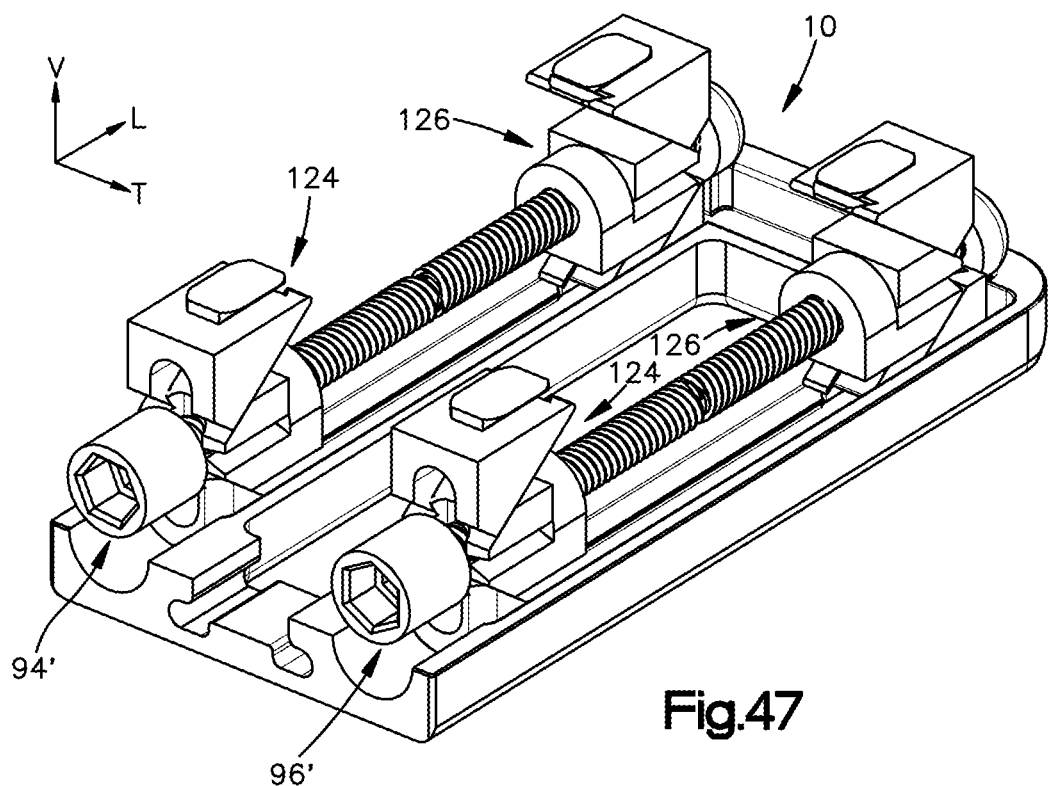
FIG. 47 is a perspective view of the implant of FIG. 42 shown in a fully expanded configuration with one of the bone plates removed for illustrative purposes.

Referring now to FIG. 47, the second embodiment of the implant 10' is shown with each wedge assembly 124', 126' in the fully expanded configuration (with the superior plate 22' removed for visualization purposes). It is to be appreciated that the actuation assemblies 94', 96' and the wedge assemblies 124', 126' of the second embodiment can operate as set forth above with respect to those of the first embodiment.

Figure 48:
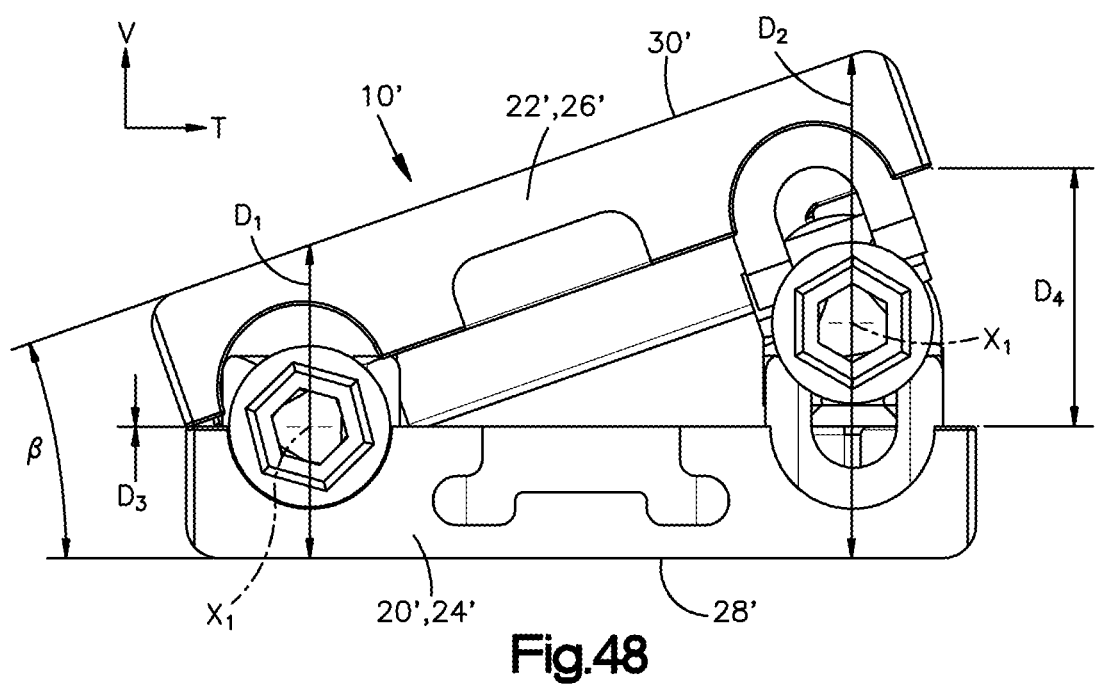
FIG. 48 is an end view of the implant of FIG. 42 in a lordotic configuration.
Figure 49:
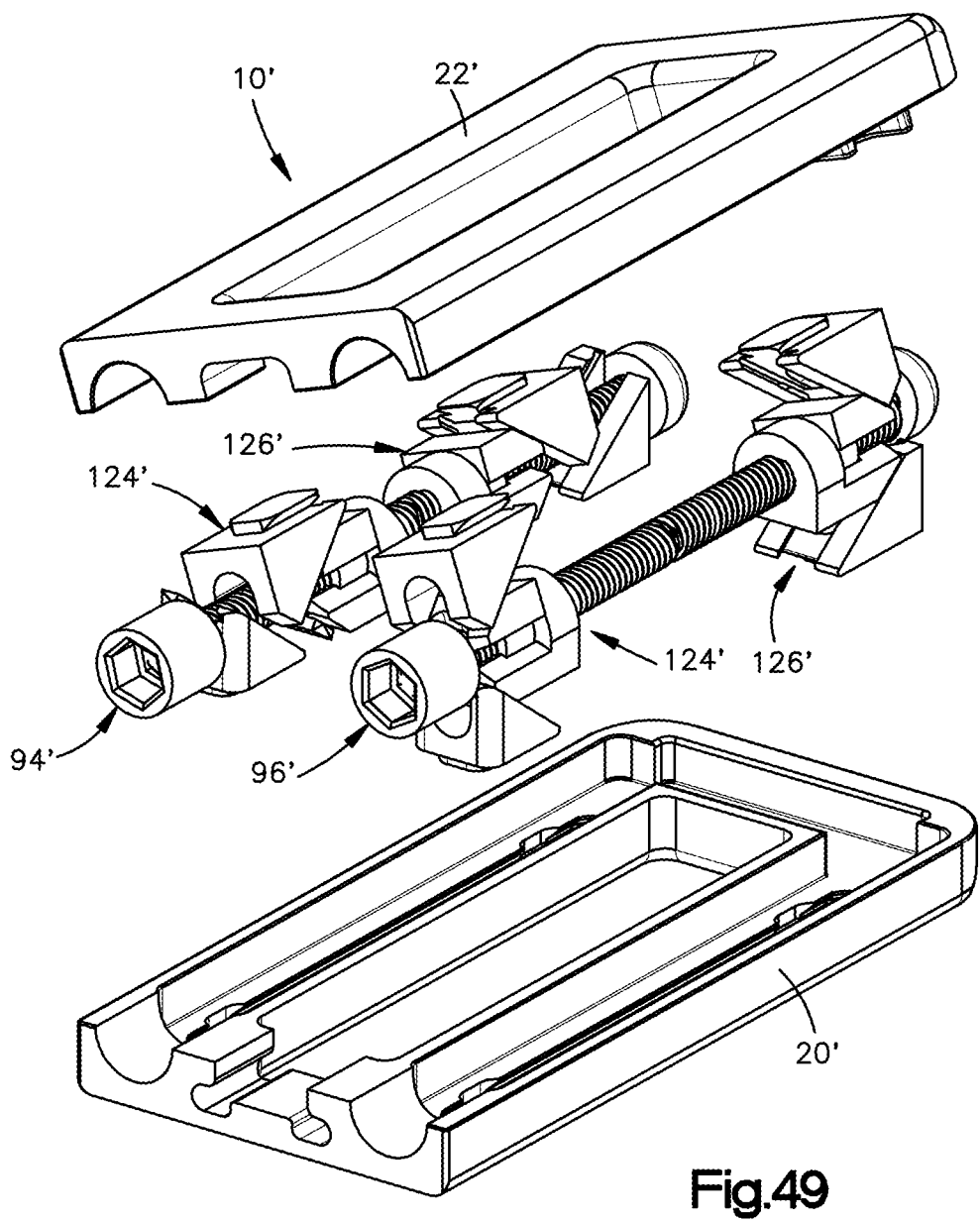
FIG. 49 is a partially exploded perspective view of the implant of FIG. 48.

Referring now to FIGS. 48 and 49, the actuation assemblies 94', 96' of the implant 10' can be operated independently so that the superior plate 22' is tilted relative to the inferior plate 20' with respect to the transverse direction T so as to provide the implant 10' with a lordotic profile, as set forth above. As shown in FIG. 48, the inferior and superior bone-contacting surfaces 28', 30' can be oriented at a lordotic angle β in the range of about 0 degrees and about 25 degrees. As set forth above, when at least one of the plates 20', 22' is tilted lordotically with respect to the other, a first vertical distance $D_1$ between the inferior and superior bone-contacting surfaces 28', 30' that intersects the associated central shaft axis $X_1$ can be shorter or longer than a second vertical distance $D_2$ between the bone-contacting surfaces 28', 30' that intersects the associated central shaft axis $X_1$. Additionally, when at least one of the plates 20', 22' is tilted lordotically with respect to the other, a vertical distance $D_3$ between the inferior and superior plates 20', 22' at the anterior side 16' of the implant 10' can be shorter or longer than a vertical distance $D_4$ between the plates 20', 22' at the posterior side 18' of the implant 10, as set forth above.

As shown in the example lordotic configuration of FIG. 49, in the anterior actuation assembly 94', the proximal and distal wedge assemblies 124', 126' thereof can be near the collapsed configuration while, in the posterior actuation assembly 96', the wedge assemblies 124', 126' thereof can be expanded near or at the fully expanded configuration, thus causing the lordotic tilting of the superior plate 22'. It is to be appreciated that, while FIG. 49 illustrates the inferior and superior plates 20', 22' separated vertically to provide an unobstructed view of the actuation assemblies 94', 96', the plates 20', 22' are shown at the same lordotic angle β as in FIG. 48.

It is to be appreciated that, while the illustrated embodiments depict the implant 10 having a pair of actuation assemblies 94, 96, in other embodiments (not shown), the implant 10 can have a single actuation assembly 94 to expand the implant 10 along the vertical direction V. In one such embodiment, the plates 20, 22 can be configured to maintain contact with each other in a hinge-like manner at one of the anterior and posterior sides 16, 18 so that operation of the single actuation assembly 94 expands the implant 10 vertically and simultaneously provides lordosis.

Figure 50:
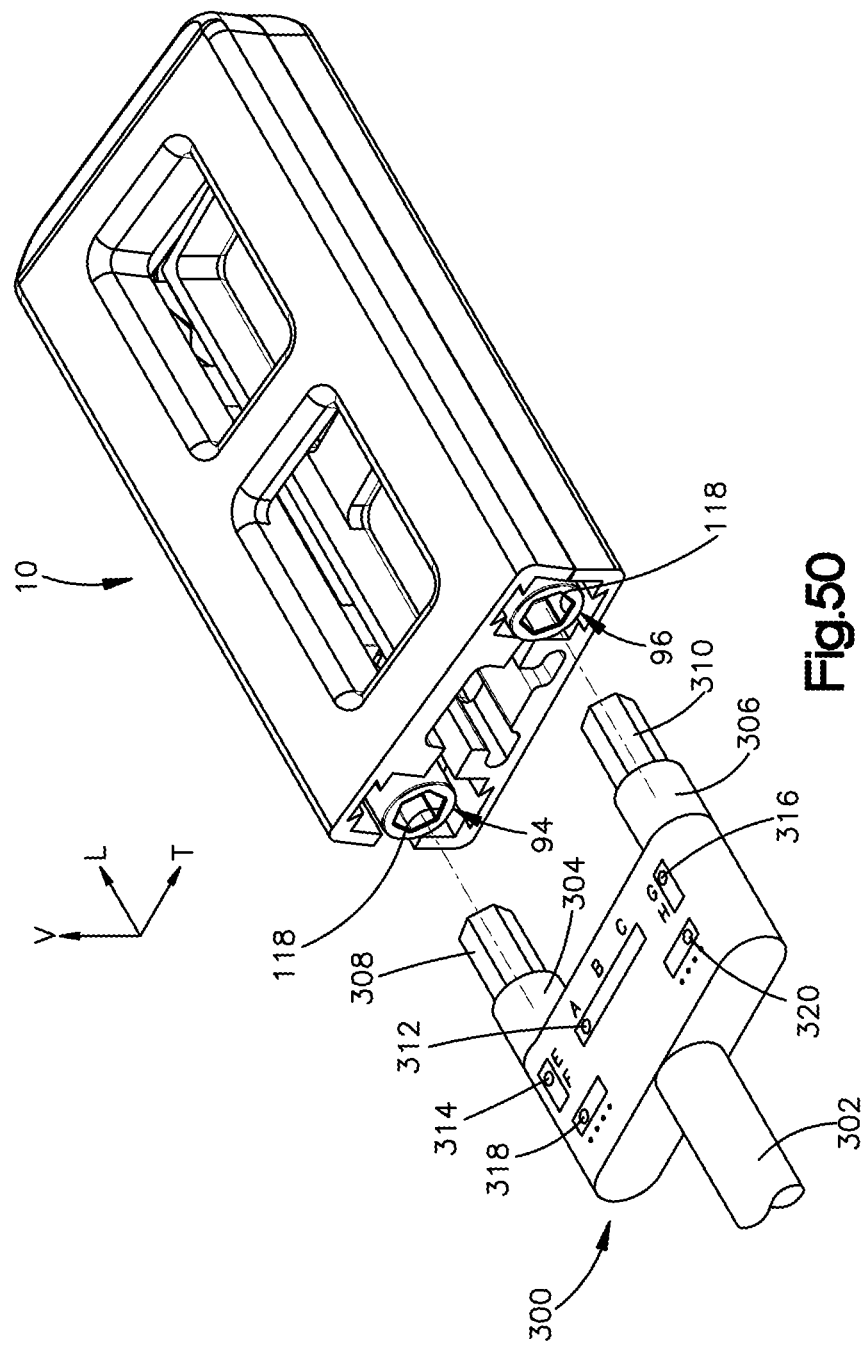
FIG. 50 is a perspective view of a driving tool configured to expand the implant shown in FIG. 38.

Referring now to FIG. 50, a driving tool 300 can be configured to engage the anterior and posterior actuation assemblies 94, 96 of the implant 10. For example, the driving tool 300 can include a handle 302 coupled to a first driver 304 and a second driver 306 that are spaced from each other along the transverse direction T. The first driver 304 can carry a first bit 308 configured to engage the drive coupling of the anterior actuation assembly 94 while the second driver 306 can carry a second bit 310 configured to engage the drive coupling of the posterior actuation assembly 96. For example, in the illustrated embodiments, the first and second bits 308, 310 can each define a hex profile configured to engage a corresponding hex profile of the socket aperture 118 of the corresponding actuation assembly 94, 96.

The driving tool 300 can include a one or more selector switches that allows the physician to select between various modes of operation of the tool 300. For example, a first selector switch 312 can toggle between a first drive mode A, a second drive mode B, and a third drive mode C. In the first drive mode A, the tool 300 can be set to operate only the first driver 304. In the second drive mode B, the tool 300 can be set to operate the first and second drivers 304, 306 simultaneously. In the third mode C, the tool 300 can be set to operate only the second driver 306.

A second selector switch 314 can be in communication with the first driver 304. For example, the second selector switch 314 can toggle between a first position E, wherein the tool 300 is set to rotate the first driver 304 in the clockwise direction, and a second position F, wherein the tool 300 is set to rotate the first driver 304 in the counterclockwise direction. Similarly, a third selector switch 316 can be in communication with the second driver 306. For example, the third selector switch 316 can toggle between a first position G, wherein the tool 300 is set to rotate the second driver 306 in the clockwise direction, and a second position H, wherein the tool 300 is set to rotate the second driver 306 in the counterclockwise direction.

A fourth selector switch 318 can allow the physician to select a torque and/or speed setting of the first driver 304. A fifth selector switch 320 can allow the physician to select a torque and/or speed setting of the second driver 306. Accordingly, the first, second, third, fourth, and fifth selector switches 312, 314, 316, 318, 320 allow the physician to use the tool 300 to operate the anterior and posterior actuation assemblies 94, 96 uniformly or independently as desired. Additionally, the selector switches can also allow the physician to tailor the rotational direction, speed and/or torque of each of the actuation assemblies 94, 96 independently.

Although the disclosure has been described in detail, it should be understood that various changes, substitutions, and alterations can be made herein without departing from the spirit and scope of the invention as defined by the appended claims. Additionally, any of the embodiments disclosed herein can incorporate features disclosed with respect to any of the other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An intervertebral implant configured to iterate between a collapsed configuration and an expanded configuration, the implant comprising:
a first plate and a second plate spaced from one another along a first direction, the first plate defining a first bone-contacting surface, the second plate defining a second bone-contacting surface facing away from the first bone-contacting surface along the first direction; and a first expansion assembly and a second expansion assembly each disposed between the first and second plates with respect to the first direction, each of the first and second expansion assemblies including:
  a first ramp extending from the first plate toward the second plate;
  a second ramp and a third ramp each extending from the second plate toward the first plate;
  an expansion wedge defining a fourth ramp,
  wherein each of the first, second, third, and fourth ramps is inclined with respect to a second direction that is substantially perpendicular to the first direction; and
  an actuator configured to apply a drive force to the expansion wedge so as to cause 1) the fourth ramp to ride along the third ramp so as to increase a distance between the first and second bone-contacting surfaces along the first direction, and 2) the second ramp to ride along the first ramp, thereby further increasing the distance, thereby iterating the implant from the collapsed configuration to the expanded configuration, wherein at least a portion of the expansion wedge of each of the first and second expansion assemblies is rotatable with respect to at least one of the first and second plates, and the respective actuators of the first and second expansion assemblies are operable independent of one another so as to cause one of the first and second bone-contacting surfaces to tilt relative to the other of the first and second bone-contacting surfaces.

2. The implant of claim 1, wherein the one of the first and second bone-contacting surfaces is configured to tilt relative to the other of the first and second bone-contacting surfaces at an angle up to and including about 25 degrees.

3. The implant of claim 1, wherein:
the expansion wedge and the first, second, and third ramps of each of the first and second expansion assemblies are configured to iterate between the collapsed configuration and the expanded configuration with respect to the first direction, and
the one of the first and second bone-contacting surfaces is configured to tilt relative to the other of the first and second bone-contacting surfaces such that one of the first and second expansion assemblies is in the expanded configuration while the other of the first and second expansion assemblies is in the collapsed configuration.

4. The implant of claim 1, wherein each actuator is configured to apply the drive force along a respective axis, and each expansion wedge comprises:
  a first member that defines the at least the portion of the expansion wedge, the first member defining the fourth ramp; and
  a second member,
  wherein the first member is rotatable with respect to the second member about the respective axis, thereby allowing the one of the first and second bone-contacting surfaces to tilt relative to the other of the first and second bone-contacting surfaces.

5. The implant of claim 4, wherein the first member is configured to ride along the third ramp responsive to the drive force, and the second member is configured to ride along the first ramp responsive to the drive force.

6. The implant of claim 5, wherein:
the first member, the second and third ramps, and the second plate are rotationally locked with respect to each other, and
the second member, the first ramp, and the first plate are rotationally locked with respect to each other.

7. The implant of claim 4, wherein the respective axes of the actuators of the first and second expansion assemblies are oriented along the second direction.

8. The implant of claim 7, wherein the respective axes are spaced from each other along a third direction that is substantially perpendicular to the first and second directions.

9. The implant of claim 4, wherein each actuator is threadedly coupled to the first and second members of the respective expansion wedge, such that rotation of the actuator about the respective axis imparts the drive force, thereby causing the first and second members to threadedly translate along the actuator.

10. The implant of claim 9, wherein the first and second members of each expansion wedge abut one another.

11. An implant, comprising:
an actuation assembly extending between first and second endplates, the actuation assembly arranged along an axis that is oriented along an axial direction, wherein the actuation assembly comprises:
  a support wedge that supports one of the first and second endplates;
  a first expansion wedge that is slidable with respect to the support wedge; and
  a second expansion wedge that is slidable with respect to the first endplate; and
  an actuator that is movable with respect to the axis so as to drive the first and second expansion wedges along the axial direction so as to cause the first expansion wedge to ride along the support wedge, thereby increasing a distance between the first and second endplates;
wherein the first and second expansion wedges are rotatable relative to each other about the axis, thereby allowing one of the first and second endplates to tilt relative to the other of the first and second endplates as the distance increases.

12. The implant of claim 11, wherein:
the support wedge supports the second endplate;
the implant further comprises another support wedge that supports the first endplate; and
the second expansion wedge is configured to ride along the another support wedge to further increase the distance between the first and second endplates.

13. The implant of claim 12, wherein:
the support wedge includes a guide feature having a geometry;
the first expansion wedge includes a guide element having a geometry that is complimentary to the geometry of the guide feature, such that the guide element is configured to ride along the guide feature; and
the guide feature and the guide element are configured to rotationally lock the first expansion wedge to the support wedge.

14. The implant of claim 13, wherein:
the second endplate defines a guide feature having a geometry and extending along the axial direction; and
the geometry of the guide element of the first expansion wedge is complimentary with the geometry of the guide feature of the second endplate, such that the guide element of the first expansion wedge is further configured to ride along the guide feature of the second endplate.

15. The implant of claim 12, wherein:
the another support wedge includes a guide feature having a geometry;
the second expansion wedge includes a guide element having a geometry that is complimentary to the geometry of the guide feature of the another support wedge, such that the guide element of the second expansion wedge is configured to ride along the guide feature of the another support wedge; and
the guide feature of the another support wedge and the guide element of the second expansion wedge are configured to rotationally lock the second expansion member to the another support wedge.

16. The implant of claim 15, wherein:
the first endplate defines a guide feature having a geometry and extending along the axial direction, and
the guide element of the second expansion wedge is further configured to ride along the guide feature of the first endplate.

17. The implant of claim 16, wherein the implant is configured to iterate between a fully collapsed configuration, in which the distance between the first and second endplates is at a minimum, and a fully expanded configuration, in which the distance is at a maximum, such that:
when the implant is in the fully collapsed configuration, the guide element of the second expansion wedge is engaged with the guide feature of the first endplate and is remote from the guide feature of the another support wedge; and
when the implant is in the fully expanded configuration, the guide element of the second expansion wedge is engaged with the guide feature of the another support wedge and is remote from the guide feature of the first endplate.

18. The implant of claim 11, wherein the one of the first and second endplates is configured to tilt relative to the other of the first and second endplates at an angle up to and including about 25 degrees.

19. The implant of claim 11, wherein the axial direction is substantially perpendicular to a first direction, and the distance between the first and second endplates increases along the first direction.

20. The implant of claim 19, wherein the actuator is a drive shaft configured to rotate about the axis to drive the first and second expansion wedges along the axial direction.

* * * * *